US012629522B1

(12) United States Patent
Yu

(10) Patent No.: US 12,629,522 B1
(45) Date of Patent: May 19, 2026

(54) NEUROSTIMULATION SYSTEMS WITH EVENT PATTERN DETECTION AND CLASSIFICATION

(71) Applicant: Cala Health, Inc., San Mateo, CA (US)

(72) Inventor: Jai Y. Yu, Burlingame, CA (US)

(73) Assignee: Cala Health, Inc., San Mateo, CA (US)

( * ) Notice: Subject to any disclaimer, the term of this patent is extended or adjusted under 35 U.S.C. 154(b) by 0 days.

(21) Appl. No.: 18/528,127

(22) Filed: Dec. 4, 2023

Related U.S. Application Data

(63) Continuation of application No. 17/061,231, filed on Oct. 1, 2020, now Pat. No. 11,890,468.

(60) Provisional application No. 62/933,816, filed on Nov. 11, 2019, provisional application No. 62/910,260, filed on Oct. 3, 2019.

(51) Int. Cl.
| | |
|---|---|
| A61N 1/36 | (2006.01) |
| A61N 1/02 | (2006.01) |
| A61N 1/04 | (2006.01) |
| A61N 1/08 | (2006.01) |
| G16H 20/30 | (2018.01) |
| G16H 50/20 | (2018.01) |

(52) U.S. Cl.
CPC ......... *A61N 1/36031* (2017.08); *A61N 1/025* (2013.01); *A61N 1/0456* (2013.01); *A61N 1/0476* (2013.01); *A61N 1/08* (2013.01); *G16H 20/30* (2018.01); *G16H 50/20* (2018.01)

(58) Field of Classification Search
None
See application file for complete search history.

(56) References Cited

U.S. PATENT DOCUMENTS

| | | | |
|---|---|---|---|
| 3,204,637 | A | 9/1965 | Frank et al. |
| 3,870,051 | A | 3/1975 | Brindley |
| 4,103,808 | A | 8/1978 | Hallman et al. |
| 4,233,986 | A | 11/1980 | Tannenbaum |
| 4,300,575 | A | 11/1981 | Wilson |
| 4,313,441 | A | 2/1982 | Buffet |
| 4,458,696 | A | 7/1984 | Larimore |
| 4,461,075 | A | 7/1984 | Bailey |
| 4,539,996 | A | 9/1985 | Engel |
| 4,569,351 | A | 2/1986 | Tang |
| 4,582,049 | A | 4/1986 | Ylvisaker |
| 4,729,377 | A | 3/1988 | Granek et al. |
| 4,739,764 | A | 4/1988 | Lue et al. |

(Continued)

FOREIGN PATENT DOCUMENTS

| | | |
|---|---|---|
| CN | 1135722 | 11/1996 |
| CN | 1547483 | 11/2004 |

(Continued)

OTHER PUBLICATIONS

U.S. Appl. No. 15/277,946, filed Sep. 27, 2016, Rosenbluth et al.

(Continued)

*Primary Examiner* — Michael W Kahelin

(74) *Attorney, Agent, or Firm* — Knobbe, Martens, Olson & Bear, LLP

(57) ABSTRACT

Systems, devices, and methods for electrically stimulating peripheral nerve(s) to treat various disorders are disclosed, as well as signal processing systems and methods for enhancing device monitoring protocols and detecting abnormal patient usage of the device.

8 Claims, 34 Drawing Sheets

(56) References Cited

U.S. PATENT DOCUMENTS

| | | | |
|---|---|---|---|
| 4,763,659 | A | 8/1988 | Dunseath, Jr. |
| 4,769,881 | A | 9/1988 | Pedigo et al. |
| 4,771,779 | A | 9/1988 | Tanagho et al. |
| 4,917,092 | A | 4/1990 | Todd et al. |
| 4,981,146 | A | 1/1991 | Bertolucci |
| 4,982,432 | A | 1/1991 | Clark et al. |
| 4,996,987 | A | 3/1991 | Petrofsky |
| 5,003,978 | A | 4/1991 | Dunseath, Jr. |
| 5,052,391 | A | 10/1991 | Silverstone et al. |
| 5,070,862 | A | 12/1991 | Berlant |
| 5,137,507 | A | 8/1992 | Park |
| 5,330,516 | A | 7/1994 | Nathan |
| 5,395,398 | A | 3/1995 | Rogozinski |
| 5,397,338 | A | 3/1995 | Grey et al. |
| 5,514,175 | A | 5/1996 | Kim et al. |
| 5,540,235 | A | 7/1996 | Wilson |
| 5,562,707 | A | 10/1996 | Prochazka et al. |
| 5,562,717 | A | 10/1996 | Tippey et al. |
| 5,573,011 | A | 11/1996 | Felsing |
| 5,575,294 | A | 11/1996 | Perry et al. |
| 5,606,968 | A | 3/1997 | Mang |
| 5,643,173 | A | 7/1997 | Welles |
| 5,775,331 | A * | 7/1998 | Raymond ................ A61B 5/05 |
| | | | 600/554 |
| 5,833,709 | A | 11/1998 | Rise et al. |
| 5,833,716 | A | 11/1998 | Bar-Or et al. |
| 5,899,922 | A | 5/1999 | Loos |
| 5,961,542 | A | 10/1999 | Agarwala |
| 6,016,449 | A | 1/2000 | Fischell et al. |
| 6,076,018 | A | 6/2000 | Sturman |
| 6,081,744 | A | 6/2000 | Loos |
| 6,161,044 | A | 12/2000 | Silverstone |
| 6,178,352 | B1 | 1/2001 | Gruzdowich et al. |
| 6,351,674 | B2 | 2/2002 | Silverstone |
| 6,364,841 | B1 | 4/2002 | White et al. |
| 6,366,813 | B1 | 4/2002 | DiLorenzo |
| 6,366,814 | B1 | 4/2002 | Boveja et al. |
| 6,419,644 | B1 | 7/2002 | White et al. |
| 6,445,955 | B1 | 9/2002 | Michelson et al. |
| 6,449,512 | B1 | 9/2002 | Boveja |
| 6,453,204 | B1 | 9/2002 | Rhoads |
| 6,505,074 | B2 | 1/2003 | Boveja et al. |
| 6,546,290 | B1 | 4/2003 | Shloznikov |
| 6,564,103 | B2 | 5/2003 | Fischer et al. |
| 6,572,555 | B2 | 6/2003 | White et al. |
| 6,579,270 | B2 | 6/2003 | Sussman et al. |
| 6,641,546 | B2 | 11/2003 | White et al. |
| 6,652,449 | B1 | 11/2003 | Gross et al. |
| 6,662,052 | B1 | 12/2003 | Sarwal et al. |
| 6,678,548 | B1 * | 1/2004 | Echauz ................ A61B 5/4094 |
| | | | 600/544 |
| 6,701,185 | B2 | 3/2004 | Burnett et al. |
| 6,704,603 | B1 | 3/2004 | Gesotti |
| 6,731,987 | B1 | 5/2004 | McAdams et al. |
| 6,735,474 | B1 | 5/2004 | Loeb et al. |
| 6,735,480 | B2 | 5/2004 | Giuntoli et al. |
| 6,788,976 | B2 | 9/2004 | Gesotti |
| 6,819,956 | B2 | 11/2004 | DiLorenzo |
| 6,827,693 | B2 | 12/2004 | White et al. |
| 6,829,510 | B2 | 12/2004 | Nathan et al. |
| 6,836,684 | B1 | 12/2004 | Rijkhoff et al. |
| 6,862,480 | B2 | 3/2005 | Cohen et al. |
| 6,892,098 | B2 | 5/2005 | Ayal et al. |
| 6,937,905 | B2 | 8/2005 | Carroll et al. |
| 6,959,215 | B2 | 10/2005 | Gliner et al. |
| 6,959,216 | B2 | 10/2005 | Faghri |
| 6,988,005 | B2 | 1/2006 | McGraw et al. |
| 7,010,352 | B2 | 3/2006 | Hogan |
| 7,089,061 | B2 | 8/2006 | Grey |
| 7,146,220 | B2 | 12/2006 | Dar et al. |
| 7,162,305 | B2 | 1/2007 | Tong et al. |
| 7,171,266 | B2 | 1/2007 | Gruzdowich et al. |
| 7,177,694 | B2 | 2/2007 | Elbaum |
| 7,177,703 | B2 | 2/2007 | Boveja et al. |
| 7,209,787 | B2 | 4/2007 | DiLorenzo |
| 7,228,178 | B2 | 6/2007 | Carroll et al. |
| 7,231,254 | B2 | 6/2007 | DiLorenzo |
| 7,236,830 | B2 | 6/2007 | Gliner |
| 7,254,444 | B2 | 8/2007 | Moore et al. |
| 7,277,758 | B2 | 10/2007 | DiLorenzo |
| 7,283,866 | B2 | 10/2007 | Mumford et al. |
| 7,324,851 | B1 | 1/2008 | DiLorenzo |
| 7,326,235 | B2 | 2/2008 | Edwards |
| 7,328,068 | B2 | 2/2008 | Spinelli et al. |
| 7,349,739 | B2 | 3/2008 | Harry et al. |
| 7,353,064 | B2 | 4/2008 | Gliner et al. |
| 7,369,896 | B2 | 5/2008 | Gesotti |
| 7,499,747 | B2 | 3/2009 | Kieval et al. |
| 7,529,582 | B1 | 5/2009 | DiLorenzo |
| 7,558,610 | B1 | 7/2009 | Odderson |
| 7,636,602 | B2 | 12/2009 | Baru Fassio et al. |
| 7,640,052 | B2 | 12/2009 | Weinstock |
| 7,643,880 | B2 | 1/2010 | Tanagho et al. |
| 7,643,882 | B2 | 1/2010 | Boston |
| 7,647,112 | B2 | 1/2010 | Tracey et al. |
| 7,650,190 | B2 | 1/2010 | Zhou et al. |
| 7,657,317 | B2 | 2/2010 | Thacker et al. |
| 7,742,820 | B2 | 6/2010 | Wyler et al. |
| 7,761,166 | B2 | 7/2010 | Giftakis et al. |
| 7,769,464 | B2 | 8/2010 | Gerber et al. |
| 7,801,585 | B1 | 9/2010 | Weinstock |
| 7,857,771 | B2 | 12/2010 | Alwan et al. |
| 7,899,527 | B2 | 3/2011 | Yun et al. |
| 7,899,556 | B2 | 3/2011 | Nathan et al. |
| 7,917,201 | B2 | 3/2011 | Gozani et al. |
| 7,930,034 | B2 | 4/2011 | Gerber |
| 7,949,403 | B2 | 5/2011 | Palermo et al. |
| 7,957,814 | B2 | 6/2011 | Goetz et al. |
| 7,974,696 | B1 | 7/2011 | DiLorenzo |
| 7,974,698 | B2 | 7/2011 | Tass et al. |
| 7,991,476 | B2 | 8/2011 | Nachum |
| 7,996,088 | B2 | 8/2011 | Marrosu et al. |
| 7,998,092 | B2 | 8/2011 | Avni |
| 8,000,796 | B2 | 8/2011 | Tass |
| 8,025,632 | B2 | 9/2011 | Einarsson |
| 8,046,083 | B2 | 10/2011 | Teganthoff et al. |
| 8,064,988 | B2 | 11/2011 | Weinstock |
| 8,075,499 | B2 | 12/2011 | Nathan et al. |
| 8,086,318 | B2 | 12/2011 | Strother et al. |
| 8,108,047 | B2 | 1/2012 | Schumann |
| 8,121,694 | B2 | 2/2012 | Molnar et al. |
| 8,145,316 | B2 | 3/2012 | Deem et al. |
| 8,165,668 | B2 | 4/2012 | Dacey, Jr. et al. |
| 8,165,685 | B1 | 4/2012 | Knutson et al. |
| 8,170,658 | B2 | 5/2012 | Dacey, Jr. et al. |
| 8,175,718 | B2 | 5/2012 | Wahlgren et al. |
| 8,187,209 | B1 | 5/2012 | Guiffrida et al. |
| 8,190,249 | B1 | 5/2012 | Gharieb et al. |
| 8,195,287 | B2 | 6/2012 | Dacey, Jr. et al. |
| 8,209,036 | B2 | 6/2012 | Nathan et al. |
| 8,219,188 | B2 | 7/2012 | Craig |
| 8,233,988 | B2 | 7/2012 | Errico et al. |
| 8,260,439 | B2 | 9/2012 | Diubaldi et al. |
| 8,265,763 | B2 | 9/2012 | Fahey |
| 8,301,215 | B2 | 10/2012 | Lee |
| 8,306,624 | B2 | 11/2012 | Gerber et al. |
| 8,308,665 | B2 | 11/2012 | Harry et al. |
| 8,313,443 | B2 | 11/2012 | Tom |
| 8,326,398 | B2 | 12/2012 | Weinstock |
| 8,326,432 | B2 | 12/2012 | Kalisek |
| 8,343,026 | B2 | 1/2013 | Gardiner et al. |
| 8,364,257 | B2 | 1/2013 | Van Den Eerenbeemd et al. |
| 8,374,701 | B2 | 2/2013 | Hyde et al. |
| 8,380,314 | B2 | 2/2013 | Pankan et al. |
| 8,382,688 | B2 | 2/2013 | Dar et al. |
| 8,391,970 | B2 | 3/2013 | Tracey et al. |
| 8,396,556 | B2 | 3/2013 | Libbus et al. |
| 8,406,841 | B2 | 3/2013 | Lin et al. |
| 8,409,116 | B2 | 4/2013 | Wang et al. |
| 8,412,338 | B2 | 4/2013 | Faltys |
| 8,414,507 | B2 | 4/2013 | Asada |
| 8,417,351 | B2 | 4/2013 | Kilger |
| 8,428,719 | B2 | 4/2013 | Napadow |
| 8,430,805 | B2 | 4/2013 | Burnett et al. |

(56) References Cited

U.S. PATENT DOCUMENTS

| | | | |
|---|---|---|---|
| 8,435,166 B2 | 5/2013 | Burnett et al. |
| 8,447,411 B2 | 5/2013 | Skelton et al. |
| 8,452,410 B2 | 5/2013 | Emborg et al. |
| 8,463,374 B2 | 6/2013 | Hudson et al. |
| 8,473,064 B2 | 6/2013 | Castel et al. |
| 8,538,512 B1 | 9/2013 | Bibian et al. |
| 8,548,594 B2 | 10/2013 | Thimineur et al. |
| 8,571,687 B2 | 10/2013 | Libbus et al. |
| 8,581,731 B2 | 11/2013 | Purks et al. |
| 8,583,238 B1 | 11/2013 | Heldman et al. |
| 8,588,884 B2 | 11/2013 | Hegde et al. |
| 8,588,917 B2 | 11/2013 | Whitehurst et al. |
| 8,608,671 B2 | 12/2013 | Kinoshita et al. |
| 8,626,305 B2 | 1/2014 | Nielsen et al. |
| 8,639,342 B2 | 1/2014 | Possover |
| 8,644,904 B2 | 2/2014 | Chang et al. |
| 8,644,938 B2 | 2/2014 | Craggs |
| 8,660,656 B2 | 2/2014 | Moser et al. |
| 8,666,496 B2 | 3/2014 | Simon et al. |
| 8,679,038 B1 | 3/2014 | Giuffrida |
| 8,682,441 B2 | 3/2014 | De Ridder |
| 8,688,220 B2 | 4/2014 | Degiorgio et al. |
| 8,694,104 B2 | 4/2014 | Libbus et al. |
| 8,694,110 B2 | 4/2014 | Nathan et al. |
| 8,702,584 B2 | 4/2014 | Rigaux et al. |
| 8,702,629 B2 | 4/2014 | Giuffrida et al. |
| 8,706,241 B2 | 4/2014 | Firlik et al. |
| 8,718,780 B2 | 5/2014 | Lee |
| 8,738,143 B2 | 5/2014 | Tucker et al. |
| 8,740,825 B2 | 6/2014 | Ehrenreich et al. |
| 8,744,587 B2 | 6/2014 | Miesel et al. |
| 8,755,892 B2 | 6/2014 | Amurthur et al. |
| D709,874 S | 7/2014 | Aumiller et al. |
| 8,768,452 B2 | 7/2014 | Gerber |
| 8,788,045 B2 | 7/2014 | Gross et al. |
| 8,788,049 B2 | 7/2014 | Lasko et al. |
| 8,792,977 B2 | 7/2014 | Kakei et al. |
| 8,798,698 B2 | 8/2014 | Kim et al. |
| 8,821,416 B2 | 9/2014 | Johansson et al. |
| 8,825,163 B2 | 9/2014 | Grill et al. |
| 8,825,165 B2 | 9/2014 | Possover |
| 8,843,201 B1 | 9/2014 | Heldman et al. |
| 8,845,494 B2 | 9/2014 | Whitall et al. |
| 8,845,557 B1 | 9/2014 | Giuffrida et al. |
| 8,849,371 B2 | 9/2014 | Weinstock |
| 8,855,775 B2 | 10/2014 | Leyde |
| 8,862,238 B2 | 10/2014 | Rahimi et al. |
| 8,862,247 B2 | 10/2014 | Schoendorf et al. |
| 8,868,177 B2 | 10/2014 | Simon et al. |
| 8,874,227 B2 | 10/2014 | Simon et al. |
| 8,880,175 B2 | 11/2014 | Simon |
| 8,886,321 B2 | 11/2014 | Rohrer et al. |
| 8,892,200 B2 | 11/2014 | Wagner et al. |
| 8,897,870 B2 | 11/2014 | De Ridder |
| 8,903,494 B2 | 12/2014 | Goldwasser et al. |
| 8,920,345 B2 | 12/2014 | Greenberg et al. |
| 8,923,970 B2 | 12/2014 | Bar-Yoseph et al. |
| 8,948,876 B2 | 2/2015 | Gozani et al. |
| 8,961,439 B2 | 2/2015 | Yang et al. |
| 8,972,017 B2 | 3/2015 | Dar et al. |
| 8,989,861 B2 | 3/2015 | Su et al. |
| 9,002,477 B2 | 4/2015 | Burnett |
| 9,005,102 B2 | 4/2015 | Burnett et al. |
| 9,008,781 B2 | 4/2015 | Ahmed |
| 9,011,310 B2 | 4/2015 | Ahmed |
| 9,017,273 B2 | 4/2015 | Burbank et al. |
| 9,026,216 B2 | 5/2015 | Rossi et al. |
| 9,042,988 B2 | 5/2015 | Dilorenzo |
| 9,060,747 B2 | 6/2015 | Salorio |
| 9,079,029 B2 | 7/2015 | Weinstock |
| 9,089,691 B2 | 7/2015 | Libbus et al. |
| 9,095,351 B2 | 8/2015 | Sachs et al. |
| 9,095,417 B2 | 8/2015 | Dar et al. |
| 9,107,614 B2 | 8/2015 | Halkias et al. |
| 9,119,964 B2 | 9/2015 | Marnfeldt |
| 9,155,885 B2 | 10/2015 | Wei et al. |
| 9,155,890 B2 | 10/2015 | Guntinas-Lichius et al. |
| 9,162,059 B1 | 10/2015 | Lindenthaler |
| 9,168,374 B2 | 10/2015 | Su |
| 9,174,045 B2 | 11/2015 | Simon et al. |
| 9,186,095 B2 | 11/2015 | Machado et al. |
| 9,192,763 B2 | 11/2015 | Gerber et al. |
| 9,220,431 B2 | 12/2015 | Holzhacker |
| 9,220,895 B2 | 12/2015 | Siff et al. |
| 9,227,056 B1 | 1/2016 | Heldman et al. |
| 9,238,137 B2 | 1/2016 | Einav et al. |
| 9,238,142 B2 | 1/2016 | Heldman et al. |
| 9,242,085 B2 | 1/2016 | Hershey et al. |
| 9,248,285 B2 | 2/2016 | Haessler |
| 9,248,286 B2 | 2/2016 | Simon et al. |
| 9,248,297 B2 | 2/2016 | Hoyer et al. |
| 9,254,382 B2 | 2/2016 | Ahmad et al. |
| 9,259,577 B2 | 2/2016 | Kaula et al. |
| 9,265,927 B2 | 2/2016 | Yonce et al. |
| 9,282,928 B1 | 3/2016 | Giffrida |
| 9,289,607 B2 | 3/2016 | Su et al. |
| 9,301,712 B2 | 4/2016 | McNames et al. |
| 9,302,046 B1 | 4/2016 | Giuffrida et al. |
| 9,302,117 B2 | 4/2016 | De Vincentiis |
| 9,311,686 B2 | 4/2016 | Roush et al. |
| 9,314,190 B1 | 4/2016 | Giuffrida et al. |
| 9,314,622 B2 | 4/2016 | Embrey et al. |
| 9,332,918 B1 | 5/2016 | Buckley et al. |
| 9,339,213 B2 | 5/2016 | Otsamo et al. |
| 9,339,641 B2 | 5/2016 | Rajguru et al. |
| 9,345,872 B2 | 5/2016 | Groteke |
| 9,364,657 B2 | 6/2016 | Kiani et al. |
| 9,364,672 B2 | 6/2016 | Marnfeldt |
| 9,375,570 B2 | 6/2016 | Kiani et al. |
| 9,387,338 B2 | 7/2016 | Burnett |
| 9,393,430 B2 | 7/2016 | Demers et al. |
| 9,408,683 B2 | 8/2016 | St. Anne et al. |
| 9,414,776 B2 | 8/2016 | Sillay et al. |
| 9,415,205 B2 | 8/2016 | Lasko et al. |
| D767,436 S | 9/2016 | Goodner et al. |
| 9,452,287 B2 | 9/2016 | Rosenbluth et al. |
| 9,468,753 B2 | 10/2016 | Fisher et al. |
| 9,474,898 B2 | 10/2016 | Gozani et al. |
| 9,549,872 B2 | 1/2017 | Chen et al. |
| 9,550,068 B2 | 1/2017 | Weinstock |
| 9,581,972 B1 | 2/2017 | Arrow et al. |
| 9,586,038 B1 | 3/2017 | Kosierkiewicz |
| 9,589,698 B2 | 3/2017 | Anhalt et al. |
| 9,597,509 B2 | 3/2017 | Hoffer et al. |
| 9,610,442 B2 | 4/2017 | Yoo et al. |
| 9,610,459 B2 | 4/2017 | Burnett et al. |
| 9,615,797 B2 | 4/2017 | John |
| 9,630,004 B2 | 4/2017 | Rajguru et al. |
| 9,649,486 B2 | 5/2017 | Holzhacker |
| 9,656,070 B2 | 5/2017 | Gozani et al. |
| 9,669,211 B2 | 6/2017 | Wijting et al. |
| 9,675,800 B2 | 6/2017 | Li et al. |
| 9,675,801 B2 | 6/2017 | Kong et al. |
| 9,707,393 B2 | 7/2017 | Hsueh et al. |
| 9,731,126 B2 | 8/2017 | Ferree et al. |
| 9,757,584 B2 | 9/2017 | Burnett |
| 9,782,584 B2 | 10/2017 | Cartledge et al. |
| 9,802,041 B2 | 10/2017 | Wong et al. |
| 9,826,921 B2 | 11/2017 | Griffiths et al. |
| 9,861,283 B1 | 1/2018 | Giuffrida |
| 9,877,679 B1 | 1/2018 | Giuffrida |
| 9,877,680 B1 | 1/2018 | Giuffrida et al. |
| 9,884,179 B2 | 2/2018 | Bouton et al. |
| 9,924,899 B2 | 3/2018 | Pracar et al. |
| 9,956,395 B2 | 5/2018 | Bikson et al. |
| 9,974,478 B1 | 5/2018 | Brokaw et al. |
| 9,980,659 B2 | 5/2018 | Sadeghian-Motahar et al. |
| 9,992,918 B2 | 6/2018 | Watanabe et al. |
| 10,004,900 B2 | 6/2018 | Kent et al. |
| 10,016,600 B2 | 7/2018 | Creasey et al. |
| 10,022,545 B1 | 7/2018 | Giuffrida |
| 10,028,695 B2 | 7/2018 | Machado et al. |
| 10,045,740 B2 | 8/2018 | John |
| 10,046,161 B2 | 8/2018 | Biasiucci et al. |

(56)  References Cited

U.S. PATENT DOCUMENTS

| | | | |
|---|---|---|---|
| D828,351 S | 9/2018 | Xie et al. |
| 10,076,656 B2 | 9/2018 | Dar et al. |
| 10,080,885 B2 | 9/2018 | Nathan et al. |
| 10,085,670 B2 | 10/2018 | Crosson et al. |
| 10,112,040 B2 | 10/2018 | Herb et al. |
| 10,118,035 B2 | 11/2018 | Perez et al. |
| 10,118,049 B2 | 11/2018 | Matthews |
| 10,130,809 B2 | 11/2018 | Cartledge et al. |
| 10,130,810 B2 | 11/2018 | Ferree et al. |
| 10,137,025 B2 | 11/2018 | Fior et al. |
| 10,173,060 B2 | 1/2019 | Wong et al. |
| 10,179,238 B2 | 1/2019 | Wong et al. |
| 10,213,593 B2 | 2/2019 | Kaplan et al. |
| 10,213,602 B2 | 2/2019 | Ironi et al. |
| 10,232,174 B2 | 3/2019 | Simon et al. |
| 10,252,053 B2 | 4/2019 | Page et al. |
| 10,285,646 B1 | 5/2019 | Grant et al. |
| 10,286,210 B2 | 5/2019 | Yoo |
| 10,293,159 B2 | 5/2019 | Kong et al. |
| 10,335,594 B2 | 7/2019 | Lin et al. |
| 10,335,595 B2 | 7/2019 | Ferree et al. |
| 10,342,977 B2 | 7/2019 | Raghunathan |
| 10,398,896 B2 | 9/2019 | Lin et al. |
| 10,456,573 B1 | 10/2019 | Feinstein et al. |
| 10,463,854 B2 | 11/2019 | Perez |
| 10,499,848 B2 | 12/2019 | Weinstock |
| 10,500,396 B2 | 12/2019 | Tamaki et al. |
| 10,537,732 B2 | 1/2020 | Nachum et al. |
| 10,549,093 B2 | 2/2020 | Wong et al. |
| 10,556,107 B2 | 2/2020 | Yoo et al. |
| 10,561,839 B2 | 2/2020 | Wong et al. |
| 10,603,482 B2 | 3/2020 | Hamner et al. |
| 10,610,114 B2 | 4/2020 | Buckley et al. |
| 10,625,074 B2 | 4/2020 | Rosenbluth et al. |
| 10,632,312 B2 | 4/2020 | Ziv |
| 10,661,082 B2 | 5/2020 | Kerselaers |
| 10,716,941 B2 | 7/2020 | Yang et al. |
| 10,722,709 B2 | 7/2020 | Yoo et al. |
| 10,765,856 B2 | 9/2020 | Wong et al. |
| 10,773,079 B2 | 9/2020 | Keller et al. |
| 10,780,269 B2 | 9/2020 | Gozani et al. |
| 10,786,199 B1 | 9/2020 | Giuffrida et al. |
| 10,786,669 B2 | 9/2020 | Rajguru et al. |
| 10,814,130 B2 | 10/2020 | Wong et al. |
| 10,814,131 B2 | 10/2020 | Goldwasser et al. |
| D902,769 S | 11/2020 | Riot et al. |
| 10,835,736 B2 | 11/2020 | Horter et al. |
| 10,850,090 B2 | 12/2020 | Rosenbluth et al. |
| 10,870,002 B2 | 12/2020 | Wybo et al. |
| 10,905,879 B2 | 2/2021 | Wong et al. |
| 10,918,853 B2 | 2/2021 | Creasey et al. |
| 10,940,311 B2 | 3/2021 | Gozani et al. |
| 10,945,879 B2 | 3/2021 | Black et al. |
| 10,960,207 B2 | 3/2021 | Wong et al. |
| D915,399 S | 4/2021 | Chao et al. |
| 10,967,177 B2 | 4/2021 | Lee |
| 11,026,835 B2 | 6/2021 | Black et al. |
| 11,033,206 B2 | 6/2021 | Roh |
| 11,033,731 B2 | 6/2021 | Jeffery et al. |
| 11,033,736 B2 | 6/2021 | Edgerton et al. |
| 11,058,867 B2 | 7/2021 | Nathan et al. |
| 11,077,300 B2 | 8/2021 | McBride |
| 11,077,301 B2 | 8/2021 | Creasey et al. |
| 11,079,225 B2 | 8/2021 | Ong et al. |
| 11,103,699 B1 | 8/2021 | Oppenheim et al. |
| 11,141,586 B2 | 10/2021 | Campean et al. |
| 11,141,587 B2 | 10/2021 | Campean et al. |
| 11,160,971 B2 | 11/2021 | Sharma et al. |
| 11,166,632 B2 | 11/2021 | Grossman et al. |
| 11,197,999 B2 | 12/2021 | Crosson |
| 11,213,681 B2 | 1/2022 | Raghunathan |
| 11,224,742 B2 | 1/2022 | Burnett |
| 11,247,040 B2 | 2/2022 | Ferree et al. |
| 11,247,053 B2 | 2/2022 | Rajguru et al. |
| 11,266,836 B2 | 3/2022 | Charlesworth et al. |
| 11,278,724 B2 | 3/2022 | Law et al. |
| 11,318,307 B2 | 5/2022 | Kern et al. |
| 11,331,480 B2 | 5/2022 | Hamner et al. |
| 11,338,120 B2 | 5/2022 | Yun et al. |
| 11,338,128 B2 | 5/2022 | Lawson et al. |
| 11,344,722 B2 | 5/2022 | Wong et al. |
| 11,357,981 B2 | 6/2022 | Moaddeb et al. |
| 11,383,087 B1 | 7/2022 | Heldman et al. |
| 11,389,651 B2 | 7/2022 | Tamaki et al. |
| 11,419,515 B2 | 8/2022 | Crosson et al. |
| 11,420,052 B2 | 8/2022 | Doskocil et al. |
| 11,424,755 B2 | 8/2022 | Yang et al. |
| D962,929 S | 9/2022 | He et al. |
| 11,484,710 B2 | 11/2022 | Mantovani et al. |
| 11,504,530 B2 | 11/2022 | Herr et al. |
| 11,517,753 B2 | 12/2022 | Rhodes |
| 11,534,605 B2 | 12/2022 | Bouton et al. |
| 11,547,316 B2 | 1/2023 | Crosson et al. |
| 11,559,250 B1 | 1/2023 | Giuffrida et al. |
| 11,590,348 B2 | 2/2023 | Moaddeb et al. |
| 11,596,327 B2 | 3/2023 | Griffiths et al. |
| 11,596,785 B2 | 3/2023 | Hamner et al. |
| 11,596,791 B2 | 3/2023 | Wong et al. |
| 11,596,792 B2 | 3/2023 | Campean et al. |
| 11,623,078 B2 | 4/2023 | Simon et al. |
| 11,628,300 B2 | 4/2023 | Rajguru et al. |
| 11,642,513 B2 | 5/2023 | Sharma et al. |
| 11,666,758 B2 | 6/2023 | Crosson |
| 11,672,981 B2 | 6/2023 | Jaasma et al. |
| 11,717,682 B2 | 8/2023 | Gozani et al. |
| 11,744,482 B1 | 9/2023 | Giuffrida et al. |
| 11,759,642 B1 | 9/2023 | Heldman |
| 11,766,191 B2 | 9/2023 | Sharma et al. |
| 11,833,352 B2 | 12/2023 | Law et al. |
| 11,839,583 B1 | 12/2023 | Carballo et al. |
| 11,839,762 B2 | 12/2023 | Doskocil et al. |
| 11,844,943 B2 | 12/2023 | Rajguru et al. |
| 11,857,778 B2 | 1/2024 | Hamner et al. |
| 11,872,399 B2 | 1/2024 | Raghunathan |
| 11,878,166 B2 | 1/2024 | Colburn et al. |
| 11,890,468 B1 | 2/2024 | Yu |
| 11,890,469 B2 | 2/2024 | Moaddeb et al. |
| 11,896,824 B2 | 2/2024 | Doskocil |
| 11,911,604 B2 | 2/2024 | Sharma et al. |
| 11,911,605 B2 | 2/2024 | Crosson et al. |
| 11,911,609 B1 | 2/2024 | Heldman et al. |
| 11,918,806 B2 | 3/2024 | Wong et al. |
| 11,975,190 B2 | 5/2024 | Cho et al. |
| 11,986,317 B1 | 5/2024 | Heldman et al. |
| 11,992,685 B2 | 5/2024 | Kassiri Bidhendi et al. |
| 12,029,287 B2 | 7/2024 | Ye et al. |
| 12,083,334 B2 | 9/2024 | Burnett |
| 12,109,413 B2 | 10/2024 | Wong et al. |
| 12,157,001 B2 | 12/2024 | Wong et al. |
| 12,161,478 B1 | 12/2024 | Heldman et al. |
| 12,161,858 B2 | 12/2024 | Rosenbluth et al. |
| 12,161,865 B2 | 12/2024 | Hamner et al. |
| 12,179,012 B2 | 12/2024 | Simon et al. |
| 12,186,085 B2 | 1/2025 | Buckley et al. |
| 12,226,632 B2 | 2/2025 | Rajguru et al. |
| 12,237,121 B2 | 2/2025 | Ye et al. |
| D1,065,549 S | 3/2025 | Ye et al. |
| 12,251,560 B1 | 3/2025 | Blabaky et al. |
| 12,263,009 B1 | 4/2025 | Giuffrida et al. |
| 12,357,824 B2 | 7/2025 | Wong et al. |
| 12,420,082 B2 | 9/2025 | Hamner et al. |
| 12,453,853 B2 | 10/2025 | Rosenbluth et al. |
| 2001/0020177 A1 | 9/2001 | Gruzdowich et al. |
| 2002/0055761 A1 | 5/2002 | Mann et al. |
| 2002/0070252 A1 | 6/2002 | Bauer |
| 2002/0138116 A1 | 9/2002 | Bertolucci |
| 2002/0161415 A1 | 10/2002 | Cohen et al. |
| 2002/0165586 A1 | 11/2002 | Hill et al. |
| 2002/0177882 A1 | 11/2002 | DiLorenzo |
| 2003/0032992 A1 | 2/2003 | Thacker et al. |
| 2003/0045922 A1 | 3/2003 | Northrop |
| 2003/0088294 A1 | 5/2003 | Gesotti |
| 2003/0093098 A1 | 5/2003 | Heitzmann et al. |
| 2003/0100932 A1 | 5/2003 | Ciaff |

(56)     References Cited

U.S. PATENT DOCUMENTS

| | | |
|---|---|---|
| 2003/0149457 A1 | 8/2003 | Tcheng et al. |
| 2003/0181959 A1 | 9/2003 | Dobak, III |
| 2003/0187483 A1 | 10/2003 | Grey et al. |
| 2003/0195583 A1 | 10/2003 | Gruzdowich et al. |
| 2004/0015094 A1 | 1/2004 | Manabe et al. |
| 2004/0088025 A1 | 5/2004 | Gessotti |
| 2004/0093093 A1 | 5/2004 | Andrews |
| 2004/0102819 A1 | 5/2004 | Zou et al. |
| 2004/0111129 A1 | 6/2004 | Gliner et al. |
| 2004/0127939 A1 | 7/2004 | Grey et al. |
| 2004/0133249 A1 | 7/2004 | Gesotti |
| 2004/0167588 A1 | 8/2004 | Bertolucci |
| 2004/0249416 A1 | 12/2004 | Yun et al. |
| 2004/0267331 A1 | 12/2004 | Koeneman et al. |
| 2005/0015042 A1 | 1/2005 | Sun et al. |
| 2005/0021103 A1 | 1/2005 | DiLorenzo |
| 2005/0055063 A1 | 3/2005 | Loeb et al. |
| 2005/0060009 A1 | 3/2005 | Geotz |
| 2005/0065553 A1 | 3/2005 | Ben Ezra et al. |
| 2005/0075502 A1 | 4/2005 | Shafer |
| 2005/0171576 A1 | 8/2005 | Williams et al. |
| 2005/0171577 A1 | 8/2005 | Cohen et al. |
| 2005/0182454 A1 | 8/2005 | Gharib et al. |
| 2005/0222626 A1 | 10/2005 | DiLorenzo |
| 2005/0234309 A1 | 10/2005 | Klapper |
| 2005/0240241 A1 | 10/2005 | Yun et al. |
| 2005/0257349 A1 | 11/2005 | Bauer |
| 2005/0261559 A1 | 11/2005 | Mumford et al. |
| 2006/0015153 A1 | 1/2006 | Gliner et al. |
| 2006/0047326 A1* | 3/2006 | Wheeler ............ A61N 1/36014 607/48 |
| 2006/0052726 A1 | 3/2006 | Weisz et al. |
| 2006/0074450 A1 | 4/2006 | Boveja et al. |
| 2006/0095088 A1 | 5/2006 | De Ridder |
| 2006/0161218 A1 | 7/2006 | Danilov |
| 2006/0173509 A1 | 8/2006 | Lee et al. |
| 2006/0184059 A1 | 8/2006 | Jadidi |
| 2006/0217781 A1 | 9/2006 | John |
| 2006/0224191 A1 | 10/2006 | DiLorenzo |
| 2006/0229678 A1 | 10/2006 | Lee |
| 2006/0253167 A1 | 11/2006 | Kurtz et al. |
| 2006/0276853 A1 | 12/2006 | Tass |
| 2006/0293723 A1 | 12/2006 | Whitehurst et al. |
| 2007/0027486 A1 | 2/2007 | Armstrong |
| 2007/0073361 A1 | 3/2007 | Goren et al. |
| 2007/0123951 A1 | 5/2007 | Boston |
| 2007/0123952 A1 | 5/2007 | Strother et al. |
| 2007/0142862 A1 | 6/2007 | DiLorenzo |
| 2007/0142874 A1 | 6/2007 | John |
| 2007/0156179 A1 | 7/2007 | Karashurov |
| 2007/0156182 A1 | 7/2007 | Castel et al. |
| 2007/0156183 A1 | 7/2007 | Rhodes |
| 2007/0156200 A1 | 7/2007 | Kornet et al. |
| 2007/0173899 A1 | 7/2007 | Levin et al. |
| 2007/0173903 A1 | 7/2007 | Goren et al. |
| 2007/0203533 A1 | 8/2007 | Goren et al. |
| 2007/0203534 A1 | 8/2007 | Tapper |
| 2007/0207193 A1 | 9/2007 | Zasler et al. |
| 2007/0249952 A1 | 10/2007 | Rubin et al. |
| 2007/0255319 A1 | 11/2007 | Greenberg et al. |
| 2007/0256284 A1 | 11/2007 | Bauer |
| 2007/0276217 A1 | 11/2007 | Brown et al. |
| 2007/0282228 A1 | 12/2007 | Einav et al. |
| 2007/0293917 A1 | 12/2007 | Thompson et al. |
| 2007/0294746 A1 | 12/2007 | Sasakura et al. |
| 2008/0004672 A1 | 1/2008 | Dalal et al. |
| 2008/0009772 A1 | 1/2008 | Tyler et al. |
| 2008/0021505 A1 | 1/2008 | Hastings et al. |
| 2008/0027507 A1 | 1/2008 | Bijelic et al. |
| 2008/0030170 A1 | 2/2008 | Dacuay et al. |
| 2008/0033259 A1 | 2/2008 | Manto et al. |
| 2008/0033504 A1 | 2/2008 | Bertolucci |
| 2008/0033510 A1 | 2/2008 | Herregraven et al. |
| 2008/0033511 A1 | 2/2008 | Dobak |
| 2008/0051839 A1 | 2/2008 | Libbus et al. |
| 2008/0051845 A1 | 2/2008 | Mentelos |
| 2008/0058773 A1 | 3/2008 | John |
| 2008/0058871 A1 | 3/2008 | Libbus et al. |
| 2008/0058893 A1 | 3/2008 | Noujokat |
| 2008/0091256 A1 | 4/2008 | Libbus et al. |
| 2008/0097564 A1 | 4/2008 | Lathrop |
| 2008/0147146 A1 | 6/2008 | Wahlgren et al. |
| 2008/0177398 A1 | 7/2008 | Gross et al. |
| 2008/0195007 A1 | 8/2008 | Podrazhansky et al. |
| 2008/0208282 A1 | 8/2008 | Gelfand et al. |
| 2008/0208288 A1 | 8/2008 | Podrazhansky et al. |
| 2008/0216593 A1 | 9/2008 | Jacobsen et al. |
| 2008/0243204 A1 | 10/2008 | Uthman et al. |
| 2008/0269593 A1 | 10/2008 | Weinstock |
| 2008/0288016 A1 | 11/2008 | Amurthur et al. |
| 2008/0300449 A1 | 12/2008 | Gerber et al. |
| 2008/0306325 A1 | 12/2008 | Burnett et al. |
| 2008/0312520 A1 | 12/2008 | Rowlandson et al. |
| 2009/0018609 A1 | 1/2009 | DiLorenzo |
| 2009/0049722 A1 | 2/2009 | Chan |
| 2009/0076565 A1 | 3/2009 | Surwit |
| 2009/0082831 A1 | 3/2009 | Paul et al. |
| 2009/0099623 A1 | 4/2009 | Bentwich |
| 2009/0105785 A1 | 4/2009 | Wei et al. |
| 2009/0112133 A1 | 4/2009 | Deisseroth et al. |
| 2009/0157138 A1 | 6/2009 | Errico et al. |
| 2009/0187121 A1 | 7/2009 | Evans |
| 2009/0216294 A1 | 8/2009 | Ewing et al. |
| 2009/0222053 A1 | 9/2009 | Gaunt et al. |
| 2009/0247910 A1 | 10/2009 | Klapper |
| 2009/0249617 A1 | 10/2009 | Karicherla et al. |
| 2009/0270952 A1 | 10/2009 | Weinstock |
| 2009/0299435 A1 | 12/2009 | Gliner et al. |
| 2009/0312690 A1 | 12/2009 | Kim et al. |
| 2009/0318986 A1 | 12/2009 | Alo et al. |
| 2009/0326595 A1 | 12/2009 | Brockway et al. |
| 2009/0326607 A1 | 12/2009 | Castel et al. |
| 2010/0004715 A1 | 1/2010 | Fahey |
| 2010/0010381 A1 | 1/2010 | Skelton et al. |
| 2010/0010383 A1 | 1/2010 | Skelton et al. |
| 2010/0010572 A1 | 1/2010 | Skelton et al. |
| 2010/0036464 A1 | 2/2010 | Picciano |
| 2010/0057154 A1 | 3/2010 | Dietrich et al. |
| 2010/0059722 A1 | 3/2010 | Copp-Howland et al. |
| 2010/0072046 A1 | 3/2010 | Maeda et al. |
| 2010/0076533 A1 | 3/2010 | Dar et al. |
| 2010/0099963 A1 | 4/2010 | Kilger |
| 2010/0107657 A1 | 5/2010 | Vistakula |
| 2010/0125220 A1 | 5/2010 | Seong |
| 2010/0152623 A1 | 6/2010 | Williams |
| 2010/0152817 A1 | 6/2010 | Gillbe |
| 2010/0168501 A1 | 7/2010 | Burnett et al. |
| 2010/0168604 A1 | 7/2010 | Echauz |
| 2010/0174342 A1 | 7/2010 | Boston et al. |
| 2010/0202172 A1 | 8/2010 | Skirda et al. |
| 2010/0222629 A1 | 9/2010 | Burnett et al. |
| 2010/0222630 A1 | 9/2010 | Mangrum et al. |
| 2010/0227330 A1 | 9/2010 | Fink et al. |
| 2010/0228180 A1 | 9/2010 | Jayes et al. |
| 2010/0249637 A1 | 9/2010 | Walter et al. |
| 2010/0292527 A1 | 11/2010 | Schneider et al. |
| 2010/0298905 A1 | 11/2010 | Simon |
| 2010/0324611 A1 | 12/2010 | Deming et al. |
| 2011/0004268 A1 | 1/2011 | Tcheng et al. |
| 2011/0009920 A1 | 1/2011 | Whitehurst et al. |
| 2011/0021899 A1 | 1/2011 | Arps et al. |
| 2011/0040204 A1 | 2/2011 | Ivorra et al. |
| 2011/0040288 A1 | 2/2011 | Eckstein et al. |
| 2011/0054358 A1 | 3/2011 | Kim et al. |
| 2011/0071590 A1 | 3/2011 | Mounaim et al. |
| 2011/0082524 A1 | 4/2011 | Thomas et al. |
| 2011/0098780 A1 | 4/2011 | Graupe et al. |
| 2011/0112605 A1 | 5/2011 | Fahey |
| 2011/0118805 A1 | 5/2011 | Wei et al. |
| 2011/0125212 A1 | 5/2011 | Tyler |
| 2011/0137375 A1 | 6/2011 | McBride |
| 2011/0184489 A1 | 7/2011 | Nicolelis et al. |
| 2011/0196446 A1 | 8/2011 | Wu |
| 2011/0202107 A1 | 8/2011 | Sunagawa et al. |

(56)                    References Cited

U.S. PATENT DOCUMENTS

| | | |
|---|---|---|
| 2011/0208444 A1 | 8/2011 | Solinky |
| 2011/0213278 A1 | 9/2011 | Horak et al. |
| 2011/0224571 A1 | 9/2011 | Pascual-Leone et al. |
| 2011/0230701 A1 | 9/2011 | Simon et al. |
| 2011/0245734 A1 | 10/2011 | Wagner et al. |
| 2011/0250297 A1 | 10/2011 | Oronsky et al. |
| 2011/0282412 A1 | 11/2011 | Glukhovsky et al. |
| 2011/0288615 A1 | 11/2011 | Armstrong et al. |
| 2011/0301663 A1 | 12/2011 | Wang et al. |
| 2012/0010492 A1 | 1/2012 | Thramann et al. |
| 2012/0035674 A1 | 2/2012 | Weinstock |
| 2012/0035680 A1 | 2/2012 | Napadow |
| 2012/0046535 A1 | 2/2012 | Lin et al. |
| 2012/0050298 A1 | 3/2012 | Hoffman |
| 2012/0053491 A1 | 3/2012 | Nathan et al. |
| 2012/0059298 A1 | 3/2012 | Hoffman et al. |
| 2012/0078319 A1 | 3/2012 | De Ridder |
| 2012/0088986 A1 | 4/2012 | David et al. |
| 2012/0092178 A1 | 4/2012 | Callsen et al. |
| 2012/0098493 A1 | 4/2012 | Budike |
| 2012/0101326 A1 | 4/2012 | Simon et al. |
| 2012/0109013 A1 | 5/2012 | Everett et al. |
| 2012/0136410 A1 | 5/2012 | Rezai et al. |
| 2012/0158094 A1 | 6/2012 | Kramer et al. |
| 2012/0184801 A1 | 7/2012 | Simon et al. |
| 2012/0185020 A1 | 7/2012 | Simon et al. |
| 2012/0186121 A1 | 7/2012 | Hanssen et al. |
| 2012/0203079 A1 | 8/2012 | Mclaughlin |
| 2012/0203245 A1 | 8/2012 | Imabayashi et al. |
| 2012/0211013 A1 | 8/2012 | Otis |
| 2012/0220812 A1 | 8/2012 | Mishelevich |
| 2012/0239112 A1 | 9/2012 | Muraoka |
| 2012/0245483 A1 | 9/2012 | Lundqvist |
| 2012/0259255 A1 | 10/2012 | Tomlinson et al. |
| 2012/0277621 A1 | 11/2012 | Gerber et al. |
| 2012/0289869 A1 | 11/2012 | Tyler |
| 2012/0290036 A1 | 11/2012 | Karamanoglu et al. |
| 2012/0302821 A1 | 11/2012 | Burnett |
| 2012/0303080 A1 | 11/2012 | Ben-David et al. |
| 2012/0310298 A1 | 12/2012 | Besio et al. |
| 2012/0310299 A1 | 12/2012 | Norbert et al. |
| 2012/0310303 A1 | 12/2012 | Popovic et al. |
| 2012/0330182 A1 | 12/2012 | Alberts et al. |
| 2013/0006322 A1 | 1/2013 | Tai |
| 2013/0035745 A1 | 2/2013 | Ahmed et al. |
| 2013/0053817 A1 | 2/2013 | Yun et al. |
| 2013/0060124 A1 | 3/2013 | Zietsma |
| 2013/0066388 A1 | 3/2013 | Bernhard et al. |
| 2013/0066395 A1 | 3/2013 | Simon et al. |
| 2013/0085317 A1 | 4/2013 | Feinstein |
| 2013/0090519 A1 | 4/2013 | Tass |
| 2013/0106684 A1 | 5/2013 | Weast et al. |
| 2013/0116606 A1 | 5/2013 | Cordo |
| 2013/0123568 A1 | 5/2013 | Hamilton et al. |
| 2013/0123666 A1 | 5/2013 | Giuffrida et al. |
| 2013/0131484 A1 | 5/2013 | Pernu |
| 2013/0131770 A1 | 5/2013 | Rezai |
| 2013/0158624 A1 | 6/2013 | Bain et al. |
| 2013/0158627 A1 | 6/2013 | Gozani et al. |
| 2013/0178765 A1 | 7/2013 | Mishelevich |
| 2013/0211471 A1 | 8/2013 | Libbus et al. |
| 2013/0231713 A1 | 9/2013 | De Ridder et al. |
| 2013/0236867 A1 | 9/2013 | Avni et al. |
| 2013/0238049 A1 | 9/2013 | Simon et al. |
| 2013/0245486 A1 | 9/2013 | Simon et al. |
| 2013/0245713 A1 | 9/2013 | Tass |
| 2013/0253299 A1 | 9/2013 | Weber et al. |
| 2013/0262298 A1 | 10/2013 | Morley |
| 2013/0267759 A1 | 10/2013 | Jin |
| 2013/0281890 A1 | 10/2013 | Mishelevich |
| 2013/0289647 A1 | 10/2013 | Bhadra et al. |
| 2013/0296967 A1 | 11/2013 | Skaribas et al. |
| 2013/0297022 A1 | 11/2013 | Pathak |
| 2013/0317565 A1 | 11/2013 | Weinstock |
| 2013/0331907 A1 | 12/2013 | Sumners et al. |
| 2013/0333094 A1 | 12/2013 | Rogers et al. |
| 2013/0338726 A1 | 12/2013 | Machado |
| 2014/0025059 A1 | 1/2014 | Kerr |
| 2014/0031605 A1 | 1/2014 | Schneider |
| 2014/0039573 A1 | 2/2014 | Jindra |
| 2014/0039575 A1 | 2/2014 | Bradley |
| 2014/0046406 A1 | 2/2014 | Ellrich et al. |
| 2014/0046407 A1 | 2/2014 | Ben-Ezra et al. |
| 2014/0046423 A1 | 2/2014 | Rajguru et al. |
| 2014/0058189 A1 | 2/2014 | Stubbeman |
| 2014/0067003 A1 | 3/2014 | Vase et al. |
| 2014/0078694 A1 | 3/2014 | Wissmar |
| 2014/0081345 A1 | 3/2014 | Hershey |
| 2014/0081353 A1 | 3/2014 | Cook et al. |
| 2014/0094675 A1 | 4/2014 | Luna et al. |
| 2014/0094873 A1 | 4/2014 | Emborg et al. |
| 2014/0114117 A1 | 4/2014 | Naghavi et al. |
| 2014/0128939 A1 | 5/2014 | Embrey et al. |
| 2014/0132410 A1 | 5/2014 | Chang |
| 2014/0142654 A1 | 5/2014 | Simon et al. |
| 2014/0148872 A1 | 5/2014 | Goldwasser et al. |
| 2014/0148873 A1 | 5/2014 | Kirn |
| 2014/0163444 A1 | 6/2014 | Ingvarsson |
| 2014/0171834 A1 | 6/2014 | DeGoede et al. |
| 2014/0200573 A1 | 7/2014 | Deem et al. |
| 2014/0214119 A1 | 7/2014 | Greiner et al. |
| 2014/0228927 A1 | 8/2014 | Ahmad et al. |
| 2014/0236258 A1 | 8/2014 | Carroll et al. |
| 2014/0246628 A1 | 9/2014 | Anhalt et al. |
| 2014/0249452 A1 | 9/2014 | Marsh et al. |
| 2014/0257047 A1 | 9/2014 | Sillay et al. |
| 2014/0257129 A1 | 9/2014 | Choi et al. |
| 2014/0276194 A1 | 9/2014 | Osorio |
| 2014/0277220 A1 | 9/2014 | Brennan et al. |
| 2014/0296752 A1 | 10/2014 | Edgerton et al. |
| 2014/0296934 A1 | 10/2014 | Gozani et al. |
| 2014/0296935 A1 | 10/2014 | Ferree et al. |
| 2014/0300490 A1 | 10/2014 | Kotz et al. |
| 2014/0309709 A1 | 10/2014 | Gozani et al. |
| 2014/0316484 A1 | 10/2014 | Edgerton et al. |
| 2014/0324118 A1 | 10/2014 | Simon et al. |
| 2014/0330068 A1 | 11/2014 | Partsch et al. |
| 2014/0330335 A1 | 11/2014 | Errico et al. |
| 2014/0336003 A1 | 11/2014 | Franz et al. |
| 2014/0336722 A1 | 11/2014 | Rocon De Lima et al. |
| 2014/0336731 A1 | 11/2014 | Weinstock |
| 2014/0343462 A1 | 11/2014 | Burnet |
| 2014/0350436 A1 | 11/2014 | Nathan et al. |
| 2014/0358040 A1 | 12/2014 | Kim et al. |
| 2014/0364678 A1 | 12/2014 | Harry et al. |
| 2015/0004656 A1 | 1/2015 | Tang et al. |
| 2015/0005852 A1 | 1/2015 | Hershey et al. |
| 2015/0012067 A1 | 1/2015 | Bradley et al. |
| 2015/0018926 A1 | 1/2015 | Frenkel et al. |
| 2015/0026783 A1 | 1/2015 | Tseng et al. |
| 2015/0038886 A1 | 2/2015 | Snow |
| 2015/0042315 A1 | 2/2015 | Cen et al. |
| 2015/0044656 A1 | 2/2015 | Eichhorn et al. |
| 2015/0057506 A1 | 2/2015 | Luna et al. |
| 2015/0073310 A1 | 3/2015 | Pracar et al. |
| 2015/0080979 A1 | 3/2015 | Lasko et al. |
| 2015/0097617 A1 | 4/2015 | Chak |
| 2015/0100004 A1 | 4/2015 | Goldman et al. |
| 2015/0100104 A1 | 4/2015 | Kiani et al. |
| 2015/0100105 A1 | 4/2015 | Kiani et al. |
| 2015/0148865 A1 | 5/2015 | Gozani et al. |
| 2015/0148866 A1 | 5/2015 | Bulsen et al. |
| 2015/0148878 A1 | 5/2015 | Yoo et al. |
| 2015/0157274 A1 | 6/2015 | Ghassemzadeh et al. |
| 2015/0163873 A1 | 6/2015 | Kawai et al. |
| 2015/0164377 A1 | 6/2015 | Nathan et al. |
| 2015/0164401 A1 | 6/2015 | Toth et al. |
| 2015/0190085 A1 | 7/2015 | Nathan et al. |
| 2015/0190634 A1 | 7/2015 | Rezai et al. |
| 2015/0196767 A1 | 7/2015 | Zaghloul |
| 2015/0202444 A1 | 7/2015 | Franke et al. |
| 2015/0208955 A1 | 7/2015 | Smith |
| 2015/0216475 A1 | 8/2015 | Luna et al. |
| 2015/0230733 A1 | 8/2015 | Heo et al. |

(56)     References Cited

U.S. PATENT DOCUMENTS

| | | |
|---|---|---|
| 2015/0230756 A1 | 8/2015 | Luna et al. |
| 2015/0273234 A1 | 10/2015 | Weinstock |
| 2015/0277559 A1 | 10/2015 | Vescovi et al. |
| 2015/0297901 A1 | 10/2015 | Kockx |
| 2015/0321000 A1 | 11/2015 | Rosenbluth et al. |
| 2015/0335882 A1 | 11/2015 | Gross |
| 2015/0360030 A1 | 12/2015 | Cartledge et al. |
| 2016/0001096 A1 | 1/2016 | Mishelevich |
| 2016/0008620 A1 | 1/2016 | Stubbeman |
| 2016/0016014 A1 | 1/2016 | Wagner et al. |
| 2016/0022987 A1 | 1/2016 | Zschaeck et al. |
| 2016/0022989 A1 | 1/2016 | Pfeifer |
| 2016/0038059 A1 | 2/2016 | Asada et al. |
| 2016/0039239 A1 | 2/2016 | Ward et al. |
| 2016/0045140 A1 | 2/2016 | Kitamura et al. |
| 2016/0089045 A1 | 3/2016 | Sadeghian-Motahar et al. |
| 2016/0106344 A1 | 4/2016 | Nazari |
| 2016/0120432 A1 | 5/2016 | Sridhar et al. |
| 2016/0121110 A1 | 5/2016 | Kent et al. |
| 2016/0128621 A1 | 5/2016 | Machado et al. |
| 2016/0129248 A1 | 5/2016 | Creasey et al. |
| 2016/0144186 A1 | 5/2016 | Kaemmerer et al. |
| 2016/0156261 A1 | 6/2016 | Kaneda |
| 2016/0157735 A1 | 6/2016 | Zhang |
| 2016/0158542 A1 | 6/2016 | Ahmed |
| 2016/0158565 A1 | 6/2016 | Lee |
| 2016/0198998 A1 | 7/2016 | Rahimi et al. |
| 2016/0213924 A1 | 7/2016 | Coleman et al. |
| 2016/0220836 A1 | 8/2016 | Parks |
| 2016/0233034 A1 | 8/2016 | Sheng |
| 2016/0242656 A1 | 8/2016 | Jackson et al. |
| 2016/0262685 A1 | 9/2016 | Wagner et al. |
| 2016/0263376 A1 | 9/2016 | Yoo et al. |
| 2016/0279435 A1 | 9/2016 | Hyde et al. |
| 2016/0287879 A1 | 10/2016 | Denison et al. |
| 2016/0336722 A1 | 11/2016 | Taxter |
| 2016/0339239 A1 | 11/2016 | Yoo et al. |
| 2016/0361540 A9 | 12/2016 | Simon et al. |
| 2016/0375249 A1 | 12/2016 | Bonnet et al. |
| 2017/0014625 A1 | 1/2017 | Rosenbluth et al. |
| 2017/0027812 A1 | 2/2017 | Hyde et al. |
| 2017/0036025 A1 | 2/2017 | Sachs et al. |
| 2017/0042467 A1 | 2/2017 | Herr et al. |
| 2017/0055880 A1 | 3/2017 | Agrawal et al. |
| 2017/0056238 A1 | 3/2017 | Yi et al. |
| 2017/0056643 A1 | 3/2017 | Herb et al. |
| 2017/0079597 A1 | 3/2017 | Horne |
| 2017/0080207 A1 | 3/2017 | Perez et al. |
| 2017/0087364 A1 | 3/2017 | Cartledge et al. |
| 2017/0095667 A1 | 4/2017 | Yakovlev et al. |
| 2017/0113045 A1 | 4/2017 | Baldassano et al. |
| 2017/0132067 A1 | 5/2017 | Singaravelu Vanaja et al. |
| 2017/0157398 A1 | 6/2017 | Wong et al. |
| 2017/0165485 A1 | 6/2017 | Sullivan et al. |
| 2017/0224991 A1 | 8/2017 | Wingeier et al. |
| 2017/0239415 A1 | 8/2017 | Hwang et al. |
| 2017/0246481 A1 | 8/2017 | Mishelevich |
| 2017/0259061 A1 | 9/2017 | Simon et al. |
| 2017/0266443 A1 | 9/2017 | Rajguru et al. |
| 2017/0274208 A1 | 9/2017 | Nagel et al. |
| 2017/0287146 A1 | 10/2017 | Pathak et al. |
| 2017/0312505 A1 | 11/2017 | Ahmed |
| 2017/0312512 A1 | 11/2017 | Creasey et al. |
| 2017/0312513 A1 | 11/2017 | Hershey et al. |
| 2017/0361093 A1 | 12/2017 | Yoo et al. |
| 2017/0368329 A1 | 12/2017 | Tyler et al. |
| 2018/0001086 A1 | 1/2018 | Bartholomew et al. |
| 2018/0001088 A1 | 1/2018 | Tass |
| 2018/0021576 A1 | 1/2018 | Wong et al. |
| 2018/0028841 A1 | 2/2018 | Konofagou et al. |
| 2018/0036535 A1 | 2/2018 | Wong et al. |
| 2018/0042654 A1 | 2/2018 | Ingvarsson et al. |
| 2018/0049676 A1 | 2/2018 | Griffiths et al. |
| 2018/0064344 A1 | 3/2018 | Nguyen |
| 2018/0064362 A1 | 3/2018 | Hennings et al. |
| 2018/0064944 A1 | 3/2018 | Grill et al. |
| 2018/0116546 A1 | 5/2018 | Pastoor et al. |
| 2018/0132757 A1 | 5/2018 | Kong et al. |
| 2018/0140842 A1 | 5/2018 | Olaighin et al. |
| 2018/0168905 A1 | 6/2018 | Goodall et al. |
| 2018/0169400 A1 | 6/2018 | Wong et al. |
| 2018/0199841 A1 | 7/2018 | Yang et al. |
| 2018/0214694 A1 | 8/2018 | Parramon |
| 2018/0221620 A1 | 8/2018 | Metzger |
| 2018/0235500 A1 | 8/2018 | Lee et al. |
| 2018/0236217 A1 | 8/2018 | Hamner et al. |
| 2018/0264263 A1 | 9/2018 | Rosenbluth et al. |
| 2018/0289965 A1 | 10/2018 | Nelson et al. |
| 2018/0345020 A1 | 12/2018 | Ironi et al. |
| 2019/0001117 A1 | 1/2019 | Ben-David et al. |
| 2019/0001129 A1 | 1/2019 | Rosenbluth et al. |
| 2019/0001139 A1 | 1/2019 | Mishra et al. |
| 2019/0126047 A1 | 5/2019 | Kassiri Bidhendi et al. |
| 2019/0134393 A1 | 5/2019 | Wong et al. |
| 2019/0143098 A1 | 5/2019 | Kaplan et al. |
| 2019/0143111 A1 | 5/2019 | Hamner et al. |
| 2019/0143113 A1 | 5/2019 | Wong et al. |
| 2019/0167976 A1 | 6/2019 | Byers et al. |
| 2019/0229727 A1 | 7/2019 | Krishna |
| 2019/0269914 A1 | 9/2019 | Moaddeb et al. |
| 2019/0298998 A1 | 10/2019 | Coleman et al. |
| 2019/0299008 A1* | 10/2019 | Rao ...................... G06N 3/045 |
| 2019/0321636 A1 | 10/2019 | Law et al. |
| 2019/0343462 A1 | 11/2019 | Grant et al. |
| 2019/0374771 A1 | 12/2019 | Simon et al. |
| 2020/0023183 A1 | 1/2020 | Ollerenshaw et al. |
| 2020/0038654 A1 | 2/2020 | Doskocil et al. |
| 2020/0046968 A1 | 2/2020 | Herr et al. |
| 2020/0061378 A1 | 2/2020 | Ganguly et al. |
| 2020/0069947 A1 | 3/2020 | Kent |
| 2020/0077943 A1 | 3/2020 | Weinstock |
| 2020/0093400 A1 | 3/2020 | Hamner et al. |
| 2020/0139118 A1 | 5/2020 | John et al. |
| 2020/0147373 A1 | 5/2020 | Tamaki et al. |
| 2020/0155847 A1 | 5/2020 | Perez |
| 2020/0171269 A1 | 6/2020 | Hooper et al. |
| 2020/0171304 A1 | 6/2020 | Simon et al. |
| 2020/0179687 A1 | 6/2020 | Wong et al. |
| 2020/0197707 A1 | 6/2020 | Covalin |
| 2020/0204164 A1 | 6/2020 | Nishiyama |
| 2020/0215324 A1 | 7/2020 | Mantovani et al. |
| 2020/0221975 A1 | 7/2020 | Basta et al. |
| 2020/0254247 A1 | 8/2020 | Brezel et al. |
| 2020/0254251 A1 | 8/2020 | Wong et al. |
| 2020/0269046 A1 | 8/2020 | Page et al. |
| 2020/0276442 A1 | 9/2020 | Owen |
| 2020/0282201 A1 | 9/2020 | Doskocil |
| 2020/0289813 A1 | 9/2020 | Ito et al. |
| 2020/0289814 A1 | 9/2020 | Hamner et al. |
| 2020/0297999 A1 | 9/2020 | Pal |
| 2020/0316379 A1 | 10/2020 | Yoo et al. |
| 2020/0324104 A1 | 10/2020 | Labuschagne et al. |
| 2020/0338348 A1 | 10/2020 | Honeycutt et al. |
| 2020/0346008 A1 | 11/2020 | Song |
| 2020/0367775 A1 | 11/2020 | Buckley et al. |
| 2020/0405188 A1 | 12/2020 | Sharma et al. |
| 2020/0406022 A1 | 12/2020 | Sharma et al. |
| 2021/0008369 A1 | 1/2021 | Crosson |
| 2021/0016079 A1 | 1/2021 | Ekelem et al. |
| 2021/0016089 A1 | 1/2021 | Crosson |
| 2021/0023376 A1* | 1/2021 | Hareland ............ A61N 1/3704 |
| 2021/0031026 A1 | 2/2021 | Simon et al. |
| 2021/0031036 A1 | 2/2021 | Sharma et al. |
| 2021/0052883 A1 | 2/2021 | Wong et al. |
| 2021/0052897 A1 | 2/2021 | Bhadra et al. |
| 2021/0052900 A1 | 2/2021 | Pepin et al. |
| 2021/0060337 A1 | 3/2021 | Wybo et al. |
| 2021/0069507 A1 | 3/2021 | Gozani et al. |
| 2021/0085974 A1 | 3/2021 | Bouton et al. |
| 2021/0085976 A1 | 3/2021 | Heldman et al. |
| 2021/0099867 A1 | 4/2021 | Brown et al. |
| 2021/0100999 A1 | 4/2021 | Rosenbluth et al. |
| 2021/0101007 A1 | 4/2021 | Hamner et al. |
| 2021/0113834 A1 | 4/2021 | Wong et al. |

(56)             References Cited

U.S. PATENT DOCUMENTS

| | | |
|---|---|---|
| 2021/0162212 A1 | 6/2021 | Kern et al. |
| 2021/0169684 A1 | 6/2021 | Black et al. |
| 2021/0187279 A1 | 6/2021 | Bouton et al. |
| 2021/0205619 A1 | 7/2021 | Wong et al. |
| 2021/0212230 A1 | 7/2021 | Hsu et al. |
| 2021/0213283 A1 | 7/2021 | Yoo et al. |
| 2021/0220650 A1 | 7/2021 | Kassiri Bidhendi et al. |
| 2021/0244940 A1 | 8/2021 | Liberatore et al. |
| 2021/0244950 A1 | 8/2021 | Ironi et al. |
| 2021/0248893 A1 | 8/2021 | Van Dinther |
| 2021/0252278 A1 | 8/2021 | Hamner et al. |
| 2021/0252279 A1 | 8/2021 | Kong et al. |
| 2021/0260379 A1 | 8/2021 | Charlesworth et al. |
| 2021/0266011 A1 | 8/2021 | Chen et al. |
| 2021/0283400 A1 | 9/2021 | Hamner et al. |
| 2021/0289814 A1 | 9/2021 | Roubos-van den Hil et al. |
| 2021/0299445 A1 | 9/2021 | Rajguru et al. |
| 2021/0308460 A1 | 10/2021 | Wong et al. |
| 2021/0330547 A1 | 10/2021 | Moaddeb et al. |
| 2021/0330974 A1 | 10/2021 | Wong et al. |
| 2021/0353181 A1 | 11/2021 | Roh |
| 2021/0379374 A1 | 12/2021 | Hamner et al. |
| 2021/0379379 A1 | 12/2021 | Campean et al. |
| 2021/0402172 A1 | 12/2021 | Ross et al. |
| 2022/0001164 A1 | 1/2022 | Sharma et al. |
| 2022/0016413 A1 | 1/2022 | John et al. |
| 2022/0031245 A1 | 2/2022 | Bresler |
| 2022/0054820 A1 | 2/2022 | Turner |
| 2022/0054831 A1 | 2/2022 | McBride |
| 2022/0080196 A1 | 3/2022 | Crosson |
| 2022/0088373 A1 | 3/2022 | Burnett |
| 2022/0126095 A1 | 4/2022 | Rajguru et al. |
| 2022/0143391 A1 | 5/2022 | Vaishya et al. |
| 2022/0143392 A1 | 5/2022 | Labuschagne et al. |
| 2022/0143393 A1 | 5/2022 | Charlesworth et al. |
| 2022/0143402 A1 | 5/2022 | Oppenheim et al. |
| 2022/0203091 A1 | 6/2022 | Vysokov |
| 2022/0212007 A1 | 7/2022 | Rajguru et al. |
| 2022/0218991 A1 | 7/2022 | Moaddeb et al. |
| 2022/0220276 A1 | 7/2022 | Ziebell et al. |
| 2022/0233860 A1 | 7/2022 | Hamner et al. |
| 2022/0266011 A1 | 8/2022 | Hamner et al. |
| 2022/0266012 A1 | 8/2022 | Hamner et al. |
| 2022/0273938 A1 | 9/2022 | Chen |
| 2022/0347461 A1 | 11/2022 | Campean et al. |
| 2022/0401721 A1 | 12/2022 | Jackson et al. |
| 2022/0409404 A1 | 12/2022 | Yang et al. |
| 2023/0009158 A1 | 1/2023 | Liberatore |
| 2023/0010696 A1 | 1/2023 | Pradeep |
| 2023/0062326 A1 | 3/2023 | Colachis et al. |
| 2023/0074017 A1 | 3/2023 | Pan |
| 2023/0075750 A1 | 3/2023 | Pan |
| 2023/0080790 A1 | 3/2023 | Crosson et al. |
| 2023/0086004 A1 | 3/2023 | Yang et al. |
| 2023/0110185 A1 | 4/2023 | Mantovani et al. |
| 2023/0191115 A1 | 6/2023 | Blum et al. |
| 2023/0191126 A1 | 6/2023 | Kent et al. |
| 2023/0200732 A1 | 6/2023 | Ye et al. |
| 2023/0201584 A1 | 6/2023 | Rajguru et al. |
| 2023/0207232 A1 | 6/2023 | Ye et al. |
| 2023/0218897 A1 | 7/2023 | Wang et al. |
| 2023/0233855 A1 | 7/2023 | Sunkeri et al. |
| 2023/0248962 A1 | 8/2023 | Zhang et al. |
| 2023/0256245 A1 | 8/2023 | Crosson |
| 2023/0277109 A1 | 9/2023 | Blum et al. |
| 2023/0277841 A1 | 9/2023 | Wang et al. |
| 2023/0285743 A1 | 9/2023 | Muccio |
| 2023/0293882 A1 | 9/2023 | Howe |
| 2023/0321430 A1 | 10/2023 | Ye et al. |
| 2023/0371846 A1 | 11/2023 | Sharma et al. |
| 2023/0381505 A1 | 11/2023 | Gozani et al. |
| 2024/0032819 A1 | 2/2024 | Zhao et al. |
| 2024/0058606 A1 | 2/2024 | Law et al. |
| 2024/0066286 A1 | 2/2024 | Yin et al. |
| 2024/0066287 A1 | 2/2024 | Siff |

| | | |
|---|---|---|
| 2024/0090600 A1 | 3/2024 | Colachis et al. |
| 2024/0108239 A1 | 4/2024 | Crosson et al. |
| 2024/0122797 A1 | 4/2024 | Moaddeb et al. |
| 2024/0123230 A1 | 4/2024 | Raghunathan |
| 2024/0157142 A1 | 5/2024 | Yeniel et al. |
| 2024/0189594 A1 | 6/2024 | Hamner et al. |
| 2024/0197237 A1 | 6/2024 | Hamner et al. |
| 2024/0226550 A1 | 7/2024 | Moaddeb et al. |
| 2024/0245388 A1 | 7/2024 | Plunger |
| 2024/0299734 A1 | 9/2024 | Wang et al. |
| 2024/0299735 A1 | 9/2024 | Wang et al. |
| 2024/0316339 A1 | 9/2024 | Keefer et al. |
| 2024/0325727 A1 | 10/2024 | Hamner et al. |
| 2024/0325728 A1 | 10/2024 | Schulte et al. |
| 2024/0335654 A1 | 10/2024 | Schulte et al. |
| 2024/0386553 A1 | 11/2024 | Akakin et al. |
| 2024/0406000 A1 | 12/2024 | Nguyen et al. |
| 2024/0428429 A1 | 12/2024 | Akakin et al. |
| 2025/0018185 A1 | 1/2025 | Ye et al. |
| 2025/0082924 A1 | 3/2025 | Simon et al. |
| 2025/0128058 A1 | 4/2025 | Hamner et al. |
| 2025/0135189 A1 | 5/2025 | Wong et al. |
| 2025/0135200 A1 | 5/2025 | Wong et al. |
| 2025/0161663 A1 | 5/2025 | Rosenbluth et al. |
| 2025/0161664 A1 | 5/2025 | Wong et al. |
| 2025/0161665 A1 | 5/2025 | Liberatore et al. |
| 2025/0161684 A1 | 5/2025 | Hamner et al. |
| 2025/0161685 A1 | 5/2025 | Hamner et al. |
| 2025/0170399 A1 | 5/2025 | Wong et al. |
| 2025/0195877 A1 | 6/2025 | Schulte et al. |
| 2025/0262430 A1 | 8/2025 | Ross et al. |
| 2025/0281735 A1 | 9/2025 | Yang |
| 2025/0332415 A1 | 10/2025 | Kent et al. |
| 2025/0339671 A1 | 11/2025 | Wong et al. |
| 2025/0339672 A1 | 11/2025 | Wong et al. |
| 2025/0339685 A1 | 11/2025 | Wong et al. |
| 2025/0345593 A1 | 11/2025 | Rosenbluth et al. |
| 2025/0345594 A1 | 11/2025 | Rosenbluth et al. |

FOREIGN PATENT DOCUMENTS

| | | |
|---|---|---|
| CN | 1826154 | 8/2006 |
| CN | 101022849 | 8/2007 |
| CN | 101115524 | 1/2008 |
| CN | 101365373 | 2/2009 |
| CN | 101612043 | 12/2009 |
| CN | 101687093 | 3/2010 |
| CN | 101801453 | 8/2010 |
| CN | 102089031 | 6/2011 |
| CN | 102481394 | 5/2012 |
| CN | 102905757 | 1/2013 |
| CN | 202724457 | 2/2013 |
| CN | 103517732 | 1/2014 |
| CN | 103608069 | 2/2014 |
| CN | 103889503 | 6/2014 |
| CN | 104144729 | 11/2014 |
| CN | 104168951 | 11/2014 |
| CN | 104436431 | 3/2015 |
| CN | 104519960 | 4/2015 |
| CN | 104939815 | 9/2015 |
| CN | 105457158 | 4/2016 |
| CN | 105848710 | 8/2016 |
| CN | 106413805 | 2/2017 |
| CN | 106687161 | 5/2017 |
| CN | 106794347 | 5/2017 |
| CN | 107949421 | 4/2018 |
| CN | 108697890 | 10/2018 |
| CN | 111358461 | 7/2020 |
| DE | 10 2008042373 | 4/2010 |
| DE | 10 2009004011 | 7/2010 |
| EP | 0000759 | 2/1979 |
| EP | 0801957 | 10/1997 |
| EP | 0725665 | 1/1998 |
| EP | 1062988 | 12/2000 |
| EP | 1558333 | 5/2007 |
| EP | 1727591 | 4/2009 |
| EP | 2383014 | 11/2011 |
| EP | 2291115 | 9/2013 |
| EP | 2801389 | 11/2014 |

(56) References Cited

FOREIGN PATENT DOCUMENTS

| | | |
|---|---|---|
| EP | 3020448 | 5/2016 |
| EP | 2029222 | 3/2017 |
| EP | 2780073 | 9/2017 |
| EP | 1951365 | 10/2017 |
| EP | 3154627 | 4/2018 |
| EP | 2827771 | 5/2018 |
| EP | 3184143 | 7/2018 |
| EP | 3075412 | 12/2018 |
| EP | 3349712 | 7/2019 |
| EP | 3503960 | 3/2020 |
| EP | 3650077 | 5/2020 |
| EP | 3352846 | 7/2020 |
| EP | 3493874 | 8/2020 |
| EP | 3409200 | 9/2020 |
| EP | 3427793 | 11/2020 |
| EP | 3758595 | 1/2021 |
| EP | 3641876 | 4/2021 |
| EP | 3679979 | 6/2021 |
| EP | 3841967 | 6/2021 |
| EP | 3402404 | 7/2021 |
| EP | 3562541 | 7/2021 |
| EP | 3675795 | 8/2021 |
| EP | 3100765 | 1/2022 |
| EP | 3487578 | 12/2022 |
| EP | 4108292 | 12/2022 |
| EP | 3784337 | 6/2023 |
| EP | 4233990 | 8/2023 |
| EP | 3541279 | 9/2023 |
| EP | 3463550 | 3/2024 |
| EP | 3565631 | 4/2024 |
| EP | 4356952 | 4/2024 |
| EP | 3842094 | 5/2024 |
| ES | 2222819 | 3/2006 |
| ES | 2272137 | 6/2008 |
| GB | 2496449 | 5/2013 |
| JP | 2010-527256 | 1/1900 |
| JP | 2002-200178 | 7/2002 |
| JP | 2003-501207 | 1/2003 |
| JP | 2003-533299 | 11/2003 |
| JP | 2004-512104 | 4/2004 |
| JP | 2006-503658 | 2/2006 |
| JP | 2008-018235 | 1/2008 |
| JP | 2009-034328 | 2/2009 |
| JP | 2009-512516 | 3/2009 |
| JP | 2009-529352 | 8/2009 |
| JP | 2010-506618 | 3/2010 |
| JP | 2010-512926 | 4/2010 |
| JP | 2010-246745 | 11/2010 |
| JP | 2012-005596 | 1/2012 |
| JP | 2012-055650 | 3/2012 |
| JP | 2012-217565 | 11/2012 |
| JP | 2013-017609 | 1/2013 |
| JP | 2013-094305 | 5/2013 |
| JP | 5439921 | 3/2014 |
| JP | 2015-514460 | 5/2015 |
| JP | 2016-511651 | 4/2016 |
| JP | 2018-038597 | 3/2018 |
| KR | 20130104446 | 9/2013 |
| WO | WO 1987/01024 | 2/1987 |
| WO | WO 1994/000187 | 1/1994 |
| WO | WO 1994/017855 | 8/1994 |
| WO | WO 95/19804 | 7/1995 |
| WO | WO 1996/032909 | 10/1996 |
| WO | WO 98/23326 | 6/1998 |
| WO | WO 98/40121 | 9/1998 |
| WO | WO 1998/043700 | 10/1998 |
| WO | WO 1999/019019 | 4/1999 |
| WO | WO 2000/015293 | 3/2000 |
| WO | WO 2000/076436 | 12/2000 |
| WO | WO 01/03768 | 1/2001 |
| WO | WO 2001/087411 | 11/2001 |
| WO | WO 2002/017987 | 3/2002 |
| WO | WO 2002/034327 | 5/2002 |
| WO | WO 03/015866 | 2/2003 |
| WO | WO 2004/037344 | 5/2004 |
| WO | WO 2004/067087 | 8/2004 |
| WO | WO 2004/108209 | 12/2004 |
| WO | WO 2005/007029 | 5/2005 |
| WO | WO 2005/105201 | 11/2005 |
| WO | WO 2005/122894 | 12/2005 |
| WO | WO 2006/021820 | 3/2006 |
| WO | WO 2006/044793 | 4/2006 |
| WO | WO 2006/092007 | 9/2006 |
| WO | WO 2006/102724 | 10/2006 |
| WO | WO 2007/056493 | 5/2007 |
| WO | WO 2007/092290 | 8/2007 |
| WO | WO 2007/112092 | 10/2007 |
| WO | WO 2008/005478 | 1/2008 |
| WO | WO 2008/045598 | 4/2008 |
| WO | WO 2008/062395 | 5/2008 |
| WO | WO 2008/106174 | 9/2008 |
| WO | WO 2008/150591 | 12/2008 |
| WO | WO 2009/005797 | 1/2009 |
| WO | WO 2009/153730 | 12/2009 |
| WO | WO 2010/014260 | 2/2010 |
| WO | WO 2010/031055 | 3/2010 |
| WO | WO 2010/111321 | 9/2010 |
| WO | WO 2010/141155 | 12/2010 |
| WO | WO 2011/106225 | 9/2011 |
| WO | WO 2011/119224 | 9/2011 |
| WO | WO 2011/144883 | 11/2011 |
| WO | WO 2011/149565 | 12/2011 |
| WO | WO 2011/149656 | 12/2011 |
| WO | WO 2012/040243 | 3/2012 |
| WO | WO 2012/074794 | 6/2012 |
| WO | WO 2013/071307 | 5/2013 |
| WO | WO 2013/074809 | 5/2013 |
| WO | WO 2013/173727 | 11/2013 |
| WO | PCT/US2014/012388 | 1/2014 |
| WO | WO 2014/043757 | 3/2014 |
| WO | WO 2014/053041 | 4/2014 |
| WO | WO 2014/070999 | 5/2014 |
| WO | WO 2014/089549 | 6/2014 |
| WO | WO 2014/093964 | 6/2014 |
| WO | WO 2014/113813 | 7/2014 |
| WO | WO 2014/146082 | 9/2014 |
| WO | WO 2014/151431 | 9/2014 |
| WO | WO 2014/153201 | 9/2014 |
| WO | WO 2014/207512 | 12/2014 |
| WO | WO 2015/033152 | 3/2015 |
| WO | WO 2015/039206 | 3/2015 |
| WO | WO 2015/039244 | 3/2015 |
| WO | WO 2015/042365 | 3/2015 |
| WO | PCT/US2015/033809 | 6/2015 |
| WO | WO 2015/079319 | 6/2015 |
| WO | WO 2015/085880 | 6/2015 |
| WO | WO 2015/095880 | 6/2015 |
| WO | WO 2015/128090 | 9/2015 |
| WO | WO 2015/138981 | 9/2015 |
| WO | WO 2015/164706 | 10/2015 |
| WO | WO 2015/187712 | 12/2015 |
| WO | WO 2016/007093 | 1/2016 |
| WO | WO 2016/019250 | 2/2016 |
| WO | WO 2016/032929 | 3/2016 |
| WO | PCT/US2016/037080 | 6/2016 |
| WO | WO 2016/094728 | 6/2016 |
| WO | WO 2016/102958 | 6/2016 |
| WO | WO 2016/110804 | 7/2016 |
| WO | PCT/US2016/045038 | 8/2016 |
| WO | WO 2016/128985 | 8/2016 |
| WO | PCT/US2016/053513 | 9/2016 |
| WO | WO 2016/149751 | 9/2016 |
| WO | WO 2016/166281 | 10/2016 |
| WO | WO 2016/176668 | 11/2016 |
| WO | WO 2016/179407 | 11/2016 |
| WO | WO 2016/189422 | 12/2016 |
| WO | WO 2016/195587 | 12/2016 |
| WO | WO 2016/201366 | 12/2016 |
| WO | PCT/US2017/014431 | 1/2017 |
| WO | WO 2017/004021 | 1/2017 |
| WO | WO 2017/010930 | 1/2017 |
| WO | WO 2017/023864 | 2/2017 |
| WO | WO 2017/044904 | 3/2017 |
| WO | WO 2017/053847 | 3/2017 |

(56) References Cited

FOREIGN PATENT DOCUMENTS

| | | |
|---|---|---|
| WO | WO 2017/062994 | 4/2017 |
| WO | WO 2017/086798 | 5/2017 |
| WO | WO 2017/088573 | 6/2017 |
| WO | WO 2017/105930 | 6/2017 |
| WO | PCT/US2017/040920 | 7/2017 |
| WO | PCT/US2017/048424 | 8/2017 |
| WO | WO 2017/132067 | 8/2017 |
| WO | WO 2017/199026 | 11/2017 |
| WO | WO 2017/208167 | 12/2017 |
| WO | WO 2017/209673 | 12/2017 |
| WO | WO 2017/210729 | 12/2017 |
| WO | WO 2017/221037 | 12/2017 |
| WO | WO 2018/009680 | 1/2018 |
| WO | WO 2018/028170 | 2/2018 |
| WO | WO 2018/028220 | 2/2018 |
| WO | WO 2018/028221 | 2/2018 |
| WO | WO 2018/039458 | 3/2018 |
| WO | PCT/US2018/025752 | 4/2018 |
| WO | WO 2018/093765 | 5/2018 |
| WO | WO 2018/106839 | 6/2018 |
| WO | WO 2018/112164 | 6/2018 |
| WO | WO 2018119220 | 6/2018 |
| WO | WO 2018/187241 | 10/2018 |
| WO | PCT/US2019/013966 | 1/2019 |
| WO | WO 2019/005774 | 1/2019 |
| WO | WO 2019/014250 | 1/2019 |
| WO | WO 2019/028000 | 2/2019 |
| WO | WO 2019/046180 | 3/2019 |
| WO | PCT/US2019/030458 | 5/2019 |
| WO | PCT/US2019/039193 | 6/2019 |
| WO | WO 2019/082180 | 6/2019 |
| WO | WO 2019/143790 | 7/2019 |
| WO | PCT/US2019/053297 | 9/2019 |
| WO | WO 2019/169240 | 9/2019 |
| WO | PCT/US2019/057674 | 10/2019 |
| WO | WO 2019/202489 | 10/2019 |
| WO | WO 2019/213433 | 11/2019 |
| WO | WO 2020/006048 | 1/2020 |
| WO | PCT/US2020/021503 | 3/2020 |
| WO | WO 2020/068830 | 4/2020 |
| WO | WO 2020/069219 | 4/2020 |
| WO | WO 2020/086726 | 4/2020 |
| WO | WO 2020/131857 | 6/2020 |
| WO | WO 2020/185601 | 9/2020 |
| WO | WO 2020/252406 | 12/2020 |
| WO | WO 2021/005584 | 1/2021 |
| WO | WO 2021/055716 | 3/2021 |
| WO | WO 2021/062345 | 4/2021 |
| WO | PCT/US2021/033231 | 5/2021 |
| WO | WO 2021/092533 | 5/2021 |
| WO | WO 2021/127422 | 6/2021 |
| WO | WO 2021/228128 | 11/2021 |
| WO | WO 2021/236815 | 11/2021 |
| WO | WO 2021/252292 | 12/2021 |
| WO | PCT/US2022/071718 | 4/2022 |
| WO | WO 2022/090834 | 5/2022 |
| WO | PCT/US2022/037600 | 7/2022 |
| WO | PCT/US2022/073451 | 7/2022 |
| WO | PCT/US2022/074376 | 8/2022 |
| WO | PCT/US2022/074377 | 8/2022 |
| WO | WO 2022/187318 | 9/2022 |
| WO | WO 2022/187486 | 9/2022 |
| WO | WO 2022/221858 | 10/2022 |
| WO | WO 2022/235607 | 11/2022 |
| WO | WO 2023/283568 | 1/2023 |
| WO | WO 2023/014499 | 2/2023 |
| WO | WO 2023/015158 | 2/2023 |
| WO | WO 2023/015159 | 3/2023 |
| WO | WO 2023/129722 | 7/2023 |
| WO | WO 2023/156391 | 8/2023 |
| WO | WO 2023/163300 | 8/2023 |
| WO | WO 2023/168016 | 9/2023 |
| WO | WO 2023/191236 | 10/2023 |
| WO | WO 2023/192519 | 10/2023 |
| WO | WO 2023/196578 | 10/2023 |
| WO | WO 2023/215558 | 11/2023 |
| WO | WO 2023/222911 | 11/2023 |
| WO | WO 2024/059136 | 3/2024 |
| WO | WO 2024/059140 | 3/2024 |
| WO | WO 2024/059141 | 3/2024 |
| WO | WO 2024/059643 | 3/2024 |
| WO | WO 2024/059651 | 3/2024 |
| WO | WO 2024/059663 | 3/2024 |
| WO | WO 2024/083685 | 4/2024 |
| WO | WO 2024/086209 | 4/2024 |
| WO | WO 2024/119042 | 6/2024 |
| WO | WO 2024/155527 | 7/2024 |
| WO | WO 2024/182256 | 9/2024 |
| WO | WO 2024/206883 | 10/2024 |
| WO | WO 2024/238988 | 11/2024 |
| WO | WO 2025/038622 | 2/2025 |
| WO | WO 2025/049694 | 3/2025 |
| WO | WO 2025/128510 | 6/2025 |
| WO | WO 2025/128825 | 6/2025 |
| WO | WO 2025/151398 | 7/2025 |
| WO | WO 2025/151439 | 7/2025 |
| WO | WO 2025/155529 | 7/2025 |

OTHER PUBLICATIONS

U.S. Appl. No. 15/354,943, filed Nov. 17, 2016, Wong et al.
U.S. Appl. No. 15/580,631, filed Dec. 7, 2017, Wong et al.
U.S. Appl. No. 15/721,475, filed Sep. 29, 2017, Wong et al.
U.S. Appl. No. 15/721,480, filed Sep. 29, 2017, Wong et al.
U.S. Appl. No. 15/748,616, filed Jan. 29, 2018, Hamner et al.
U.S. Appl. No. 15/762,043, filed Mar. 21, 2018, Hamner et al.
U.S. Appl. No. 16/071,056, filed Jul. 18, 2018, wong et al.
U.S. Appl. No. 16/241,846, filed Jan. 7, 2019, wong et al.
U.S. Appl. No. 16/242,983, filed Jan. 8, 2019, wong et al.
U.S. Appl. No. 16/247,310, filed Feb. 22, 2019, Wong et al.
U.S. Appl. No. 16/327,780, filed Feb. 22, 2019, Hamner et al.
U.S. Appl. No. 16/780,758, filed Feb. 3, 2020, Hamner et al.
U.S. Appl. No. 16/792,100, filed Feb. 14, 2020, Hamner et al.
U.S. Appl. No. 16/833,388, filed Mar. 27, 2020, Hamner et al.
U.S. Appl. No. 16/962,810, filed Jul. 16, 2002, Hamner et al.
U.S. Appl. No. 16/993,085, filed Aug. 13, 2020, Balbaky et al.
U.S. Appl. No. 17/013,396 filed Sep. 4, 1001, Wong et al.
U.S. Appl. No. 17/052,483, filed Nov. 2, 2020, Liberatore et al.
U.S. Appl. No. 17/061,231, filed Oct. 1, 2020, Yu.
U.S. Appl. No. 17/080,544, filed Oct. 26, 2020, Wong et al.
U.S. Appl. No. 17/633,004, filed May 11, 2020, Wong et al.
U.S. Appl. No. 17/633,010, filed May 11, 2022, Wong et al.
Amarenco et al. "Urondynamic Effect of Acute Transducteaneous Posterior Tibial Nerve Stimulation in Overactive Bladder" Journal of Urology vol. 169, 2210-2215 (Jun. 2003).
Apartis; Clinical neurophysiology in movement disorders. Handb Clin Neurol; 111; Pediatric Neurology Pt. 1; pp. 87-92;Apr. 2013.
Barath et al., 2020, Brain metabolic changes with longitudinal transcutaneous afferent patterned stimulation in essential tremor subjects, Tremor and Other Hyperkinetic Movements, 10(1):52, pp. 1-10.
Barbaud et al.; Improvement in essential tremor after pure sensory stroke due to thalamic infarction; European neurology; 46; pp. 57-59; Jul. 2001.
Barrios et al.: BCI algorithms for tremor identification, characterization and tracking; Seventh Framework Programme, EU; Contract No. FP7-ICT-2007-224051 (v3.0); 57 pgs.; Jul. 10, 2011.
Bartley et al.; Neuromodulation for overactive bladder; Nature Reviews Urology; 10; pp. 513-521; Sep. 2013.
Benabid et al.; A putative generalized model of the effects and mechanism of action of high frequency electrical stimulation of the central nervous system; Acta Neural Belg; 105(3); pp. 149-157; Sep. 2005.
Bergquist et al.: Motor unit recruitment when neuromuscular electrical stimulation is applied over a nerve trunk compared with a muscle belly: quadriceps femoris, Journal of Applied Physiology; vol. 113, No. 1, pp. 78-89; Jul. 2012.

(56) References Cited

OTHER PUBLICATIONS

Bergquist et al.; Motor unit recruitment when neuromuscular electrical stimulation is applied over a nerve trunk compared with a muscle belly: triceps surae, Journal of Applied Physiology; vol. 110, No. 3, pp. 627-637; Mar. 2011.
Bijelic et al.: E Actitrode®: The New Selective Stimulation Interface for Functional Movements in Hemiplegic Patients; Serbian Journal of Electrical Engineering; 1(3); pp. 21-28; Nov. 2004.
Birdno et al.; Pulse-to-pulse changes in the frequency of deep brain stimulation affect tremor and modeled neuronal activity.; Journal of Neurophysiology; 98; pp. 1675-1684; Jul. 2007.
Birdno et al.; Response of human thalamic neurons to high-frequency stimulation.; PloS One; 9(5); 10 pgs.; May 2014.
Birgersson et al.; Non-invasive bioimpedance of intact skin: mathematical modeling and experiments; Physiological Measurement; 32(1); pp. 1-18; Jan. 2011.
Bohling et al.; Comparison of the stratum corneum thickness measured in vivo with confocal Raman spectroscopy and confocal reflectance microscopy; Skin research and Technology; 20(1); pp. 50-47; Feb. 2014.
Bonaz, B., V. Sinniger, and S. Pellissier. "Vagus nerve stimulation: a new promising therapeutic tool in inflammatory bowel disease." Journal of internal medicine 282.1 (2017): 46-63.
Bowman et al.; Effects of waveform parameters on comfort during transcutaneous neuromuscular electrical stimulation; Annals of Biomedical Engineering; 13(1); pp. 59-74; Jan. 1985.
Bratton et al.; Neural regulation of inflammation: No. neural connection from the vagus to splenic sympathetic neurons; Exp Physiol 97.11 (2012); pp. 1180-1185.
Brillman et al., 2022, Real-world evidence of transcutaneous afferent patterned stimulation for essential tremor, Tremor and Other Hyperkinetic Movements, 12(1):27, pp. 1-11.
Brittain et al.; Tremor suppression by rhythmic transcranial current stimulation; Current Biology; 23; pp. 436-440; Mar. 2013.
Britton et al.; Modulation of postural tremors at the wrist by supramaximal electrical median nerve shocks in ET, PD, and normal subjects mimicking tremor; J Neurology, Neurosurgery, and Psychiatry; 56(10); pp. 1085-1089; Oct. 1993.
Buschbacher et al.; Manual of nerve conduction series; 2nd edition; Demos Medical Publishing, LLC; 2006.
Buschbacher et al.; Manual of nerve conduction series; 2nd edition; Demos Medical Publishing, LLC; 2006 (part 2, p. #143 to #299).
Cagnan et al.; Phase dependent modulation of tremor amplitude in essential tremor through thalamic stimulation; Brain; 136(10); pp. 3062-3075; Oct. 2013.
Campero et al.; Peripheral projections of sensory fascicles in the human superficial radial nerve; Brain; 128(Pt 4); pp. 892-895; Apr. 2005.
Chen et al.; A web-based system for home monitoring of patients with Parkinson's disease using wearable sensors; IEEE Trans on Bio-Medical Engineering; 58(3); pp. 831-836; Mar. 2011.
Choi, Jong Bo, et al. "Analysis of heart rate variability in female patients with overactive bladder." Urology 65.6 (2005): 1109-1112.
Clair et al.; Postactivation depression and recovery of reflex transmission during repetitive electrical stimulation of the human tibial nerve, Journal of Neurophysiology; vol. 106, No. 1; pp. 184-192; Jul. 2011.
Clar et al.; Skin impedance and moisturization; J. Soc. Cosmet. Chem.; 26; pp. 337-353; 1975;presented at IFSCC Vilith Int'l Congress on Cosmetics Quality and Safety in London on Aug. 26-30, 1974.
Constandinou et al.; A Partial-Current-Steering Biphasic Stimulation Driver for Vestibular Prostheses; IEEE Trans on Biomedical Circuits and Systems; 2(2); pp. 106-113; Jun. 2008.
Daneault et al.; Using a smart phone as a standalone platform for detection and monitoring of pathological tremors; Frontiers in Human Neuroscience; vol. 6, article 357; 12 pgs.; Jan. 2012.
Deuschl et at; Consensus statement of the Movement Disorder Society on Tremor. Ad Hoc Scientific Committee., Movement Disorders, vol. 13 Suppl 3, pp. 2-23; 1998.

Di Giovangiulio et al.; The Neuromodulation of the intestinal immune system and its relevance in inflammatory bowel disease; Frontier's in Immunology; vol. 6; Article 590; Nov. 2015.
Dideriksen et al.; EMG-based characterization of pathological tremor using the iterated Hilbert transform; IEEE transactions on Biomedical Engineering; 58(10); pp. 2911-2921; Oct. 2011.
Dosen et al.: Tremor suppression using electromyography and surface sensory electrical stimulation;Converging Clinical and Engineering Research on Neurorehabilitation; vol. 1 (Biosystems & Biorobotics Series); pp. 539-543; Feb. 2013.
Doucet et al.; Neuromuscular electrical stimulation for skeletal muscle function; The Yale Journal of Biology and Medicine; 85(2); pp. 201-215; Jun. 2012.
Ferreira et al., 2019, MDS evidence-based review of treatments for essential tremor, Movement Disorders, 34(7):950-958.
Fiorentino et al., 2011, Self calibrating wearable active running asymmetry measurement and correction, Journal of Control Engineering and Applied Informatics, 13(2):3-8.
Fred E. Govier, et al., "Percutaneous Afferent Neuromodulation for the Refractory Overactive Bladder: Results of a Multicenter Study," 165 J. Urology 1193-1198 (Apr. 2001).
Fuentes et al.; Restoration of locomotive function in Parkinson's disease by spinal cord stimulation:mechanistic approach, Eur J Neurosci, vol. 32, pp. 1100-1108; Oct. 2010 (author manuscript; 19 pgs.).
Fuentes et al.; Spinal cord stimulation restores locomotion in animal models of Parkinson's disease; Science; 323; pp. 1578-1582; Mar. 2009.
Gallego et al.; A neuroprosthesis for tremor management through the control of muscle co-contraction; Journal of Neuroengineering and Rehabilitation; vol. 10; 36; (13 pgs); Apr. 2013.
Gallego et al.; Real-time estimation of pathological tremor parameters from gyroscope data.; Sensors; 10(3); pp. 2129-2149; Mar. 2010.
Gallego et al; A soft wearable robot for tremor assessment and suppression; 2011 IEEE InternationalConference on Robotics and Automation; Shanghai International Conference Center; pp. 2249-2254; May 9-13, 2011.
Gao; Analysis of amplitude and frequency variations of essential and Parkinsonian tremors; Medical & Biological Engineering & Computing; 42(3); pp. 345-349; May 2004.
Garcia et al.; Modulation of brainstem activity and connectivity by respiratory-gated auricular vagalafferent nerve stimulation in migraine patients; Pain; International Association for the Study of Pain; 2017.
Garcia-Rill, E., et al. "Arousal, motor control, and Parkinson's disease." Translational neuroscience 6.1 pp. 198-207 (2015).
Giuffrida et al.; Clinically deployable Kinesia technology for automated tremor assessment.; Movement Disorders; 24(5); pp. 723-730; Apr. 2009.
Gracanin et al.; Optimal stimulus parameters for minimum pain in the chronic stimulation of innervated muscle; Archives of Physical Medicine and Rehabilitation; 56(6); pp. 243-249; Jun. 1975.
Gupta et al., 2021, Exploring essential tremor: results from a large online survey, Clinical Parkinsonism & Related Disorders, 5:100101, 4 pp.
H.C. Klingler, et al., "Use of Peripheral Neuromodulation of the S3 Region for Treatment of Detrusor Overactivity: A Urodynamicbased Study," Urology 56:766-771, 2000.
Haeri et al.; Modeling the Parkinson's tremor and its treatments; Journal of Theoretical Biology; 236(3); pp. 311-322; Oct. 2005.
Halonen et al.; Contribution of cutaneous and muscle afferent fibres to cortical SEPs followingmedian and radial nerve stimulation in man; Electroenceph. Clin. Neurophysiol.; 71(5); pp. 331-335; Sep.-Oct. 1988.
Hao et al.; Effects of electrical stimulation of cutaneous afferents on corticospinal transmission oftremor signals in patients with Parkinson's disease; 6th International Conference on Neural Engineering; San Diego, CA; pp. 355-358; Nov. 2013.
Haubenberger et al., 2018, Essential Tremor, The New England Journal of Medicine, 378:1802-1810 and Supplementary Appendix.
Hauptmann et al.; External trial deep brain stimulation device for the application of desynchronizing stimulation techniques; Journal of Neural Engineering; 6; 12 pgs.; Oct. 2009.

(56) References Cited

OTHER PUBLICATIONS

Heller et al.; Automated setup of functional electrical stimulation for drop foot using a novel 64 channel prototype stimulator and electrode array: Results from a gait-lab based study; Medical Engineering & Physic; 35(1); pp. 74-81; Jan. 2013.
Hellwig et al., Feb. 17, 2001, Tremor-correlated cortical activity in essential tremor, The Lancet, 357:519-523.
Henry Dreyfuss Associates; The Measure of Man and Woman: Human Factors in Design (Revised Edition); John Wiley & Sons, New York; pp. 10-11 and 22-25; Dec. 2001.
Hernan, Miguel, et al. "Alcohol Consumption and the Incidence of Parkinson's Disease." May 15, 2003. Annals of Neurology. vol. 54. pp. 170-175.
Hernandez-Martin et al., 2021, High-fidelity transmission of high-frequency burst stimuli from peripheral nerve to thalamic nuclei in children with dystonia, Scientific Reports, 11:8498, 9 pp.
Hua et al.; Posture-related oscillations in human cerebellar thalamus in essential tremor are enabled by voluntary motor circuits; J Neurophysiol; 93(1); pp. 117-127; Jan. 2005.
Huang, et al.; Theta burst stimulation report of the human motor cortex; Neuron, vol. 45, 201-206, Jan. 20, 2005.
Hubeaux, Katelyne, et al. "Autonomic nervous system activity during bladder filling assessed by heartrate variability analysis in women with idiopathic overactive bladder syndrome or stress urinary incontinence." The Journal of urology 178.6 (2007): 2483-2487.
Hubeaux, Katelyne, et al. "Evidence for autonomic nervous system dysfunction in females with idiopathic overactive bladder syndrome." Neurology and urodynamics 30.8 (2011): 1467-1472.
Inoue et al. "Stretchable human interface using a conductive silicone elastomer containing silver fillers." Consumer Electronics, 2009. ISCE'09. IEEE 13th International Symposium on. IEEE, 2009.
Isaacson et al., 2020, Prospective home-use study on non-invasive neuromodulation therapy for essential tremor, Tremor and Other Hyperkinetic Movements, 10(1):29, pp. 1-16.
Jacks et al.; Instability in human forearm movements studied with feed-back-controlled electrical stimulation of muscles; Journal of Physiology; 402; pp. 443-461; Aug. 1988.
Jobges et al.; Vibratory proprioceptive stimulation affects Parkinsonian tremor; Parkinsonism & Related Disorders; 8(3); pp. 171-176; Jan. 2002.
Joundi et al.; Rapid tremor frequency assessment with the iPhone accelerometer.; Parkinsonism & Related Disorders; 17(4); pp. 288-290; May 2011.
Kim et al.: Adaptive control of movement for neuromuscular stimulation-assisted therapy in a rodent model; IEEE Trans on Biomedical Engineering,; 56(2); pp. 452-461; Feb. 2009.
Krauss et al.; Chronic spinal cord stimulation in medically intractable orthostatic tremor; J Neurol Neurosurg Psychiatry; 77(9); pp. 1013-1016; Sep. 2006.
Krishnamoorthy et al., 2008, Gait Training After Stroke: A Pilot Study Combining a Gravity-Balanced Orthosis, Functional Electrical Stimulation, and Visual Feedback, Journal of Neurologic Physical Therapy, 32(4):192-202.
Kuhn et al.; Array electrode design for transcutaneous electrical stimulation a simulation study; Medical Engineering & Physics; 31 (8); pp. 945-951; Oct. 2009.
Kuhn et al.; The Influence of Electrode Size on Selectivity and Comfort in Transcutaneous Electrical Stimulation of the Forearm; Neural Systems and Rehabilitation Engineering, IEEE Transactions on; 18(3); pp. 255-262; Jun. 2010.
Kunz, Patrik, et al. "5 kHz transcranial alternating current stimulation: lack of cortical excitability changes when grouped in a theta burst pattern." Frontiers in Human Neuroscience 10 (2016): 683.
Lagerquist et al.: Influence of stimulus pulse width on M-waves, H-reflexes, and torque during tetanic low-intensity neuromuscular stimulation, Muscle & Nerve, 42(6), pp. 886-893; Dec. 2010.
Laroy et al.; The sensory innervation pattern of the fingers; J. Neurol.; 245 (5); pp. 294-298; May 1998.

Lee et al.; Resetting of tremor by mechanical perturbations: A comparison of essential tremor and parkinsonian tremor; Annals of Neurology; 10(6); pp. 523-531; Dec. 1981.
Legon et al.; Pulsed ultrasound differentially stimulates somatosensory circuits in humans as indicated by EEG and fMRI; PLoS ONE; 7(12); e51177; 14 pgs.; Dec. 2012.
Liao, Wen-Chien, et al. "A noninvasive evaluation of autonomic nervous system dysfunction in women with an overactive bladder." International Journal of Gynecology & Obstetrics 110.1 (2010): 12-17.
Lin et al., 2018, Noninvasive neuromodulation inessential tremor demonstrates relief in a sham-controlled pilot trial, Movement Disorders, 33(7):1182-1183.
Llinas et al., Dec. 21, 1999, Thalamocortical dysrhythmia: a neurological and neuropsychiatric syndrome characterized by magnetoencephalography, PNAS, 96(26):15222-15227.
Lourenco et al.; Effects produced in human arm and forearm motoneurons after electrical stimulation of ulnar and median nerves at wrist level; Experimental Brain Research; 178(2); pp. 267-284; Apr. 2007.
Lyons et al., 2021, Essential tremor in adult patients, International Essential Tremor Foundation, 16 pp.
Malek et al.; The utility of electromyography and mechanomyography for assessing neuromuscular function: a noninvasive approach; Phys Med Rehabil in N Am; 23(1); pp. 23-32; Feb. 2012.
Mamorita et al.; Development of a system for measurement and analysis of tremor using a three-axis accelerometer; Methods Inf Med; 48(6); pp. 589-594; epub Nov. 2009.
Maneski et al.; Electrical Stimulation for suppression of pathological tremor; Med Biol Eng Comput; 49(10); pp. 1187-1193; Oct. 2011.
Marsden et al.; Coherence between cerebellar thalamus, cortex and muscle in man; Brain; 123; pp. 1459-1470; Jul. 2000.
Marshall, Ryan, et al. "Bioelectrical stimulation for the reduction of inflammation in inflammatory bowel disease." Clinical Medicine Insights: Gastroenterology 8 (2015): CGast-S31779.
McAuley et al.; Physiological and pathological tremors and rhythmic central motor control; Brain; 123(Pt 8); pp. 1545-1567; Aug. 2000.
McIntyre et al.; Finite element analysis of current-density and electric field generated by metal microelectrodes; Annals of Biomedical Engineering; 29(3); pp. 227-235; Mar. 2001.
Meekins et al.; American Association of Neuromuscular & Electrodiagnostic Medicine evidenced-based review: use of surface electromyography in the diagnosis and study of neuromuscular disorders; Muscle Nerve 38(4); pp. 1219-1224; Oct. 2008.
Mehnert, Ulrich, et al. "Heart rate variability: an objective measure of autonomic activity and bladder sensations during urodynamics." Neurology and urodynamics 28.4 (2009): 313-319.
Michael R. Van Balken, et al., "Posterior Tibial Nerve Stimulation as Neuromodulative Treatment of Lower Urinary Track Dysfunction," 166 J. Urology 914-918 (Sep. 2001).
Miguel et al.; Alcohol consumption and the incidence of Parkinson's disease; Ann. Neurol.; 54(2); pp. 170-175; May 15, 2003.
Miller et al.; Multiplexed microneedle-based biosensor array for characterization of metabolic acidosis; Talanta; 88; pp. 739-742; Jan. 2012 (author manuscript; 13 pgs.).
Miller et al.; Neurostimulation in the treatment of primary headaches; Pract Neurol; Apr. 11, 2016;16:pp. 362-375.
Milne et al.; Habituation to repeated in painful and non-painful cutaneous stimuli: A quantitative psychophysical study; Experimental Brain Research; 87(2); pp. 438-444; Nov. 1991.
Mommaerts et al.; Excitation and nerve conduction; in Comprehensive Human Physiology; Springer Berlin Heidelberg; Chap. 13; pp. 283-294; Mar. 1996.
Mones et al.; The response of the tremor of patients with Parkinsonism to peripheral nerve stimulation; J Neurology, Neurosurgery, and Psychiatry; 32(6); pp. 512-518; Dec. 1969.
Morgante et al.: How many parkinsonian patients are suitable candidates for deep brain stimulationof subthalamic nucleus?; Results of a Questionnaire, Parkinsonism Relat Disord; 13; pp. 528-531; Dec. 2007.

(56)　　　　　References Cited

OTHER PUBLICATIONS

Munhoz et al; Acute effect of transcutaneous electrical nerve stimulation on tremor; Movement Disorders; 18(2); pp. 191-194; Feb. 2003.

Nardone et al.; Influences of transcutaneous electrical stimulation of cutaneous and mixed nerves onsubcortical somatosensory evoked potentials; Electroenceph. Clin. Neurophysiol.; 74(1); pp. 24-35; Jan.-Feb. 1989.

Nonis et al.; Evidence of activation of vagal afferents by non-invasive vagus nerve stimulation: Anelectrophysiological study in healthy volunteers; Cephalalgia; pp. 1285-1293; vol. 37(13); Mar. 28, 2017.

Pahwa et al., 2018, An acute randomized controlled trial of noninvasive peripheral nerve stimulation in essential tremor, Neuromodulation, 22:537-545.

Peng et al., 2015, Flexible dry electrode based on carbon nanotube/polymer hybrid micropillars for biopotential recording, Sensor and Actuatora A: Physical, 235:48-65.

Perez et al.; Patterned Sensory Stimulation Induces Plasticity in Reciprocal la Inhibition in Humans; The Journal of Neuroscience; 23(6); pp. 2014-2018; Mar. 2003.

Perez-Reyes, Jan. 2003, Molecular physiology of low-voltage-activated T-type calcium channels, Physiol. Rev. 83:117-161.

Perlmutter et al.; Deep brain stimulation; Ann Rev Neurosci; 29; pp. 229-257; Jul. 2006.

Popovi Maneski et al.; Electrical stimulation for the suppression of pathological tremor; Medical & Biological Engineering & Computing; 49(10); pp. 1187-1193; Oct. 2011.

Popovic-Bijelic et al. "Multi-field surface electrode for selective electrical stimulation." Artificial organs 29.6 (2005): 448-452.

Prochazka et al.; Attenuation of pathological tremors by functional electrical stimulation I: Method; Annals of Biomedical Engineering; 20(2); pp. 205-224; Mar. 1992.

Pulliam et al.; Continuous in-home monitoring of essential tremor; Parkinsonism Relat Disord; 20(1); pp. 37-40; Jan. 2014.

Quattrini et al.; Understanding the impact of painful diabetic neuropathy; Diabetes/Metabolism Research and Reviews; 19, Suppl. 1; pp. S2-8; Jan.-Feb. 2003.

Rocon et al.; Design and validation of a rehabilitation robotic exoskeleton for tremor assessment and suppression; IEEE Trans Neural Sys and Rehab Eng.; 15(3); pp. 367-378; Sep. 2007.

Sigrist et al., 2012. Augmented visual, auditory, haptic, and multimodal feedback in motor learning: A review. Psychonomic Bulletin & Review, 20(1):21-53.

Silverstone et al.; Non-Invasive Neurostimulation In The Control of Familial Essential Tremor Using The Synaptic Neuromodulator; Conference Proceedings, International Functional Electrical Stimulation Society (IFES); Ed. Paul Meadows; 3 pgs.; May 1999.

Singer et al.; The effect of EMG triggered electrical stimulation plus task practice on arm function inchronic stroke patients with moderate-severe arm deficits; Restor Neurol Neurosci; 31(6); pp. 681-691; Oct. 2013.

Solomonow et al., 1998, Studies toward spasticity suppression with high frequency electrical stimulation, Orthopedics, 7(8):1284-1288.

Straube et al.; Treatment of chronic migraine with transcutaneous stimulation of the auricular branchof the vagal nerve (auricular t-VNS): a randomized, monocentric clinical trial; The Journal of Headache and Pain (2015) 16:63.

Takanashi et al.; A functional MRI study of somatotopic representation of somatosensory stimulation in the cerebellum; Neuroradiology; 45(3); pp. 149-152; Mar. 2003.

Tass et al.; Coordinated reset has sustained aftereffects in Parkinsonian monkeys; Ann Neurol; 72(5); pp. 816-820; Nov. 2012.

Tass et al.; Counteracting tinnitus by acoustic coordinated reset neuromodulation; Restorative neurology and Neuroscience; 30(2); pp. 137-159; Apr. 2012.

Tass; A Model of desynchronizing deep brain stimulation with a demand-controlled coordinated reset of neural subpopulations; Biol Cybern; 89(2); pp. 81-88; Aug. 2003.

Thomas et al.; A review of posterior tibial nerve stimulation for faecal incontinence; ColorectalDisease; 2012 The Association of Coloproctology of Great Britain and Ireland. 15, pp. 519-526; Jun. 25, 2012.

Tolosa et al.; Essential tremor: treatment with propranolol; Neurology; 25(11); pp. 1041; Nov. 1975.

Tracey; The inflammatory reflex; Nature; vol. 420; pp. 853-859; Dec. 19-26, 2002.

Treager; Interpretation of skin impedance measurements; Nature; 205; pp. 600-601; Feb. 1965.

Valente; Novel methods and circuits for field shaping in deep brain stimulation; Doctoral thesis, UCL (University College London); 222 pgs.; 2011.

Vitton et al.; Transcutaneous posterior tibial nerve stimulation for fecal Incontinence in inflammatorybowel disease patients: a therapeutic option?; Inflamm Bowel Dis; vol. 15, No. 3, Mar. 2009; pp. 402-405.

Von Lewinski et al.; Efficacy of EMG-triggered electrical arm stimulation in chronic hemiparetic stroke patients; Restor Neurol Neurosci; 27(3); pp. 189-197; Jun. 2009.

Wardman et al.; Subcortical, and cerebellar activation evoked by selective stimulation of muscle and cutaneous afferents: an fMRI study; Physiol. Rep.; 2(4); pp. 1-16; Apr. 2014.

Wiestler et al.; Integration of sensory and motor representations of single fingers in the human; J. Neurophysiol.; 105(6); pp. 3042-3053; Jun. 2011.

Woldag et al.; Evidence-based physiotherapeutic concepts for improving arm and hand function in stroke patients R A review; J Neurol; 249(5); pp. 518-528; May 2002.

Woolf et al.; Peripheral nerve injury triggers central sprouting of myelinated afferents; Nature; 355(6355); pp. 75-78; Jan. 1992.

Yarnitsky et al.; Nonpainful remote electrical stimulation alleviates episodic migraine pain; Neurology 88; pp. 1250-1255; Mar. 28, 2017.

Yeh et al., "Intensity sensitive modulation effect of theta burst form of median nerve stimulation on the monosynaptic spinal reflex." Neural plasticity 2015 (2015) in 8 pages.

Yilmaz, Ozlem O., et al. "Efficacy of EMG-biofeedback in knee osteoarthritis." Rheumatology international 30.7 (2010): 887-892.

Zhang et al.; Neural oscillator based control for pathological tremor suppression via functional electrical stimulation; Control Engineering Practice; 19(1); pp. 74-88; Jan. 2011.

Zorba et al.; Overactive bladder and the pons; Rize University, Medical Faculty, Department of Urology; 123-124; Undated.

Zwarts et al.; Multichannel surface EMG: basic aspects and clinical utility; Muscle Nerve; 28(1); pp. 1-17; Jul. 2003.

Wallerberger, Markus. "Efficient Estimation of Autocorrelation Spectra." ArXiv.org, Apr. 4, 2019, https://arxiv.org/abs/1810.05079. (Year: 2019).

U.S. Appl. No. 14/805,385 (now U.S. Pat. No. 9,452,287), filed Jul. 21, 2015.

U.S. Appl. No. 15/277,946 (now U.S. Pat. No. 10,850,090), filed Sep. 27, 2016.

U.S. Appl. No. 15/983,024 (now U.S. Pat. No. 10,625,074), filed May 17, 2018.

U.S. Appl. No. 17/107,435, filed Nov. 30, 2020.

U.S. Appl. No. 16/020,876 (published as U.S. Pub. No. 2019/0001129), filed Jun. 27, 2018.

U.S. Appl. No. 14/271,669 (published as U.S. Pub. No. 2014/0336722), filed Nov. 13, 2014.

U.S. Appl. No. 15/354,943 (now U.S. Pat. No. 9,802,041), filed Nov. 17, 2016.

U.S. Appl. No. 15/721,475 (now U.S. Pat. No. 10,179,238), filed Sep. 29, 2017.

U.S. Appl. No. 15/721,480 (now U.S. Pat. No. 10,173,060), filed Sep. 29, 2017.

U.S. Appl. No. 16/242,983 (now U.S. Pat. No. 10,549,093), filed Jan. 8, 2019.

U.S. Appl. No. 16/247,310 (now U.S. Pat. No. 10,561,839), filed Jan. 14, 2019.

U.S. Appl. No. 16/780,758 (now U.S. Pat. No. 10,905,879), filed Feb. 3, 2020.

(56) References Cited

OTHER PUBLICATIONS

U.S. Appl. No. 16/792,100 (now U.S. Pat. No. 10,960,207), filed Feb. 14, 2020.
U.S. Appl. No. 17/164,576, filed Feb. 1, 2021.
U.S. Appl. No. 17/216,372, filed Mar. 29, 2021.
U.S. Appl. No. 15/580,631 (now U.S. Pat. No. 10,765,856), filed Dec. 7, 2017.
U.S. Appl. No. 17/013,396 (published as U.S. Pub. No. 2021/0052883), filed Sep. 4, 2020.
U.S. Appl. No. 16/071,056 (published as U.S. Pub. No. 2021/00205619), filed Jul. 18, 2018.
U.S. Appl. No. 16/500,377 (published as U.S. Pub. No. 2021/0101007), filed Apr. 2, 2018.
U.S. Appl. No. 15/748,616 (published as U.S. Pub. No. 2020/0093400), filed Aug. 1, 2016.
U.S. Appl. No. 15/762,043 (now U.S. Pat. No. 10,603,482), filed Mar. 21, 2018.
U.S. Appl. No. 16/833,388 (published as U.S. Pub. No. 2020/0289814), filed Mar. 27, 2020.
U.S. Appl. No. 16/241,846 (now U.S. Pat. No. 10,814,130), filed Jan. 7, 2019.
U.S. Appl. No. 17/080,544 (published as U.S. Pub. No. 2021/0113834), filed Oct. 26, 2020.
U.S. Appl. No. 16/327,780, filed Feb. 22, 2019.
U.S. Appl. No. 16/962,810 (published as U.S. Pub. No. 2021/0252278), filed Jan. 17, 2019.
U.S. Appl. No. 17/052,483 (published as U.S. Pub. No. 2021/0244940), filed Jan. 17, 2019.
U.S. Appl. No. 17/279,048, filed Mar. 23, 2021.
U.S. Appl. No. 17/287,471 (published as U.S. Pub. No. 2021/0379374), filed Apr. 21, 2021.
U.S. Appl. No. 17/433,451, filed Aug. 24, 2021.
U.S. Appl. No. 16/993,085, filed Aug. 13, 2020.
U.S. Appl. No. 17/061,231, filed Oct. 1, 2020.
U.S. Appl. No. 17/808,850, filed Jun. 24, 2022.
Antal et al., Anodal Transcranial Direct Current Stimulation of the Motor Cortex Ameliorates Chronic Pain and Reduces Short Intracortical Inhibition, Journal of Pain and Symptom Management, vol. 39, No. 5, pp. 890-903, May 2010.
Cala kIQ, calahealth.com, [online], [site visited Mar. 7, 2025], Available from internet URL: https://calahealth.com/ (Year: 2025).
Dewey, et al., A Pilot Study of Ai-Controled Transcutaneous Peripheral Nerve Stimulation for Essential Tremor, Tremor and Other Hyperkinetic Movements, 2025; 15(1):10, pp. 1-9.
Falco et al., Cross Talk: A New Method for Peripheral Nerve Stimulation. An Observational Report with Cadaveric Verification, Pain Physician, 12:965-983, 2009.
Lowry et al., Spinal Cord Stimulation for the Treatment of Chronic Knee Pain Following Total Knee Replacement, Pain Physician, 13:251-256, 2010.
Trends in the Health Wearable Technology, first available Oct. 26, 2021, mokosmart.com, [online], [site visited Mar. 7, 2025], Available from internet URL: https://www.mokosmart.com/health-wearable-technology-trends/ (Year: 2021).
Aemed, Inc., 510(k) Summary, StimPad™ TENS System, Dec. 6, 2007.

Cala Trio Health Care Professional Guide (Jul. 2020).
Cala Trio Health Care Professional Guide (Nov. 2019).
Chang, M.D., Qwang-Yuen et al., Effect of Electroacupuncture and Transcutaneous Electrical Nerve Stimulation at Hegu (LI.4) Acupuncture Point on the Cutaneous Reflect, 27 Acupuncture & Electro-Therapeutics Res., Int. J. 191-202 (2002).
Encore Medical, L.P., Intelect Transport 2 Channel Electrotherapy User Manual, 2005.
Fowler et al., The conduction velocities of peripheral nerve fibres conveying sensations of warming and cooling, Journal of Neurology, Neurosurgery and Psychiatry Sep. 1988;51(9):1164-70.
Griffin et al., Efficacy of High Voltage Pulsed Current for Healing of Pressure Ulcers in Patents with Spinal Cord Injury, Physical Therapy, vol. 71, No. 6, Jun. 1991, pp. 433-442.
Javidan, et al, Attenuation of Pathological Tremors by Functional Electrical Stimulation II: Clinical Evaluation, 20 Annals of Biomedical Engineering 225 (1992).
Johnson, Factors Influencing The Analgesic Effects and Clinical Efficacy of Transcutaneous Electrical Nerve Stimulation (TENS), Newcastle University, Jul. 1991.
Jones et al., Trancutaneous electronical nerve stimulation, Continuing Education in Anaethesia, Critical Care & Pain, vol. 9, No. 4, pp. 130-135, 2009.
Knutson et al., Neuromuscular Electrical Stimulation for Motor Restoration in Hemiplegia. Phys Med Rehabil Clin N A,. Nov. 2015; 26(4): 729-745. Published online Aug. 14, 2015. Doi: 10.1016/j.pmr.2015.06.002.
Korkmaz et al., Pulsed radiofrequency versus conventional transcutaneous electrical nerve stimulation in painful shoulder: a prospective, randomized study, Clin Rehabil. Nov. 2010;24(11):1000-8, Aug. 4, 2010.
Miller et al., Superimposed single impulse and pulse train electrical stimulation: A quantitative assessment during submaximal isometric knee extension in young, healthy men, Superimposed Electrical Stimulation Techniques, Muscle & Nerve, Aug. 1999, pp. 1038-1046.
Wallerberger, Apr. 4, 2019, Efficient Estimation of Autocorrelation Spectra, ArXiv.org, https://arxiv.org/abs/1810.05079.
De Santana, et al., Effectiveness of Transcutaneous Electrical Nerve Stimulation for Treatment of Hyperalgesia and Pain, Curr Rheumatol Rep.; 10(6): 492-499, Dec. 2008.
PTAB-IPR2024-00732—Exhibit 1002—Declaration of John Laughlin, M. Eng., P.E., in 109 pages.
PTAB-IPR2024-00732—Petition for Inter Partes Review of U.S. Pat. No. 10,786,669, filed Mar. 29, 2024, in 101 pages.
PTAB-IPR2024-00743—Exhibit 1002—Declaration of John Laughlin, M. Eng., P.E., in 102 pages.
PTAB-IPR2024-00743—Petition for Inter Partes Review of U.S. Pat. No. 11,628,300, filed Mar. 29, 2024, in 113 pages.
Feinstein Institutes for Medical Research, Northwell Health; High-frequency electrical stimulation helps reduce inflammation pain in new Feinstein Institute study; Press Release Oct. 5, 2022.
Yang et al.; High-frequency electrical stimulation attenuates neuronal release of inflammatory mediators and ameliorates neuropathic pain, Bioelectronic Medicine, 8(1); pp. 1-13; Oct. 5, 2022.

* cited by examiner

Device log analysis algorithms
- detect and classify anomalous events

Anomalous Sequence
Detection Algorithm (ASDA)
- *Markov Chains*

Event Sequence
Classification Algorithm
(ESCA)
- *Artificial Neural Nets*

| Time | Device log event |
|------|------------------|
| 2019-01-16 14:21:12 | s |
| 2019-01-16 15:01:12 | e |
| 2019-01-16 15:01:12 | i |
| 2019-01-16 15:01:35 | m |
| 2019-01-16 15:01:50 | t |

Figure 8C

Continuous time Markov model of device interaction

Predict likelihood of an event sequence $$\text{Likelihood} = \prod_{\text{1st event}}^{\text{Last event}} \text{Pr(Next event after n seconds | current event)}$$

$$\text{Likelihood}_{\text{expected}} = \prod_{\text{1st event}}^{\text{Last event}} \text{Pr(current event)}$$

$$\text{Anomaly score} = \log(\text{Likelihood} / \text{Likelihood}_{\text{expected}})$$

Unsupervised clustering with Self Organizing Maps

• Unsupervised grouping of multi-dimensional data

• Maps input data onto a topographic map of neurons

Feature encoding of event sequence

- Event identity
  - 7 events in sequence
  - One Hot encoding of 11 event types

- Time interval
  - 6 intervals
  - Log normalized time
  - Scaled from 0 - 1

Neuron 12-10

```
r 1024 i 0 e 8 m 1 m 4 t 16384 m
r 1024 i 0 e 8 m 1 m 4 t 32768 m
r 1024 i 0 e 8 m 0 m 4 t 16384 m
r 1024 i 0 e 4 m 1 m 8 t 16384 m
r 1024 i 0 e 8 m 1 m 4 t 16384 m
r 1024 i 0 e 16 m 1 m 2 t 32768 m
r 1024 i 0 e 8 m 0 m 4 t 16384 m
r 1024 i 0 e 8 m 0 m 2 t 16384 m
r 1024 i 0 e 8 m 0 m 4 t 32768 m
r 1024 i 0 e 16 m 0 m 2 t 32768 m
```

NEUROSTIMULATION SYSTEMS WITH EVENT PATTERN DETECTION AND CLASSIFICATION

REFERENCE TO RELATED APPLICATIONS

This application is a continuation of U.S. patent application Ser. No. 17/061,231 filed Oct. 1, 2020, now U.S. Pat. No. 11,189,468, which claims the benefit under 35 U.S.C. § 119(e) as a nonprovisional application of U.S. Provisional App. Nos. 62/910,260 filed on Oct. 3, 2019, and 62/933,816 filed on Nov. 11, 2019, each of the foregoing of which are incorporated by reference in their entireties.

BACKGROUND

Field

Embodiments of the invention relate generally to systems, devices, and methods for stimulating nerves, and more specifically relate to system, devices, and methods for electrically stimulating peripheral nerve(s) to treat various disorders, as well as signal processing systems and methods for enhancing device monitoring protocols and detecting abnormal patient usage of the device.

Description of the Related Art

A wide variety of modalities can be utilized to neuro-modulate peripheral nerves. For example, electrical energy can be delivered transcutaneously via electrodes on the skin surface with neurostimulation systems to stimulate peripheral nerves, such as the median, radial, and/or ulnar nerves in the upper extremities; the tibial, saphenous, and/or peroneal nerve in the lower extremities; or the auricular vagus, tragus, trigeminal or cranial nerves on the head or ear, as non-limiting examples. Stimulation of these nerves has been shown to provide therapeutic benefit across a variety of diseases, including but not limited to movement disorders (including but not limited to essential tremor, Parkinson's tremor, orthostatic tremor, and multiple sclerosis), urological disorders, gastrointestinal disorders, cardiac diseases, and inflammatory diseases, mood disorders (including but not limited to depression, bipolar disorder, dysthymia, and anxiety disorder), pain syndromes (including but not limited to migraines and other headaches, trigeminal neuralgia, fibromyalgia, complex regional pain syndrome), among others. A number of conditions, such as tremors, can be treated through some form of transcutaneous, percutaneous, or other implanted forms of peripheral nerve stimulation. Wearable systems with compact, ergonomic form factors are needed to enhance efficacy, compliance, and comfort with using the devices.

SUMMARY

In some embodiments, disclosed herein is a neuromodulation device according to any one or more of the embodiments described in the disclosure.

Also disclosed herein are systems and/or methods for determining or predicting device malfunction and/or abnormal patient usage according to any one or more of the embodiments described in the disclosure.

In some embodiments, patient-device interaction and/or device function can be monitored in real-time or near real-time.

In some embodiments, patient usage patterns can be automatically detected to inform patient-oriented assistance or device diagnostics.

Further disclosed herein are systems and/or methods for predicting a response to therapy or lack thereof, according to any one or more of the embodiments described in the disclosure.

In some embodiments, disclosed herein is a wearable neurostimulation device for transcutaneously stimulating one or more peripheral nerves of a user. The device can include one or more electrodes configured to generate electric stimulation signals; one or more sensors configured to detect motion signals, wherein the one or more sensors are operably connected to the wearable neurostimulation device; and/or one or more hardware processors configured to receive raw signals relating to device interaction events; store the device interaction events into a data log; perform an anomalous sequence detection analysis on entries of the data log; perform an event sequence classification on entries of the data log; determine at least one of an anomaly type and/or an anomaly score; and/or determine anomalous device function patterns or device usage patterns.

In some embodiments, the sensors are operably attached to the wearable neurostimulation device.

In some embodiments, the anomalous sequence detection analysis comprises utilizing Markov chains.

In some embodiments, the Markov chains comprise modified continuous time Markov chains.

In some embodiments, the anomalous sequence detection analysis comprises converting a time interval into a time bin on a logarithmic scale.

In some embodiments, the anomalous sequence detection analysis comprises estimating the influence of null count events on probability calculations.

In some embodiments, the device further comprises one or more end effectors configured to generate stimulation signals other than electric stimulation signals.

In some embodiments, the stimulation signals other than electric stimulation signals are vibrational stimulation signals.

In some embodiments, the sensors comprise one or more of a gyroscope, accelerometer, and magnetometer.

In some embodiments, the anomalous sequence detection analysis comprises identifying a sequence of button presses.

In some embodiments, the anomalous sequence detection analysis comprises identifying patient early termination of therapy.

In some embodiments, disclosed herein is a neuromodulation device for modulating one or more nerves of a user, the device comprising one or more electrodes configured to generate electric signals; one or more sensors configured to detect motion signals, wherein the one or more sensors are operably connected to the device; and one or more hardware processors configured to: receive raw signals relating to device interaction events; store the device interaction events into a data log; perform an anomalous sequence detection analysis on entries of the data log; perform an event sequence classification on entries of the data log; determine at least one of an anomaly type and/or an anomaly score; and determine anomalous device function patterns or device usage patterns.

In some embodiments, the neuromodulation is stimulatory.

In some embodiments, the neuromodulation is inhibitory.

In some embodiments, the neuromodulation is partially stimulatory and partially inhibitory.

In some embodiments, the device is wearable.

In some embodiments, the device is a non-wearable.

In some embodiments, the device is a band for the wrist.

In some embodiments, the device is a band for a limb.

In some embodiments, the device is a patch.

In some embodiments, the device is partially or completely transcutaneous.

In some embodiments, the nerves are one or more peripheral nerves.

In some embodiments, the nerves are located on or near a wrist, an arm, an ankle, a leg, or an ear.

In some embodiments, the sensors are operably attached to the device.

In some embodiments, the anomalous sequence detection analysis comprises utilizing Markov chains.

In some embodiments, the Markov chains comprise modified continuous time Markov chains.

In some embodiments, the anomalous sequence detection analysis comprises converting a time interval into a time bin on a logarithmic scale.

In some embodiments, the anomalous sequence detection analysis comprises estimating the influence of null count events on probability calculations.

In some embodiments, a device further comprises one or more end effectors configured to generate signals other than electric signals.

In some embodiments, a device further comprises one or more end effectors configured to generate signals other than electric signals, wherein said other signals include vibration.

In some embodiments, the sensors comprise one or more of a gyroscope, accelerometer, and magnetometer.

In some embodiments, the anomalous sequence detection analysis comprises identifying a sequence of button presses.

In some embodiments, the anomalous sequence detection analysis comprises identifying patient early termination of therapy.

In some embodiments, disclosed herein is a neuromodulation device, comprising any one or more of the embodiments described in the disclosure.

In some embodiments, a system for determining or predicting device malfunction and/or abnormal patient usage can comprise, consist essentially of, consist of, or not comprise any one or more of the embodiments described in the disclosure.

In some embodiments, a method for determining or predicting device malfunction and/or abnormal patient usage, can comprise, consist essentially of, consist of, or not comprise any one or more of the embodiments described in the disclosure.

The embodiments described herein that, for example, determine or predict device malfunction and/or abnormal patient usage of a neuromodulation system can have one or more of the following advantages: (i) greater therapeutic benefit with improved reliability and patient satisfaction (e.g., from detecting events in advance of actual device malfunction, and contacting the patient in advance for replacement, repair, and/or patient education); (ii) decreased device error alerts and interruptions in therapy (and thus delays in completing a therapy session); (iii) increased likelihood of patient compliance due to the foregoing; (iv) determining whether patient compliance with therapy or device anomalies need to be addressed if efficacy of treatment is not as expected; (v) correlate clinical ratings of medical conditions, e.g., tremor severity can correlate with simultaneous measurements of wrist motion using inertial measurement units (IMUs); and/or (vi) correlate symptoms or other features extracted from sensors to provide characteristic information about disease phenotypes that may be leveraged to improve diagnosis, prognosis, and/or therapeutic outcomes.

In some of the embodiments described herein, one, several or all of the following features are not included: (i) sensors configured to assess patient motion and/or collect motion data, (ii) accelerometers, gyroscopes, magnetometers, inertial measurement units. and (iii) EMG or other muscle sensors. In some embodiments, systems and methods are not configured for, or are not placed on the upper arm and/or are not configured for neuromodulation on the skin surface of the forehead. In some embodiments, systems and methods are not configured to, or do not modulate descending (e.g., efferent) nerve pathways, and only modulate ascending (e.g., afferent) nerve pathways. In some embodiments, systems and methods are not configured to, or do not modulate nerves only on the ventral side of the wrist. In some embodiments, systems and methods do not include any implantable components. In some embodiments, systems and methods are not configured for percutaneous or subcutaneous stimulation, and are only configured for transcutaneous neuromodulation. In some embodiments, systems and methods are not configured for only neuromodulating, e.g., stimulating the ventral side of the wrist, rather some configurations may neuromodulate, e.g., deliver stimulation between two or more of the ventral, dorsal, and/or lateral sides of the wrist to target the medial nerve.

BRIEF DESCRIPTION OF THE DRAWINGS

Figure 3:
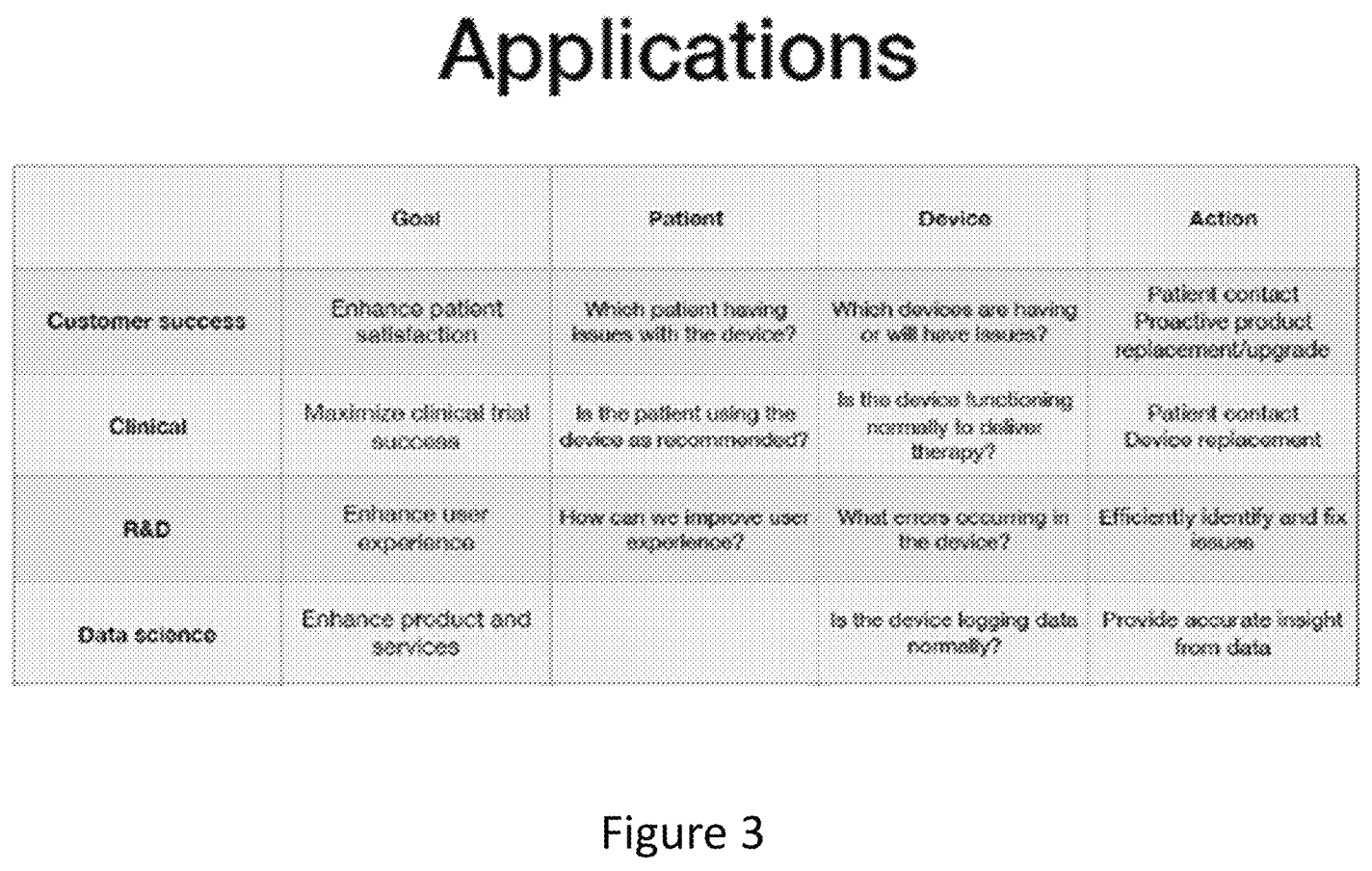

FIG. 3 is a table matrix indicating various non-limiting advantages of systems and methods as disclosed herein according to some embodiments, including in the customer success, clinical, R&D, and data science areas.

FIG. 4 illustrates a schematic illustrating examples of system and method functionality of some embodiments.

FIG. 8C illustrates example data collections sequence with event markers and corresponding time stamps.

DETAILED DESCRIPTION

Figure 1A:
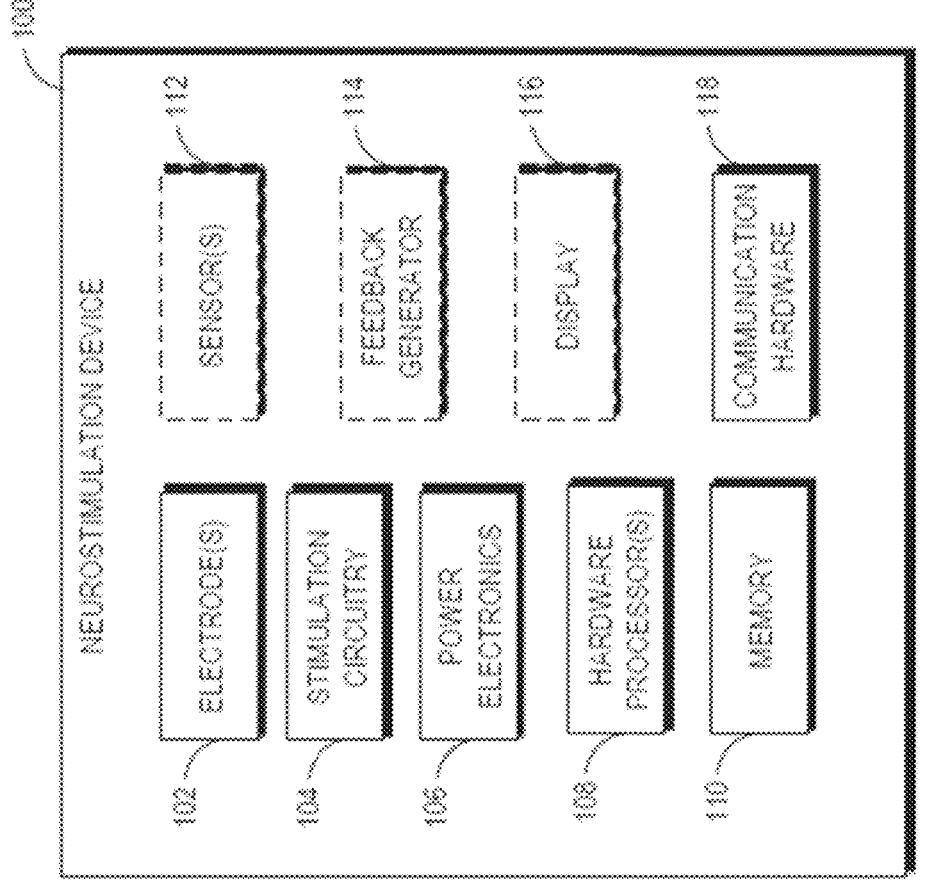
FIG. 1A illustrates a block diagram of an example neuromodulation (e.g., neurostimulation) device.

Disclosed herein are devices configured for providing neuromodulation (e.g., neurostimulation). The neuromodulation (e.g., neurostimulation) devices provided herein may be configured to stimulate peripheral nerves of a user. The neuromodulation (e.g., neurostimulation) devices may be configured to transcutaneously transmit one or more neuromodulation (e.g., neurostimulation) signals across the skin of the user. In many embodiments, the neuromodulation (e.g., neurostimulation) devices are wearable devices configured to be worn by a user. The user may be a human, another mammal, or other animal user. The neuromodulation (e.g., neurostimulation) system could also include signal processing systems and methods for enhancing diagnostic and therapeutic protocols relating to the same. In some embodiments, the neuromodulation (e.g., neurostimulation) device is configured to be wearable on an upper extremity of a user (e.g., a wrist, forearm, arm, and/or finger(s) of a user). In some embodiments, the device is configured to be wearable on a lower extremity (e.g., ankle, calf, knee, thigh, foot, and/or toes) of a user. In some embodiments, the device is configured to be wearable on the head or neck (e.g., forehead, ear, neck, nose, and/or tongue). In several embodiments, dampening or blocking of nerve impulses and/or neurotransmitters are provided. In some embodiments, nerve impulses and/or neurotransmitters are enhanced. In some embodiments, the device is configured to be wearable on or proximate an ear of a user, including but not limited to auricular neuromodulation (e.g., neurostimulation) of the auricular branch of the vagus nerve, for example. The device could be unilateral or bilateral, including a single device or multiple devices connected with wires or wirelessly.

Systems with compact, ergonomic form factors are needed to enhance efficacy, compliance, and/or comfort when using non-invasive or wearable neuromodulation devices. In several embodiments, neuromodulation systems and methods are provided that enhance or inhibit nerve impulses and/or neurotransmission, and/or modulate excitability of nerves, neurons, neural circuitry, and/or other neuroanatomy that affects activation of nerves and/or neurons. For example, neuromodulation (e.g., neurostimulation) can include one or more of the following effects on neural tissue: depolarizing the neurons such that the neurons fire action potentials; hyperpolarizing the neurons to inhibit action potentials; depleting neuron ion stores to inhibit firing action potentials; altering with proprioceptive input; influencing muscle contractions; affecting changes in neurotransmitter release or uptake; and/or inhibiting firing.

In some embodiments, wearable systems and methods as disclosed herein can advantageously be used to identify whether a treatment is effective in significantly reducing or preventing a medical condition, including but not limited to tremor severity. Wearable sensors can advantageously monitor, characterize, and aid in the clinical management of hand tremor as well as other medical conditions including those disclosed elsewhere herein. Not to be limited by theory, clinical ratings of medical conditions, e.g., tremor severity, can correlate with simultaneous measurements of wrist motion using inertial measurement units (IMUs). For example, tremor features extracted from IMUs at the wrist can provide characteristic information about tremor phenotypes that may be leveraged to improve diagnosis, prognosis, and/or therapeutic outcomes. Kinematic measures can correlate with tremor severity, and machine learning algorithms incorporated in neuromodulation systems and methods as disclosed for example herein can predict the visual rating of tremor severity.

A challenge for bioelectronic and other therapies is ensuring devices are functioning normally and the patient is correctly interacting with the device. This can require in some cases real time or near real time monitoring of device function and patient-device interactions. When abnormal patient-usage or device function patterns are detected, appropriate actions can be required to minimize the impact on the patient's therapy. This is especially advantageous for prescription therapies, where interruptions to the therapy can potentially significantly impact the outcome.

Automated event log analysis can be challenging, because it requires identifying and classifying patterns in the device log events. These device logs may not be regularly occurring in time, but rather separated by any time interval. Systems and methods can be configured to analyze device-user interactions to inform device and user-specific decisions.

Neuromodulation Device

FIG. 1A illustrates a block diagram of an example neuromodulation (e.g., neurostimulation) device 100. The device 100 includes multiple hardware components which are capable of, or programmed to provide therapy across the skin of the user. As illustrated in FIG. 1A, some of these hardware components may be optional as indicated by dashed blocks. In some instances, the device 100 may only include the hardware components that are required for stimulation therapy. The hardware components are described in more detail below.

The device 100 can include two or more effectors, e.g. electrodes 102 for providing neurostimulation signals. In some instances, the device 100 is configured for transcutaneous use only and does not include any percutaneous or implantable components. In some embodiments, the electrodes can be dry electrodes. In some embodiments, water or gel can be applied to the dry electrode or skin to improve conductance. In some embodiments, the electrodes do not include any hydrogel material, adhesive, or the like.

The device 100 can further include stimulation circuitry 104 for generating signals that are applied through the electrode(s) 102. The signals can vary in frequency, phase, timing, amplitude, or offsets. The device 100 can also include power electronics 106 for providing power to the hardware components. For example, the power electronics 106 can include a battery.

The device 100 can include one or more hardware processors 108. The hardware processors 108 can include microcontrollers, digital signal processors, application specific integrated circuit (ASIC), a field programmable gate array (FPGA) or other programmable logic device, discrete gate or transistor logic, discrete hardware components, or any combination thereof designed to perform the functions described herein. In an embodiment, all of the processing discussed herein is performed by the hardware processor(s) 108. The memory 110 can store data specific to patient and rules as discussed below.

In the illustrated figure, the device 100 can include one or more sensors 112. As shown in the figure, the sensor(s) 112 may be optional. Sensors could include, for example, biomechanical sensors configured to, for example, measure motion, and/or bioelectrical sensors (e.g., EMG, EEG, and/or nerve conduction sensors). Sensors can include, for example, cardiac activity sensors (e.g., ECG, PPG), skin conductance sensors (e.g., galvanic skin response, electrodermal activity), and motion sensors (e.g., accelerometers, gyroscopes). The one or more sensors 102 may include an inertial measurement unit (IMU).

In some embodiments, the IMU can include one or more of a gyroscope, accelerometer, and magnetometer. The IMU can be affixed or integrated with the neuromodulation (e.g., neurostimulation) device 100. In an embodiment, the IMU is an off the shelf component. In addition to its ordinary meaning, the IMU can also include specific components as discussed below. For example, the IMU can include one or more sensors capable of collecting motion data. In an embodiment, the IMU includes an accelerometer. In some embodiments, the IMU can include multiple accelerometers to determine motion in multiple axes. Furthermore, the IMU can also include one or more gyroscopes and/or magnetometer in additional embodiments. Since the IMU can be integrated with the neurostimulation device 100, the IMU can generate data from its sensors responsive to motion, movement, or vibration felt by the device 100. Furthermore, when the device 100 with the integrated IMU is worn by a user, the IMU can enable detection of voluntary and/or involuntary motion of the user.

The device 100 can optionally include user interface components, such as a feedback generator 114 and a display 116. The display 116 can provide instructions or information to users relating to calibration or therapy. The display 116 can also provide alerts, such an indication of response to therapy, for example. Alerts may also be provided using the feedback generator 114, which can provide haptic feedback to the user, such as upon initiation or termination of stimulation, for reminder alerts, to alert the user of a troubleshooting condition, to perform a tremor inducing activity to measure tremor motion, among others. Accordingly, the user interface components, such as the feedback generator 114 and the display 116 can provide audio, visual, and haptic feedback to the user.

Furthermore, the device 100 can include communications hardware 118 for wireless or wired communication between the device 100 and an external system, such as the user interface device discussed below. The communications hardware 118 can include an antenna. The communications hardware 118 can also include an Ethernet or data bus interface for wired communications.

While the illustrated figure shows several components of the device 100, some of these components are optional and not required in all embodiments of the device 100. In some embodiments, a system can include a diagnostic device or component that does not include neuromodulation functionality. The diagnostic device could be a companion wearable device connected wirelessly through a connected cloud server, and include, for example, sensors such as cardiac activity, skin conductance, and/or motion sensors as described elsewhere herein.

In some embodiments, the device 100 can also be configured to deliver one, two or more of the following: magnetic, vibrational, mechanical, thermal, ultrasonic, or other forms of stimulation instead of, or in addition to electrical stimulation. Such stimulation can be delivered via one, two, or more effectors in contact with, or proximate the skin surface of the patient. However, in some embodiments, the device is configured to only deliver electrical stimulation, and is not configured to deliver one or more of magnetic, vibrational, mechanical, thermal, ultrasonic, or other forms of stimulation.

Although several neurostimulation devices are described herein, in some embodiments nerves are modulated non-invasively to achieve neuro-inhibition. Neuro-inhibition can occur in a variety of ways, including but not limited to hyperpolarizing the neurons to inhibit action potentials and/or depleting neuron ion stores to inhibit firing action potentials. This can occur in some embodiments via, for example, anodal or cathodal stimulation, low frequency stimulation (e.g., less than about 5 Hz in some cases), or continuous or intermediate burst stimulation (e.g., theta burst stimulation). In some embodiments, the wearable devices have at least one implantable portion, which may be temporary or more long term. In many embodiments, the devices are entirely wearable and non-implantable.

User Interface Device

Figure 1B:
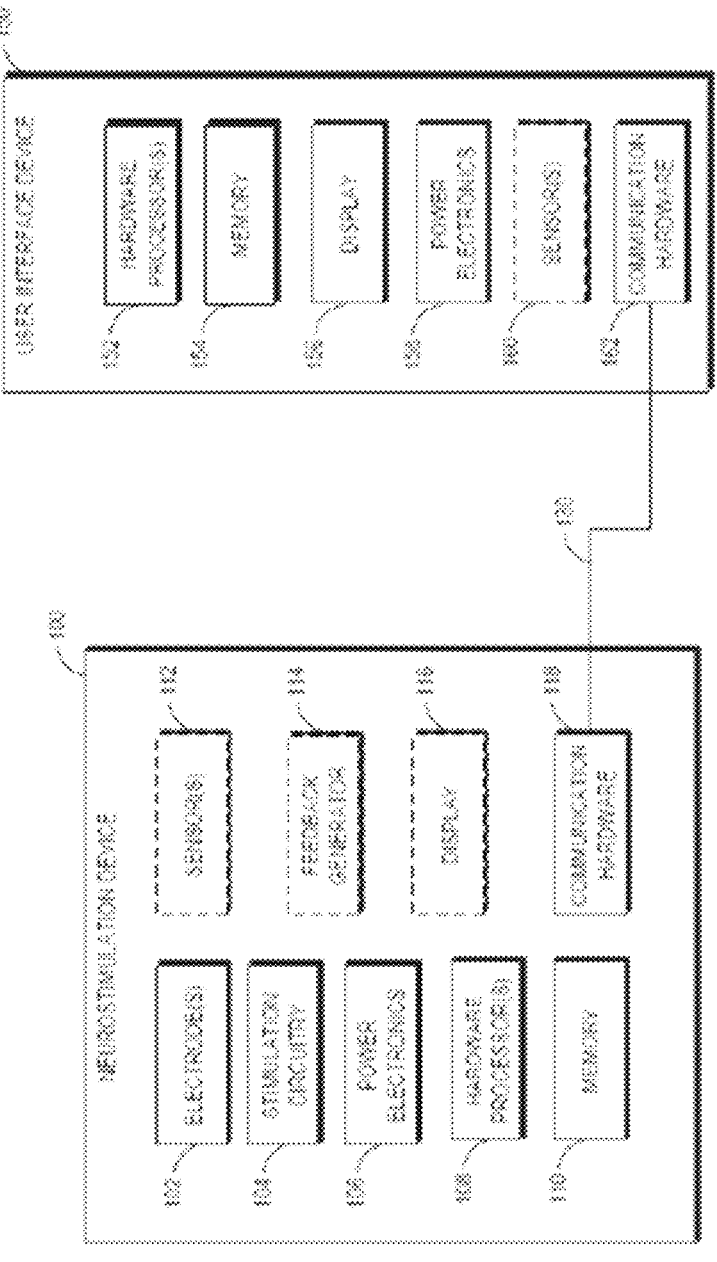
FIG. 1B illustrates a block diagram of an embodiment of a controller that can be implemented with the hardware components described with respect to FIG. 1A.

FIG. 1B illustrates communications between the neurostimulation device 100 and a user interface device 150 over a communication link 130. The communication link 130 can be wired or wireless. The neuromodulation (e.g., neurostimulation) device 100 is capable of communicating and receiving instructions from a user interface device 150. The user interface device 150 can include a computing device. In some embodiments, the user interface device 150 is a mobile computing device, such as a mobile phone, a smartwatch, a tablet, or a wearable computer. The user interface device 150 can also include server computing systems that are remote from the neurostimulation device. The user interface device 150 can include hardware processor(s) 152, a memory 154, display 156, and power electronics 158. In some embodiments, a user interface device 150 can also include one or more sensors, such as sensors described elsewhere herein. Furthermore, in some instances, the user interface device 150 can generate an alert responsive to device issues or a response to therapy. The alert may be received from the neurostimulation device 100.

In additional embodiments, data acquired from the one or more sensors 102 is processed by a combination of the hardware processor(s) 108 and hardware processor(s) 152. In further embodiments, data collected from one or more sensors 102 is transmitted to the user interface device 150 with little or no processing performed by the hardware processors 108. In some embodiments, the user interface device 150 can include a remote server that processes data and transmits signals back to the device 100 (e.g., via the cloud).

Figure 1C:
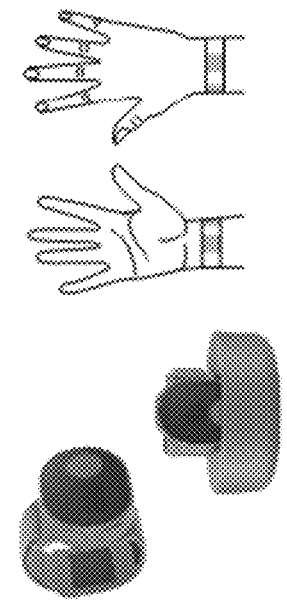
FIG. 1C schematically illustrates an embodiment of a neuromodulation device and base station.

FIG. 1C schematically illustrates a neuromodulation device and base station. The device can include a stimulator and detachable band including two or more working electrodes (positioned over the median and radial nerves) and a counter-electrode positioned on the dorsal side of the wrist. The electrodes could be, for example, dry electrodes or hydrogel electrodes. The base station can be configured to stream movement sensor and usage data on a periodic basis, e.g., daily and charge the device. The device stimulation bursting frequency can be calibrated to a lateral postural hold task "wing-beating" or forward postural hold task for a predetermined time, e.g., 20 seconds for each subject. Other non-limiting examples of device parameters can be as disclosed elsewhere herein.

In some embodiments, stimulation may alternate between each nerve such that the nerves are not stimulated simultaneously. In some embodiments, all nerves are stimulated simultaneously. In some embodiments, stimulation is delivered to the various nerves in one of many bursting patterns. The stimulation parameters may include on/off, time duration, intensity, pulse rate, pulse width, waveform shape, and the ramp of pulse on and off. In one preferred embodiment the pulse rate may be from about 1 to about 5000 Hz, about 1 Hz to about 500 Hz, about 5 Hz to about 50 Hz, about 50 Hz to about 300 Hz, or about 150 Hz. In some embodiments, the pulse rate may be from 1 kHz to 20 kHz. A preferred pulse width may range from, in some cases, 50 to 500 us (micro-seconds), such as approximately 300 us. The intensity of the electrical stimulation may vary from 0 mA to 500 mA, and a current may be approximately 1 to 11 mA in some cases. The electrical stimulation can be adjusted in different patients and with different methods of electrical stimulation. The increment of intensity adjustment may be, for example, 0.1 mA to 1.0 mA. In one preferred embodiment the stimulation may last for approximately 10 minutes to 1 hour, such as approximately 10, 20, 30, 40, 50, or 60 minutes, or ranges including any two of the foregoing values. In some embodiments, a plurality of electrical stimuli can be delivered offset in time from each other by a predetermined fraction of multiple of a period of a measured rhythmic biological signal such as hand tremor, such as about ¼, ½, or ¾ of the period of the measured signal for example. Further possible stimulation parameters are described, for example, in U.S. Pat. No. 9,452,287 to Rosenbluth et al., U.S. Pat. No. 9,802,041 to Wong et al., PCT Pub. No. WO 2016/201366 to Wong et al., PCT Pub. No. WO 2017/132067 to Wong et al., PCT Pub. No. WO 2017/023864 to Hamner et al., PCT Pub. No. WO 2017/053847 to Hamner et al., PCT Pub. No. WO 2018/009680 to Wong et al., and PCT Pub. No. WO 2018/039458 to Rosenbluth et al., each of the foregoing of which are hereby incorporated by reference in their entireties.

Controller

Figure 2:
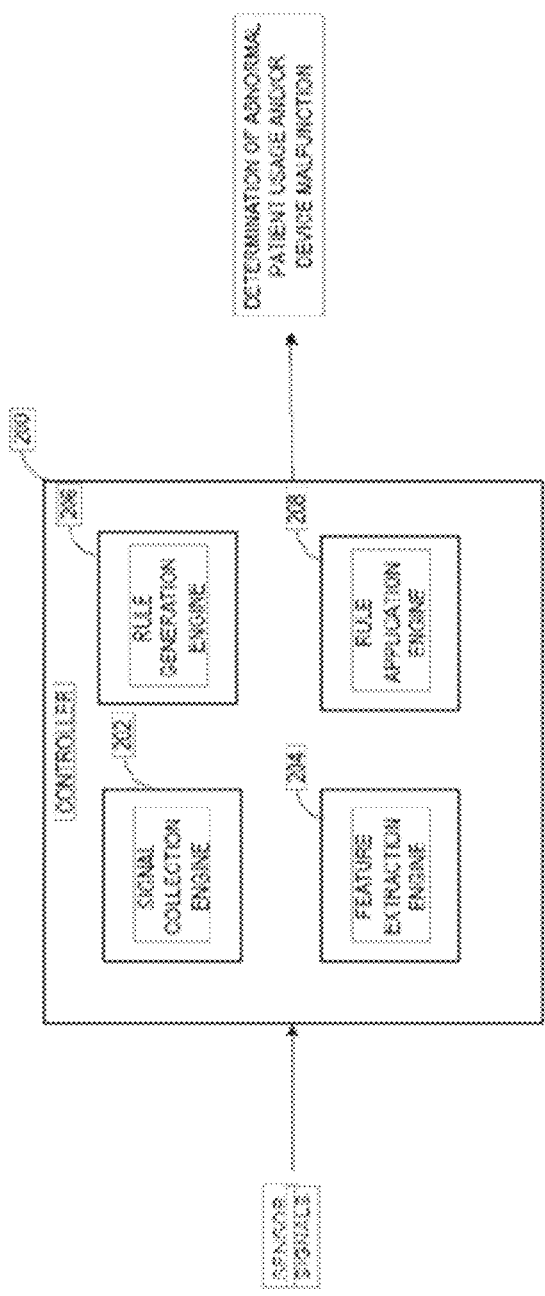
FIG. 2 illustrates a block diagram of an embodiment of a controller that can be implemented with the hardware components described with respect to FIG. 1A or 1B.

FIG. 2 illustrates a block diagram of an embodiment of a controller 200 that can be implemented with the hardware components described above with respect to FIGS. 1A-1C. The controller 200 can include multiple engines for performing the processes and functions described herein. The engines can include programmed instructions for performing processes as discussed herein for detection of input conditions and control of output conditions. The engines can be executed by the one or more hardware processors of the neuromodulation (e.g., neurostimulation) device 100 alone or in combination with the patient monitor 150. The programming instructions can be stored in a memory 110. The programming instructions can be implemented in C, C++, JAVA, or any other suitable programming languages. In some embodiments, some or all of the portions of the controller 200 including the engines can be implemented in application specific circuitry such as ASICs and FPGAs. Some aspects of the functionality of the controller 200 can be executed remotely on a server (not shown) over a network. While shown as separate engines, the functionality of the engines as discussed below is not necessarily required to be separated. Accordingly, the controller 200 can be implemented with the hardware components described above with respect to FIGS. 1A-1C.

The controller 200 can include a signal collection engine 202. The signal collection engine 202 can enable acquisition of raw data from sensors embedded in the device, including but not limited to accelerometer or gyroscope data from the IMU 102. In some embodiments, the signal collection engine 202 can also perform signal preprocessing on the raw data. Signal preprocessing can include noise filtering, smoothing, averaging, and other signal preprocessing techniques to clean the raw data. In some embodiments, portions of the signals can be discarded by the signal collection engine 202.

The controller 200 can also include a feature extraction engine 204. The feature extraction engine 204 can extract relevant features from the signals collected by the signal collection engine 202. The features can be in time domain and/or frequency domain. For example, some of the features can include amplitude, bandwidth, area under the curve (e.g., power), energy in frequency bins, peak frequency, ratio between frequency bands, and the like. The features can be extracted using signal processing techniques such as Fourier transform, band pass filtering, low pass filtering, high pass filtering and the like.

The controller can further include a rule generation engine 206. The rule generation engine 206 can use the extracted features from the collected signals and determine rules that correspond to past, current, imminent, or future device malfunction and/or abnormal patient usage of the device. The rule generation engine 206 can automatically determine a correlation between specific extracted features and device malfunction and/or abnormal patient usage of the device. Device malfunction events can include, for example, poor connection quality, sensor failure, stimulation failure, and others. Abnormal patient usage of the device can include, for example, repetitive or excessive button or other control presses, patient-initiated termination of therapy sessions, anomalous adjustment of stimulation amplitude, and the like.

The device can also identify potential undesirable user experiences using tremor features assessed from kinematic measurements and patient usage logs from the device where undesirable user experiences can include but are not limited to device malfunctions and adverse events such as skin irritation or burn; and predict patient or customer satisfaction (e.g., net promoter score) based on patient response or other kinematic features from measured tremor motion.

FIG. 3 is a table matrix indicating various non-limiting advantages of systems and methods as disclosed herein according to some embodiments, including in the customer success, clinical, R&D, and data science areas. Advantages can include, for example, enhancing patient satisfaction, maximizing clinical trial success, enhancing the user experience, and enhancing product and services. The systems and methods can be utilized to identify which patients are having issues with the device; if the patient is compliant with using the device as recommended; and/or to provide user experience feedback. Systems and methods can also be utilized to identify or predict devices having or will have issues; whether the device is functioning normally to deliver therapy; what errors are occurring in the device; and/or is the device logging data normally. Systems and methods can also be utilized to result in patient contact for a proactive product replacement/upgrade; efficiently identify and fix issues and/ or provide patient education; and/or provide accurate insights from the data.

Figure 4:
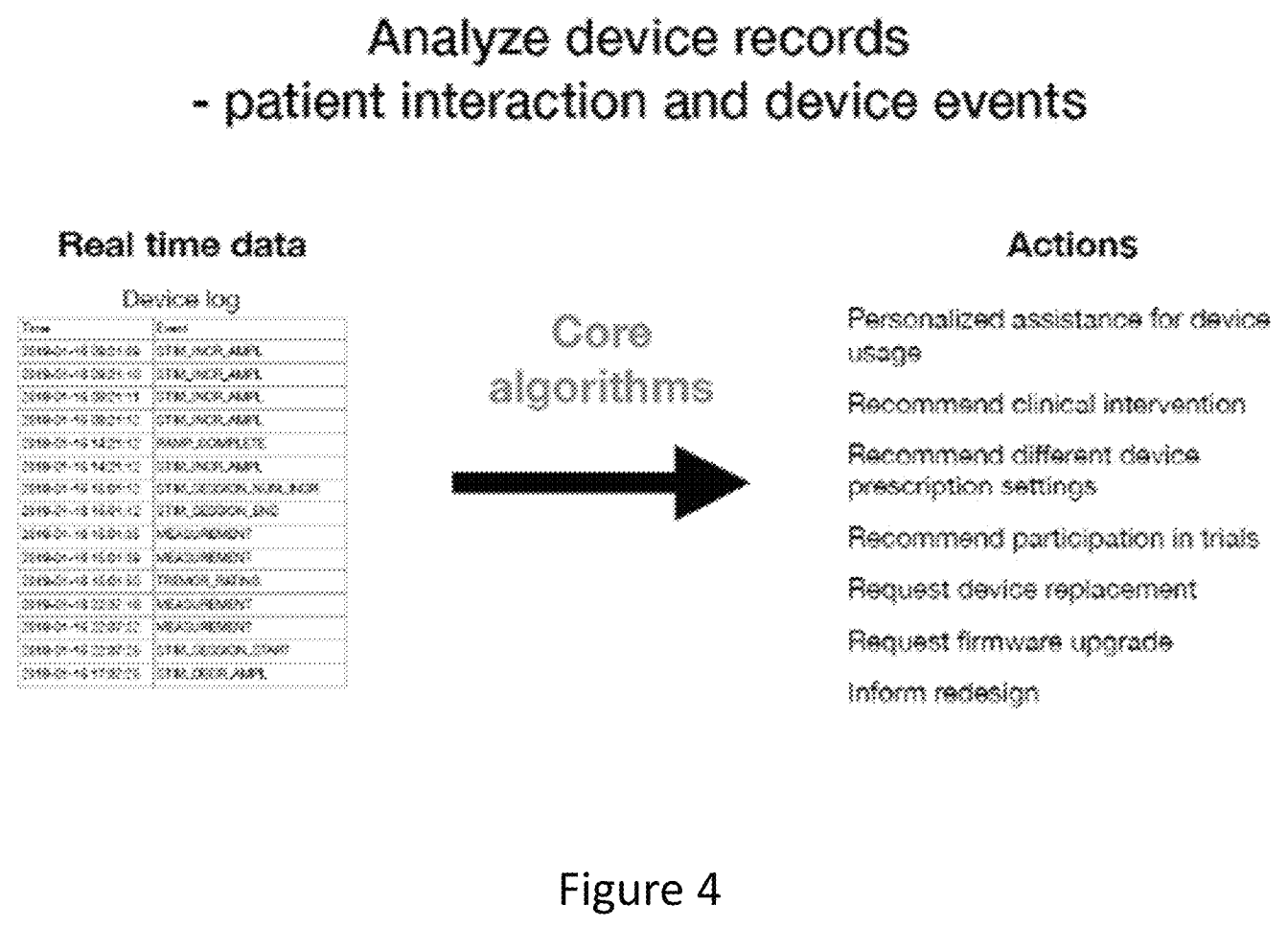

FIG. 4 illustrates a schematic illustrating examples of system and method functionality of some embodiments, which can include analysis of device records, and patient interaction and device events from device logs can be input into a controller in real-time, near real-time, or later in order to personalize assistance for device usage; recommend clinical intervention; recommend different device prescription settings; recommend participation in trials; request device replacement; request firmware upgrades; and inform possible re-designs, for example.

In some embodiments, real-time assessment can be within about 10 seconds, 5 seconds, or 1 second of an event occurring. In some embodiments, near real-time assessment can be within about 24 hours, 12 hours, 6 hours, 3 hours, 2 hours, 1 hour, 45 minutes, 30 minutes, 15 minutes, 10 minutes, 5 minutes, 4 minutes, 3 minutes, 2 minutes, 1 minute, 30 seconds, or 15 seconds of an event occurring, or ranges including any two of the foregoing values.

In some embodiments, monitoring systems and methods can utilize a plurality of engines. Any device log can be used, for example logs of patient-device interactions or internal device function records.

In some embodiments, anomaly detection can be performed via a controller configured to execute an Anomalous Sequence Detection Algorithm (ASDA), which can analyze a set of training device log events to create a model of log patterns, corresponding to the expected pattern. The controller can also be configured to execute an Event Sequence Classification Algorithm (ESCA), which classifies event sequences. This can then be used to identify groups of event sequences corresponding to classes of patterns. Each group of patterns can be automatically inspected, or manually inspected by a trained operator to assign a human-readable label.

Some system advantages, according to several embodiments, include the ability to predict whether a new, previously unobserved sequence of events is unexpected or anomalous according to the model. For example, ASDA can predict the likelihood of observing a new sequence of events, and ESCA classifies which group the new sequence of events belongs to.

As one example, a new sequence of events is predicted to be unlikely during normal use (e.g., probability of less than a certain threshold, such as, for example, about or less than about 1:100, 1:500, 1:1,000, or less) and can be classified to a group of events with a desired label, e.g., the label "device connection error".

In some embodiments, ASDA involves a Markov chain (e.g., a modified continuous-time Markov chain), and can be configured to model the probability of observing a first event A, then a second event B (as well as subsequent third event C, fourth event D, etc.) at a given time interval. A Markov chain is a stochastic model describing a sequence of possible events in which the probability of each event depends only on the state attained in the previous event. The time interval can be first converted into a time bin on a logarithmic scale (0 s, 1 s, 2 s, 4 s, 8 s, 16 s, etc.). A Laplace or other estimator can then be utilized to minimize the influence of null count events on probability calculations. The likelihood of observing a n-length sequence is the prior probability p (no) multiplied by the probability of subsequent event transitions, obtained from the model using, for example, look up or interpolation.

ESCA can involve a collection of short event segments. These segments can be derived from entire event logs that are separated into smaller segments (e.g., segments with 1, 2, 3, 4, 5, 6, 7, 8, 9, 10 events or more or less, or ranges including any two of the foregoing values). The input can be the numerically encoded identifier of each event interleaved by the time bin identity of the log transformed time interval between the surrounding events. Each segment can have a corresponding likelihood which can be calculated by ASDA.

The segments can then be fed into an artificial neural network (e.g., self-organizing map). This is an unsupervised method for classification, and can produce a low-dimensional (e.g., two-dimensional), discretized representation of the input space of the training samples (e.g., map), and perform dimensionality reduction. In some embodiments, the method for classification is not supervised. Self-organizing maps differ from other artificial neural networks as they apply competitive learning as opposed to error-correction learning (such as backpropagation with gradient descent), and in the sense that they use a neighborhood function to preserve the topological properties of the input space. After the model is trained, each neuron in the map can have a corresponding weight, which indicates a specific pattern it detects. It also has a corresponding probability calculated by averaging the ASDA calculated likelihood of the segments that were selected by the neuron. Thus, each neuron and the group it represents is assigned a likelihood.

In some embodiments, patient support and device warranty can be provided. This system can be used to monitor and automatically flag scenarios that needs customer outreach.

Some non-limiting examples include the following. In some embodiments, ASDA indicates patient usage patterns continuously show sequences of button presses that are highly unusual under normal usage. ESCA identifies the button presses are occurring before the start of a therapy session, indicating the patient has difficulty starting a therapy session. This can be communicated remotely to a third party, such as the customer success team for example, which can contact the patient with instructions for using the device correctly. In some embodiments, the system will identify a pattern of button presses, such as, for example, about or at least about 2, 3, 4, 5, 6, 7, 8, 9, 10, or more (or ranges including any of the foregoing values) within a specified time interval, such as, for example, within about 5, 4, 3, 2, or 1 minute, or 30 seconds, 20 seconds, 15 seconds, 10 seconds, 5 seconds, or less (or ranges including any of the foregoing values).

In another embodiment, ASDA and ESCA indicate the device is beginning to malfunction, potentially affecting therapy delivery. A third party, such as a customer success team can be alerted remotely to send a replacement device before actual device failure.

In another embodiment, during development testing/clinical trials, ASDA and ESCA analyze the device logs and identifies unusual sequences associated with a particular event. This can be used to debug and release new updates to device firmware.

Any sequence of events with corresponding timestamps can be processed using the ASDA/ESCA platform into order to provide insight on sequence patterns.

Figure 5:
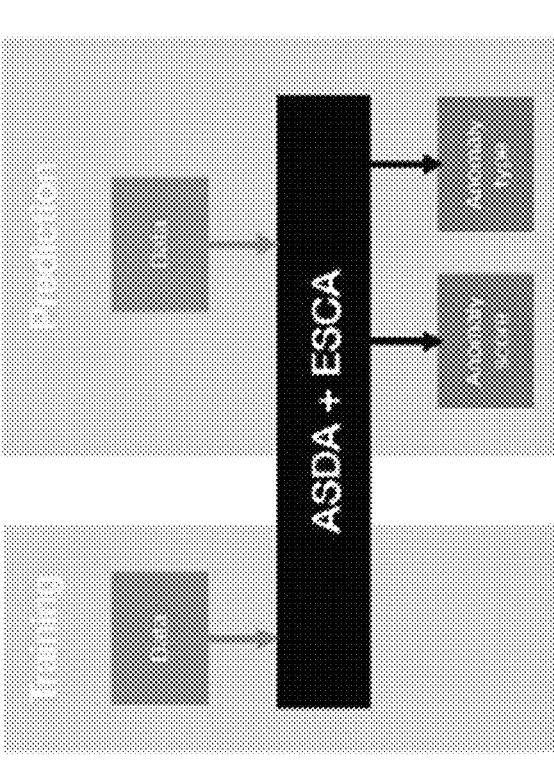
FIG. 5 illustrates a schematic indicating how device log analysis algorithms can be utilized to detect and classify anomalous events, utilizing a controller configured for anomalous sequence detection and event sequence classification as disclosed elsewhere herein.
Figure 6A:
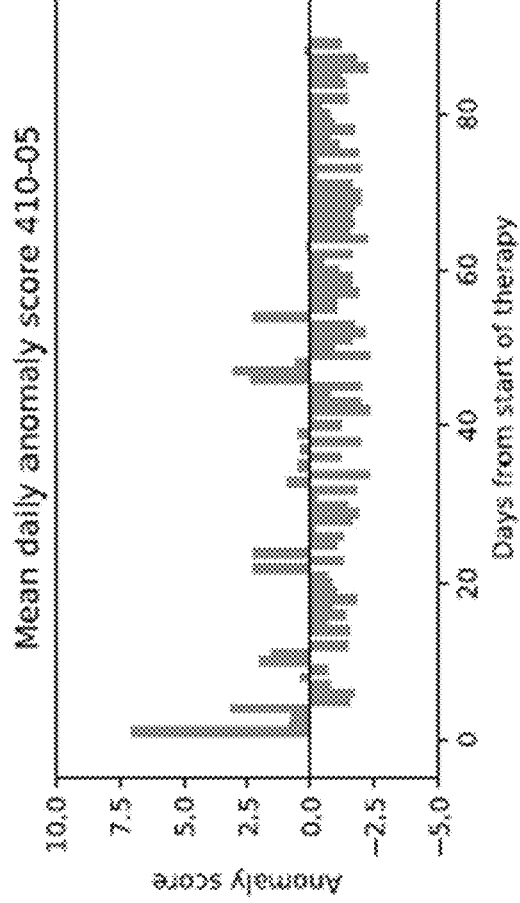
FIGS. 6A to 6D schematically illustrates example results using ASDA, including device log data over time that can be utilized to calculate an anomaly score and detect a type of anomaly.
Figure 6B:
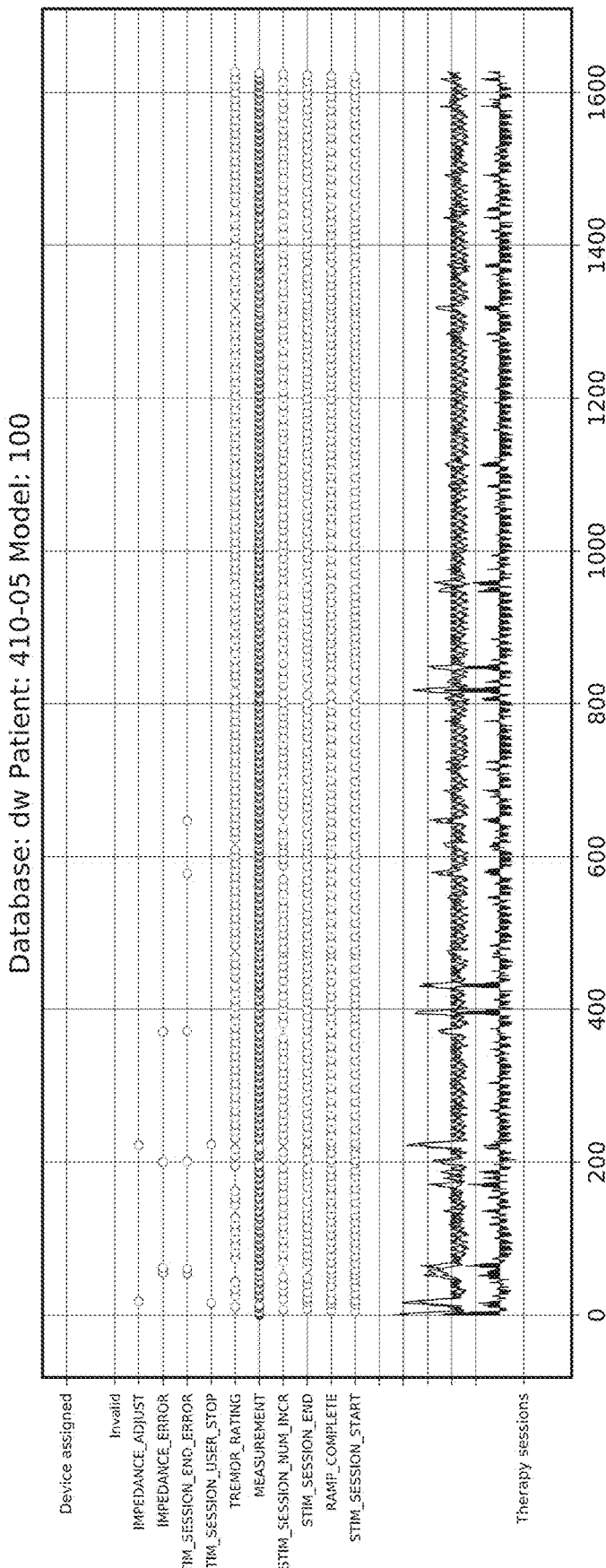
Figure 6C:
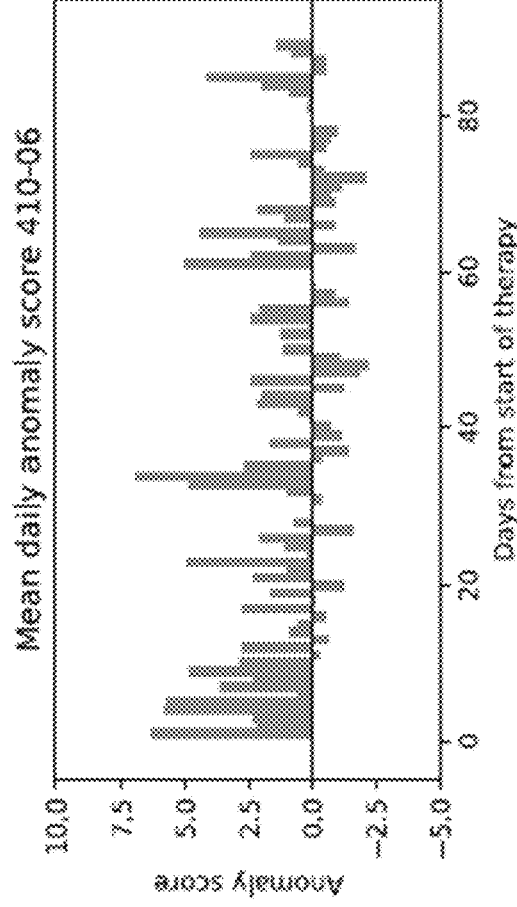
Figure 6D:
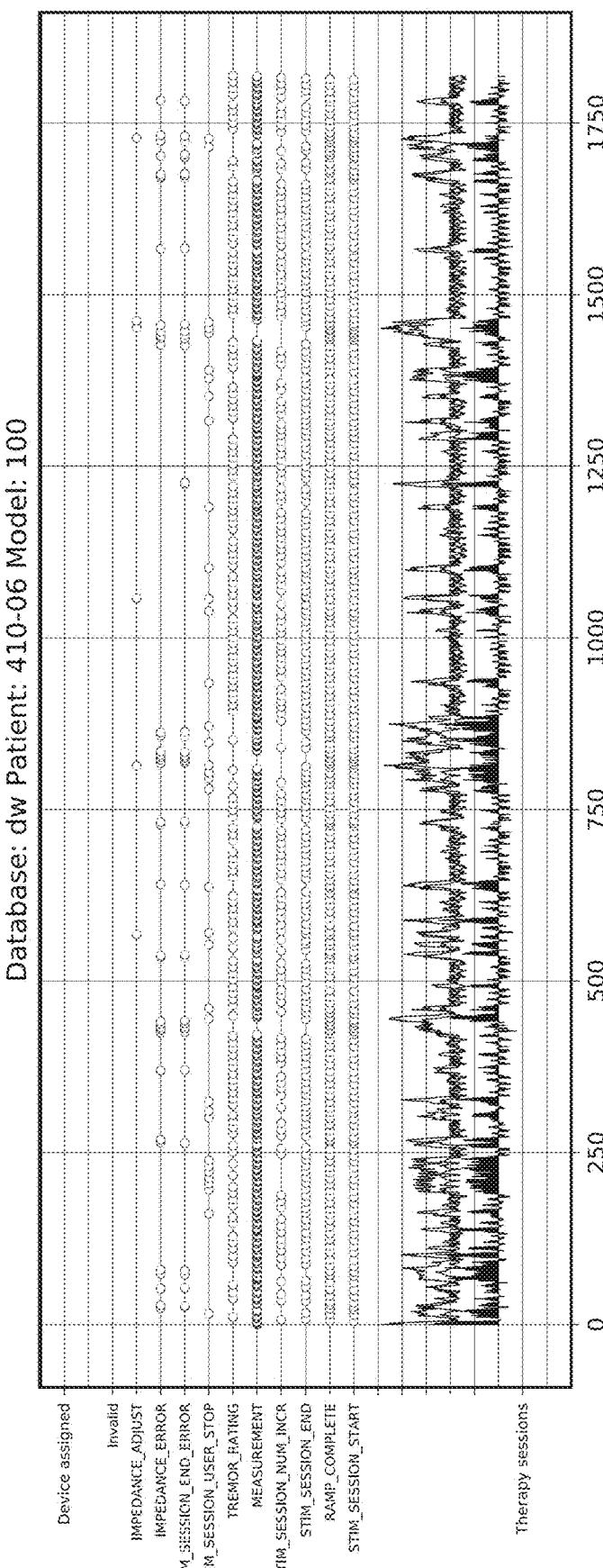

FIG. 5 illustrates a schematic indicating how device log analysis algorithms can be utilized to detect and classify anomalous events, utilizing a controller configured for anomalous sequence detection and event sequence classification as disclosed elsewhere herein. The data can be utilized to determine an anomaly score and/or identify the type of anomaly.

FIGS. 6A-6D schematically illustrates example results using ASDA, including device log data over time that can be utilized to calculate an anomaly score and detect a type of anomaly. Alerts can be transmitted to a third party depending on anomaly score thresholds and/or the type of anomaly, which can include anomalies in measured impedance values, current delivery, tremor frequency values, device or user-aborted stimulation sessions, button or other control presses, and the like.

Figure 7:
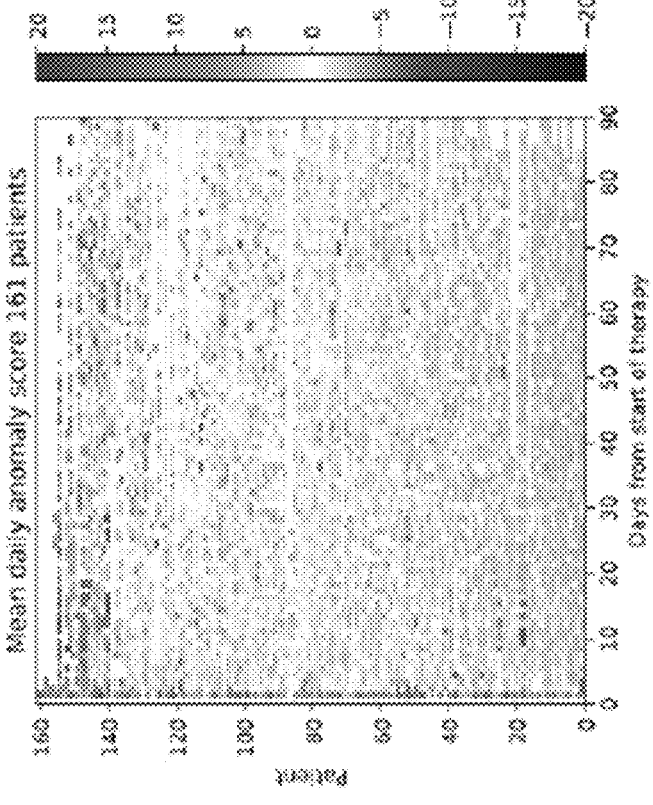
FIG. 7 schematically illustrates scatter plot results for a set of patients, and also measuring an anomaly score.
Figure 7:
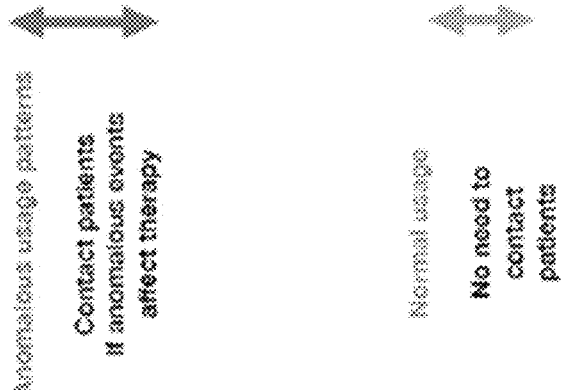

FIG. 7 schematically illustrates scatter plot results for a set of 161 patients, with the patient number on the Y axis and days from the start of therapy on the X axis vs. the anomaly score (listed as a range of −20 to 20). Normal usage patterns, such as in the lower half of the graph with low anomaly scores indicate that patients do not need to be contacted, while anomalous usage patterns, such as in the upper half of the graph with high anomaly scores indicate that patients may be contacted if anomalous events affect therapy.

Figure 8A:
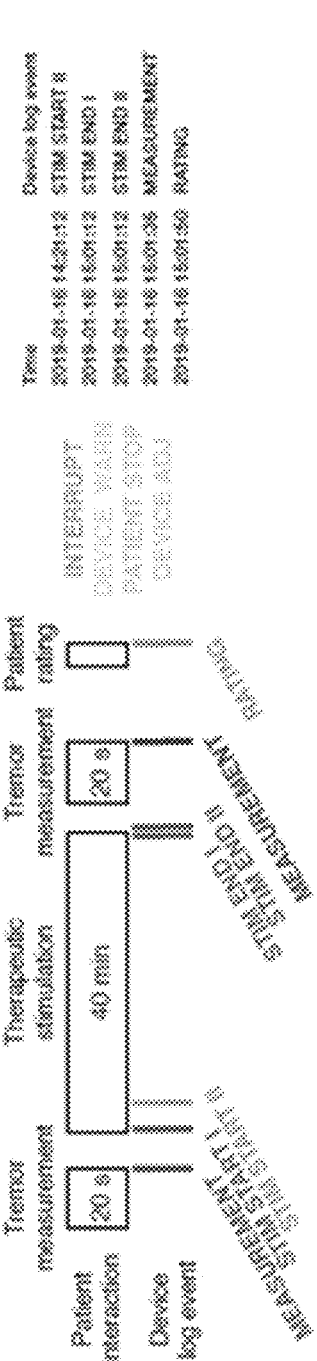
FIG. 8A schematically illustrates a therapy session using a neuromodulation device, with corresponding device log events over time.

FIG. 8A schematically illustrates a therapy session using a neuromodulation device, with corresponding device log events over time, including tremor measurements (e.g., frequency sensing), stimulation starts, stimulation cessations, and patient rating, as well as interruptions, device warnings, patient stopping the therapy, and device adjustments.

Figure 8B:
FIG. 8B illustrates example data collection sequence with event markers.
Figure 8B:
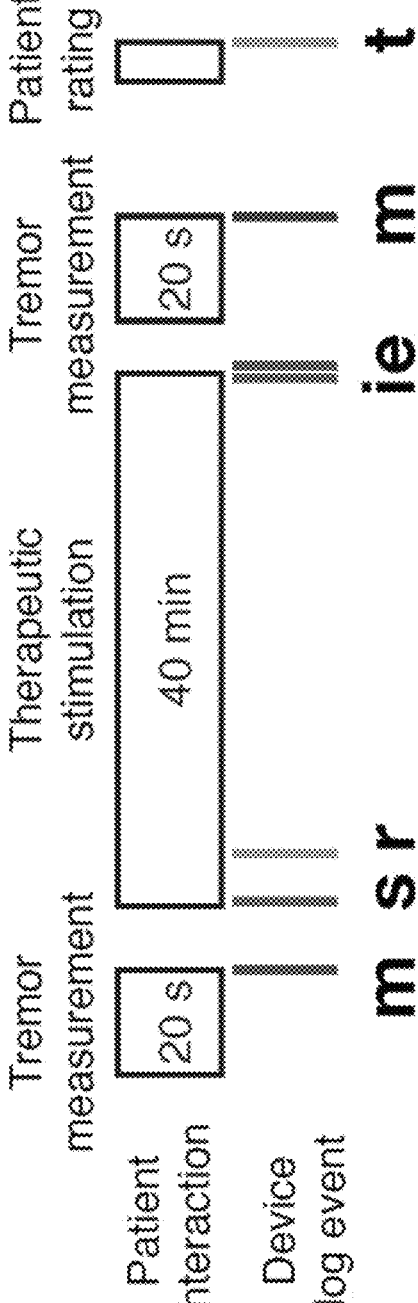

FIGS. 8B and 8C illustrate an example of data collection sequence that is used to log device events. As shown in FIG. 8B, the controller 200 can use markers that indicate particular events related to device settings, function, and/or therapy. In some instances, the controller 200 stores these markers with a time stamp as shown in FIG. 8C. The time stamp can correspond to an end or a completion of an event. The completion may refer to a successful or an anomalous end to an event. In some instances, the controller 200 can also store additional data, such as the start time or duration of a particular event. The controller 200 can store these markers along with time stamps in a device log, which may be a text file or other database format.

Figure 9A:
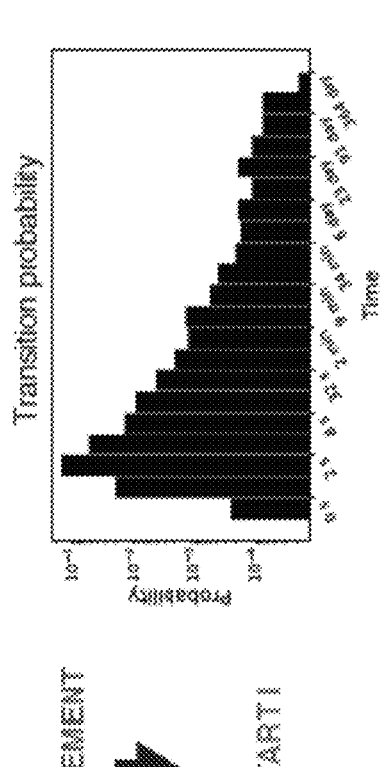
FIG. 9A schematically illustrates a device log event sequence model, including continuous time Markov chains in bar graph form.

FIG. 9A schematically illustrates a device log event sequence model, including continuous time Markov chains in bar graph form, and illustrating a gradual reduction in transition probability beyond 2 seconds in time.

Figure 9B:
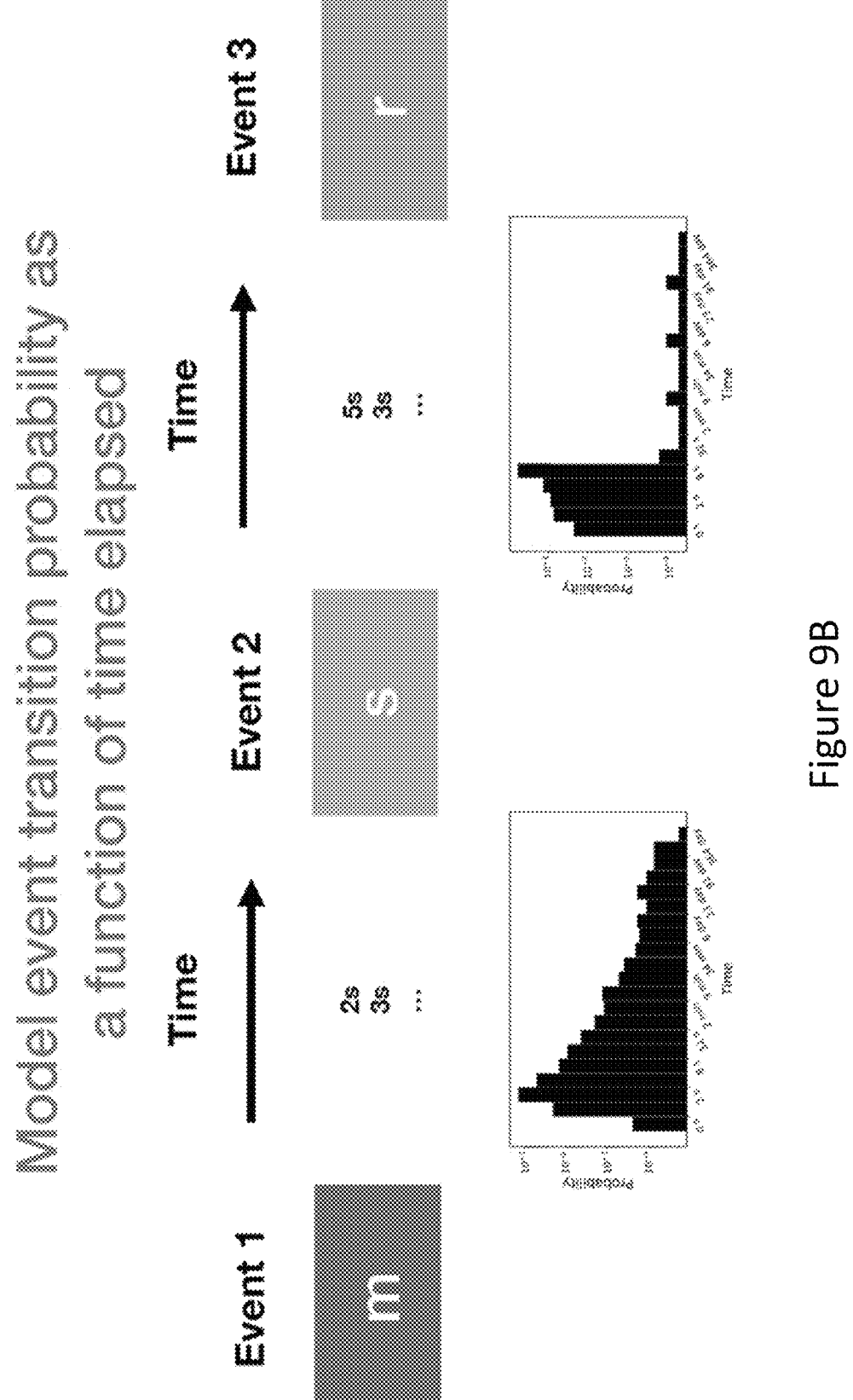
FIG. 9B illustrates example transition probabilities between events and particular event sequences.

FIG. 9B illustrates example transition probabilities between events and particular event sequences. By knowing these probabilities, the controller 200 can identify unusual or abnormal event sequences from device logs that may have thousands of entries. In some instances, the rules for what constitutes an abnormal event sequence is not predetermined. The controller 200 can automatically determine these rules or patterns as will be described in more detail below. The probabilities may also be a function of time in addition to transition between two events.

The log can store data over multiple days and may have only access to certain outcomes. Patterns from these stored logs may not be easily discernable. For example, many patients deal with short stimulation sessions where the device may turn off prematurely. This may be a result of them not wearing the band properly. In some cases, users may be performing some steps, but not all, such as skipping certain measurement steps. These measurement steps may be important in a clinical trial. Accordingly, the embodiments described herein enable early intervention by identifying certain patterns from the device log. These patterns may not be easily identifiable based on visual inspection of the device log. Identifying these patterns can improve treatment and the use of neurostimulation device.

Figure 9C:
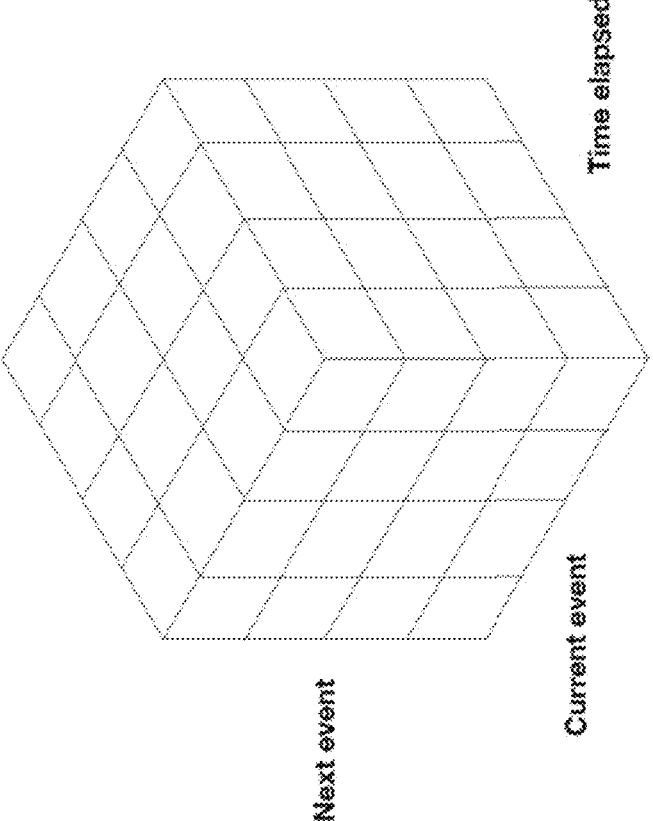
FIG. 9C illustrates a visual representation of an array of numbers representing a probability model.
Figure 9C:
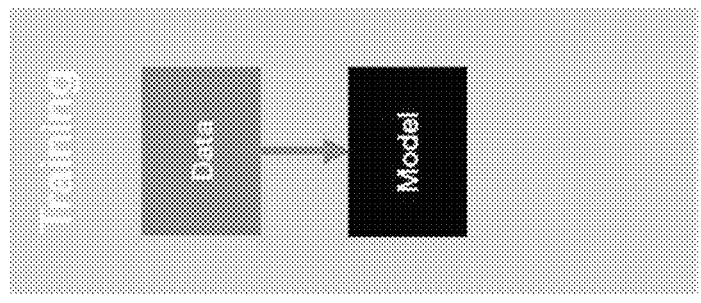

FIG. 9C illustrates a visual representation of an array of numbers representing a probability model. The probabilities can be stored as a function of current event, next event and the time elapsed between the current event and the next event. Accordingly, for any sequence in the log data, the probability between two events based on the elapsed time can be determined from this stored Markov model. Probabilities can also be multiplied together based on combining multiple events.

Figure 9D:
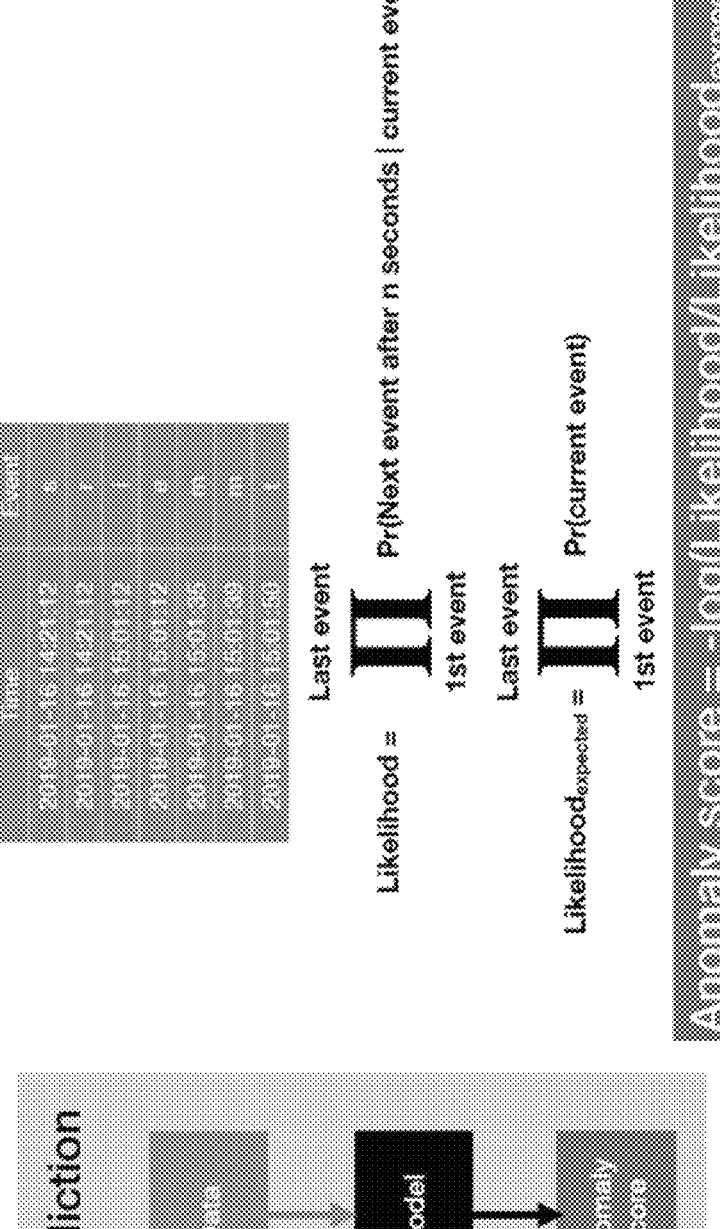
FIG. 9D illustrates a formula that is used to calculate an anomaly score for a particular sequence of events.

FIG. 9D illustrates a formula that is used to calculate an anomaly score for a particular sequence of events based on the Markov model illustrated in FIG. 9C. The anomaly score is related to a logarithm of the likelihood of a particular event sequence normalized by that event occurring just by chance. A score of zero or less based on the illustrated formula indicates that the event was expected. In contrast, a score that is greater than zero indicates that the event is abnormal. While the specific calculation of the anomaly score is illustrated, other calculation models can be used. The anomaly score represents the degree of deviation from expectation of a particular event transition.

Figure 9E:
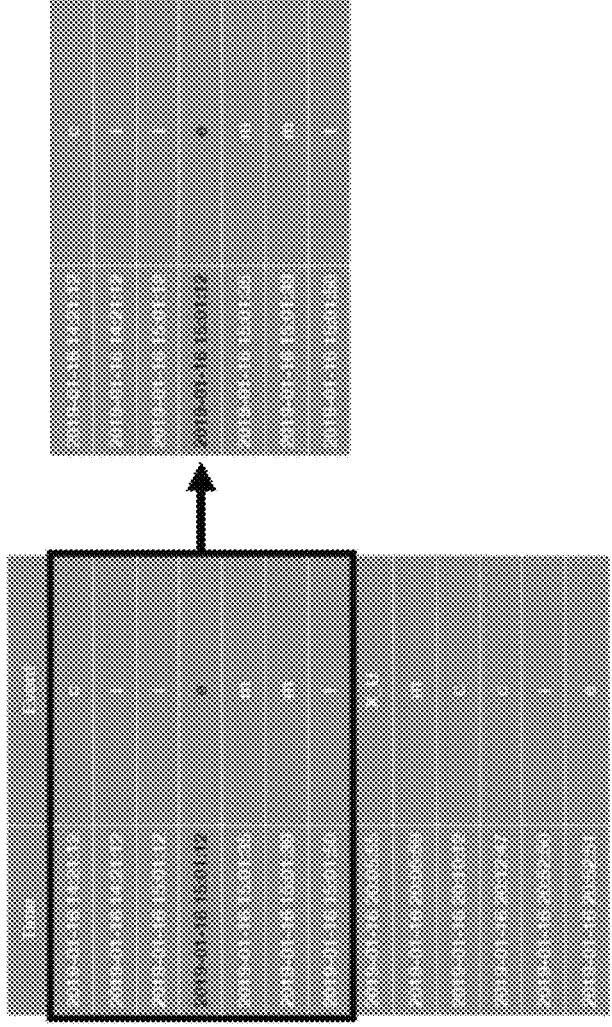
FIG. 9E shows a snippet of an example event log with time stamps and corresponding event markers.

FIG. 9E shows a snippet of an example event log with time stamps and corresponding event markers. The event log can be broken up in groups of event sequences. In the illustrated embodiment, a group size of seven is selected. Other group sizes can also be used. The controller 200 can divide the entire event log into groups based on the selected size. For each group, the controller 200 can calculate an anomaly score.

Figure 9F:
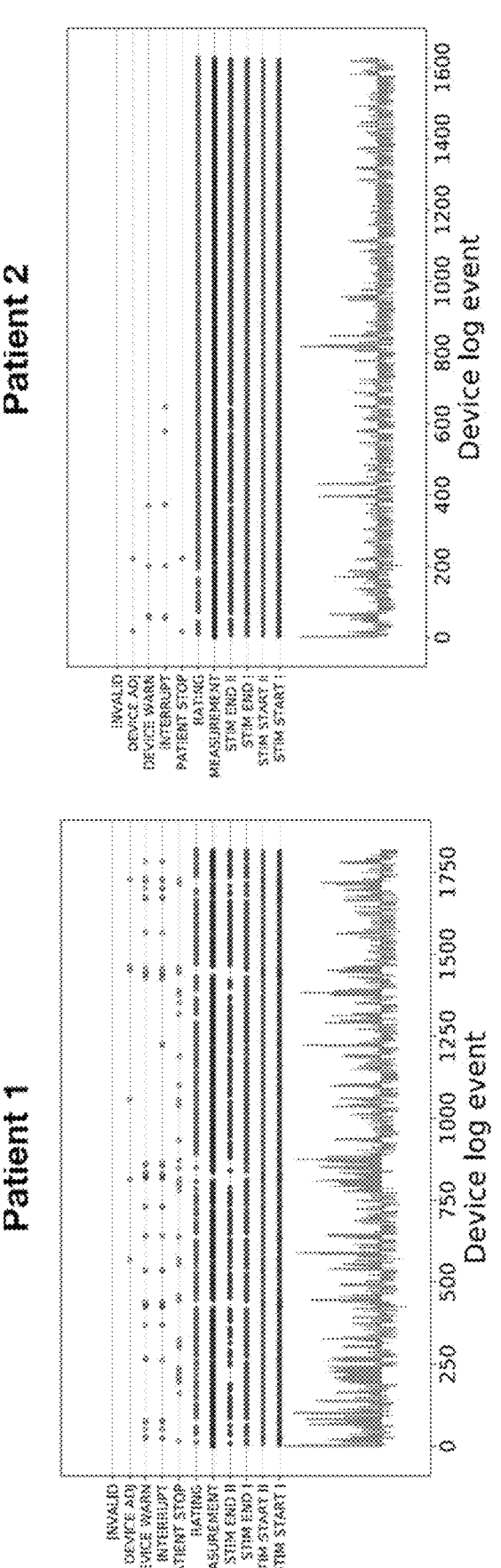
FIG. 9F shows calculated anomaly scores over time of two patients.

FIG. 9F shows calculated anomaly scores over time for two patients. The first patient has more peaks greater than 0, which indicates that Patient 1 has an unusual usage of the device as compared to Patient 2, who has less peaks greater than 0.

Figure 9G:
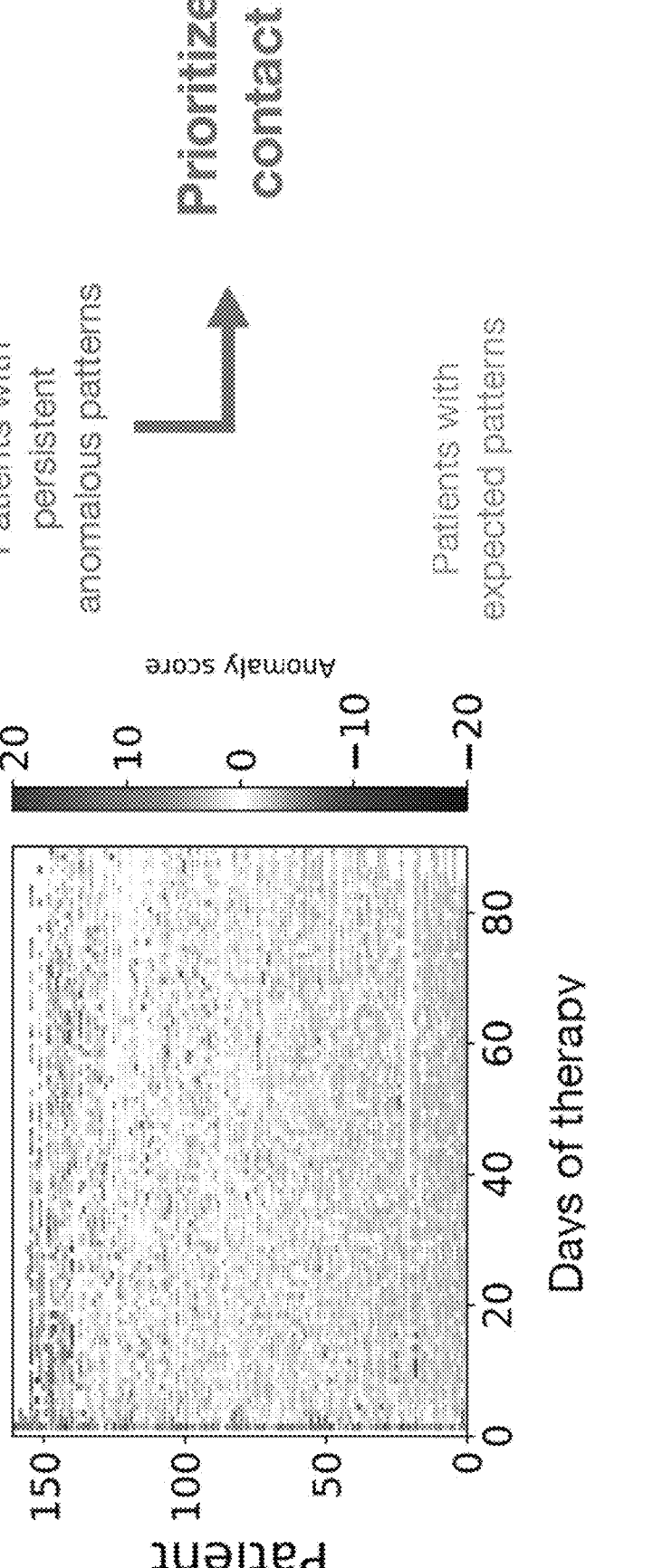
FIG. 9G illustrates a heat map of patients and corresponding anomaly scores over time.

FIG. 9G illustrates a heat map of patients and corresponding anomaly scores over time. Some patients show high anomaly score from early usage and that is consistent over several days (see for example, patients in the range of 100-150). In some instances, the controller 200 can automatically determine that the patients with continuous anomalous patterns should be prioritized for contact.

Figure 10:
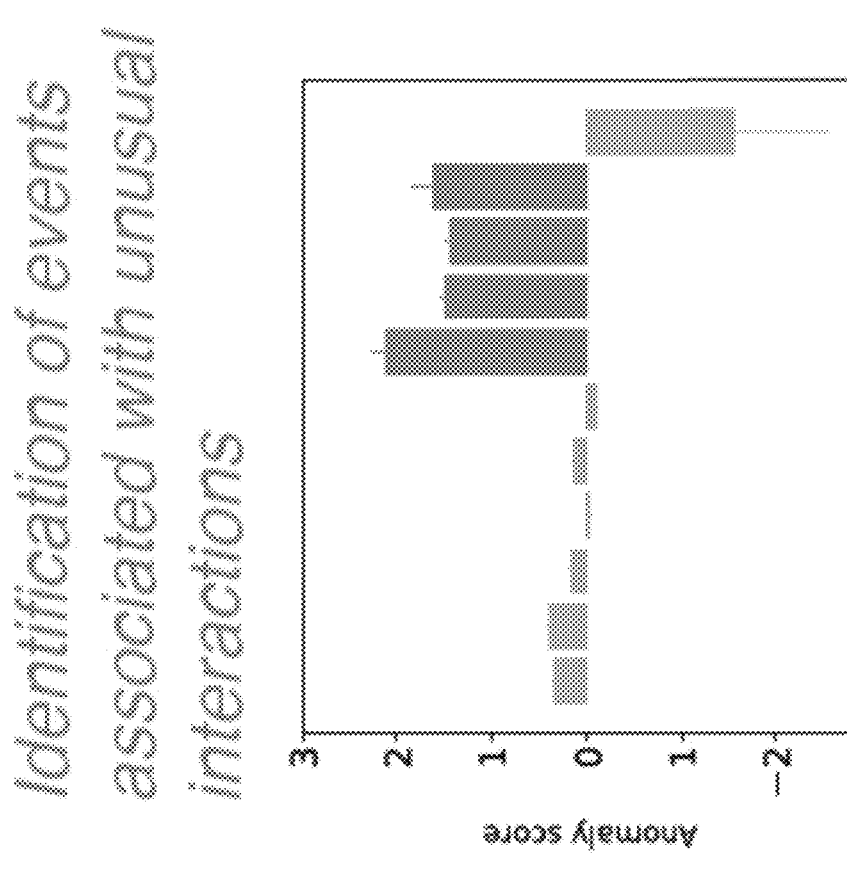
FIG. 10 schematically illustrates a bar graph illustrating identification of events associated with unusual interactions.

FIG. 10 schematically illustrates a bar graph illustrating identification of events associated with unusual interactions (e.g., patient-initiated cessation of therapy, device interruptions and warnings, etc.), resulting in an increased anomaly score.

Figure 11:
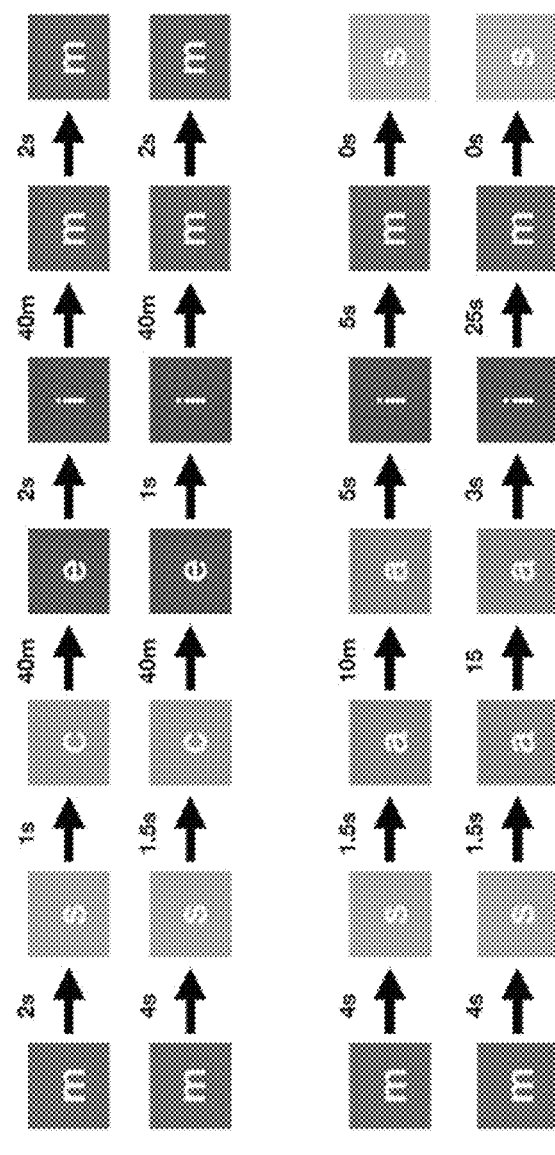
FIG. 11 illustrates two types of sequences that can be grouped together.

In some instances, there could be thousands of patients using the neurostimulation device. It may be very difficult to call them all if there are issues with their use of the neurostimulation device. Accordingly, the controller 200 can identify which patients need attention. The controller 200 can identify unusual patterns. These patterns are very difficult to ascertain manually through visual inspection. The logs can be very long with thousands of entries per patient and thousands of patients monitored at any given time. Furthermore, the patterns are not consistent or easily identifiable. There could be variations in both time and sequences. Accordingly, it may be difficult to group patterns through visual inspection. FIG. 11 illustrates two types of sequences that can be grouped together. The first two sequences are similar and the bottom two sequences are similar to each other. An example process for determining these groupings of sequences automatically is described below.

Figure 12:
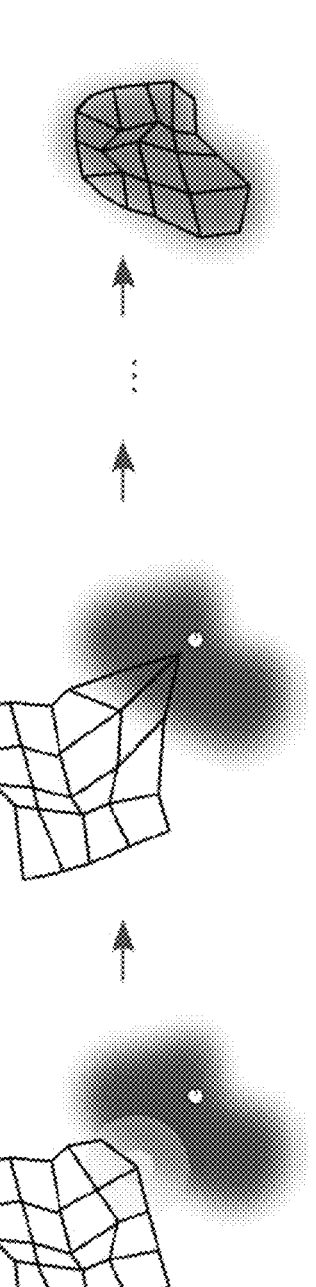
FIG. 12 an example of an unsupervised neural network.

In some instances, an unsupervised neural network as seen in FIG. 12 can be used to identify patterns. Other type of classification algorithms include clustering (k-means, Expectation Maximization and Hierarchical Clustering), ensemble methods (Classification and Regression Tree variants and Boosting), instance-based (k-Nearest Neighbor, Self-Organizing Maps and Support Vector Machines), regularization (Elastic Net, Ridge Regression and Least Absolute Shrinkage Selection Operator), and dimensionality reduction (Principal Component Analysis variants, Multidimensional Scaling, Discriminant Analysis variants and Factor Analysis).

Figure 13:
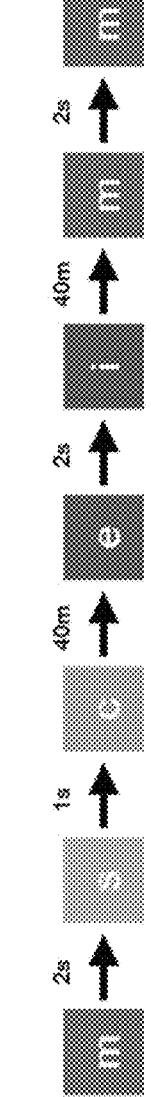
FIG. 13 illustrates an embodiment of encoding a particular sequence in format that is suitable for training.

Prior to using any classification scheme discussed above, the controller 200 may need to encode data in a format that is usable by a particular classifier. Input to the detection and classification algorithm can include, numerically transformed and untransformed device logging descriptions, associated timestamps and additional metadata. FIG. 13 illustrates an example of how to encode a particular sequence in a format that is suitable for training a classifier. The problem of encoding sequence of markers separated by time can be challenging. In the illustrated embodiment, the encoding is done in two parts. First, the events from the sequence are collected and encoded using one hot encoding method. This can convert the markers in the sequence into numbers. In the second part, the time stamps can be encoded. The time can be encoded using normalization in a log scale, divided into intervals, and scaled from 0 to 1. Other variations of transformation can also be used. For example, transformation can be achieved using a combination of nominal (One Hot, N-grams, Bag-of-words, Vector semantics, Term Frequency, Inverse Frequency, Embedding, Mean, binary, or hashing) and ordinal (logarithmic, custom mathematical function based, normalized to predefined numerical range, or standardized to population statistics). Input features can also be transformed using dimensionality reduction methods (Principal Component Analysis variants, Multidimensional Scaling, Discriminant Analysis variants and Factor Analysis). Combinations and permutations of previous transformation methods can be used to create additional derived inputs based on raw inputs.

Figure 14:
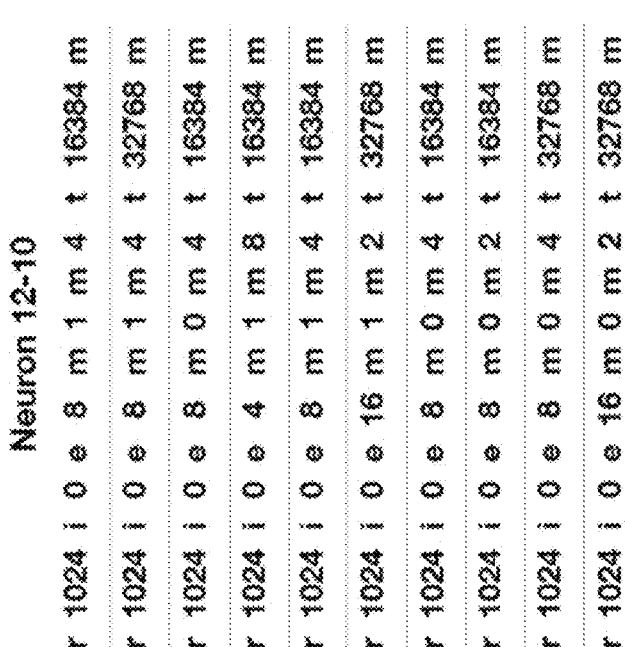
FIG. 14 illustrates an example output of an unsupervised neural network and sequences that are grouped together for a particular neuron.
Figure 14:
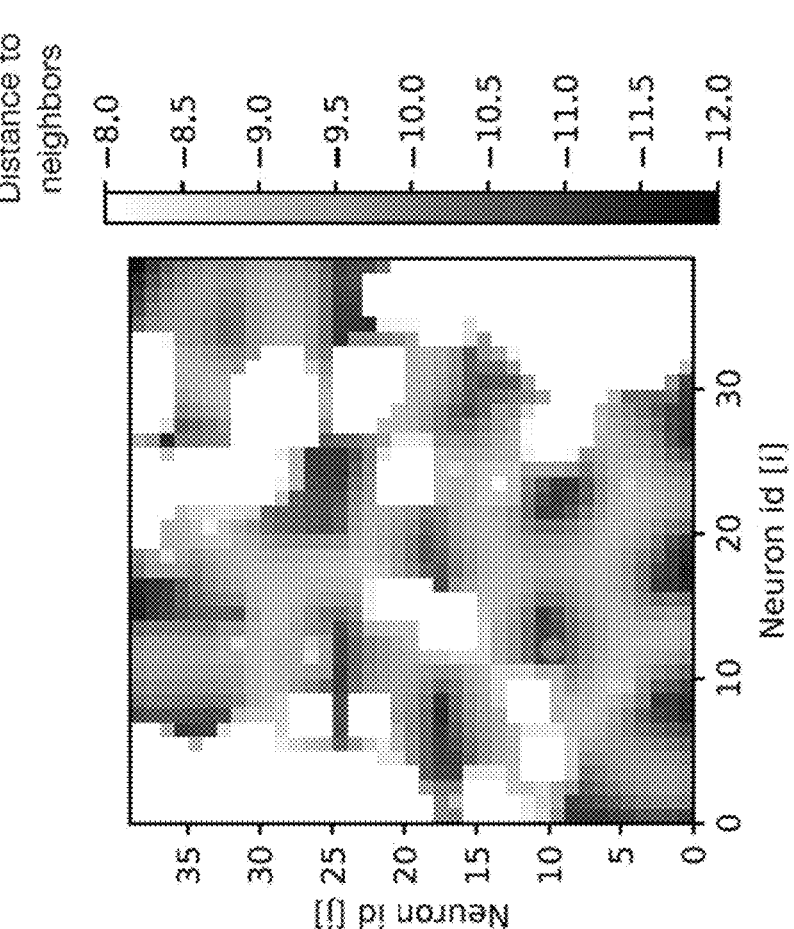
Figure 15:
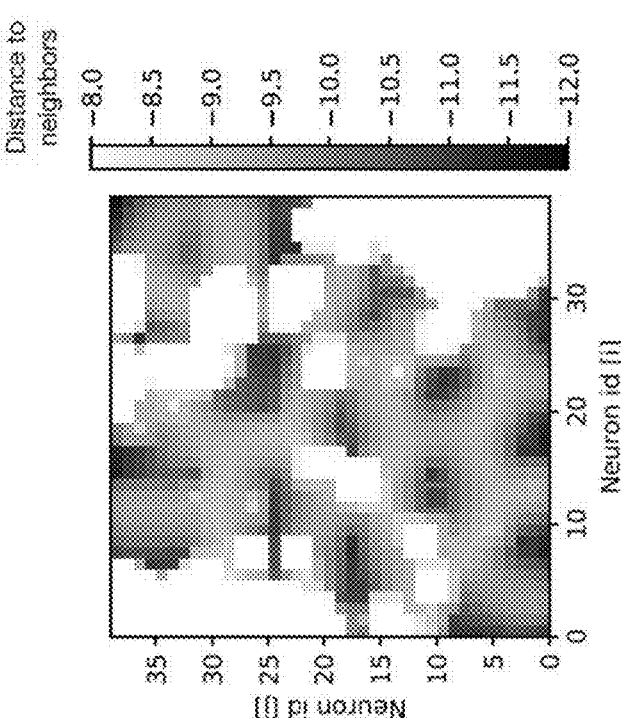
FIG. 15 illustrates another example output of an unsupervised neural network and further illustrates sequences of neighboring neurons.

FIGS. 14 and 15 illustrate an example output of the neural network representing a trained map. Each coordinate corresponds to a particular neuron and each neuron can correspond to grouping of sequences that are similar. As shown in FIG. 14, the neuron 12-10 has grouped similar sequences together. FIG. 15 shows sequences of neighboring neurons and their corresponding similarities. Thousands of sequences are grouped together based on their similarities by an application of an unsupervised neural network.

Figure 16:
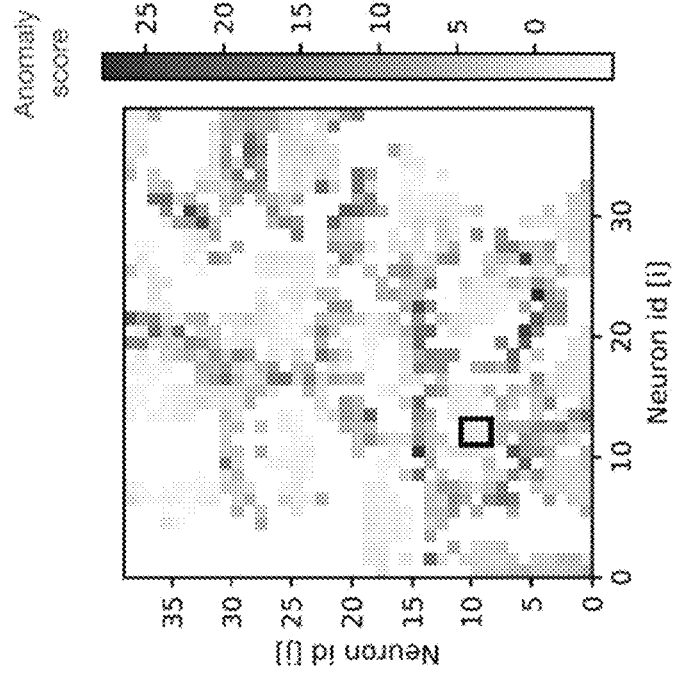
FIG. 16 illustrates mapping of anomaly scores to the output of the unsupervised neural network.
Figure 16:
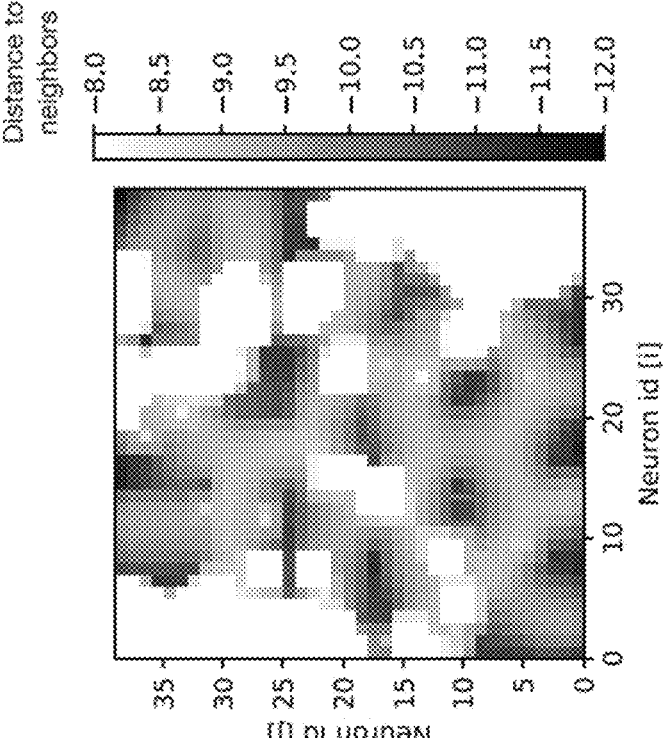

FIG. 16 illustrates how the output of the neural network can be used to map anomaly scores. As discussed above, each neuron corresponds to a group of similar sequences. For each of the sequences, the anomaly score can be calculated using the formula illustrated in FIG. 9D. The anomaly score can be averaged for all the sequences associated with a particular neuron and assigned to the particular neuron.

Figure 17:
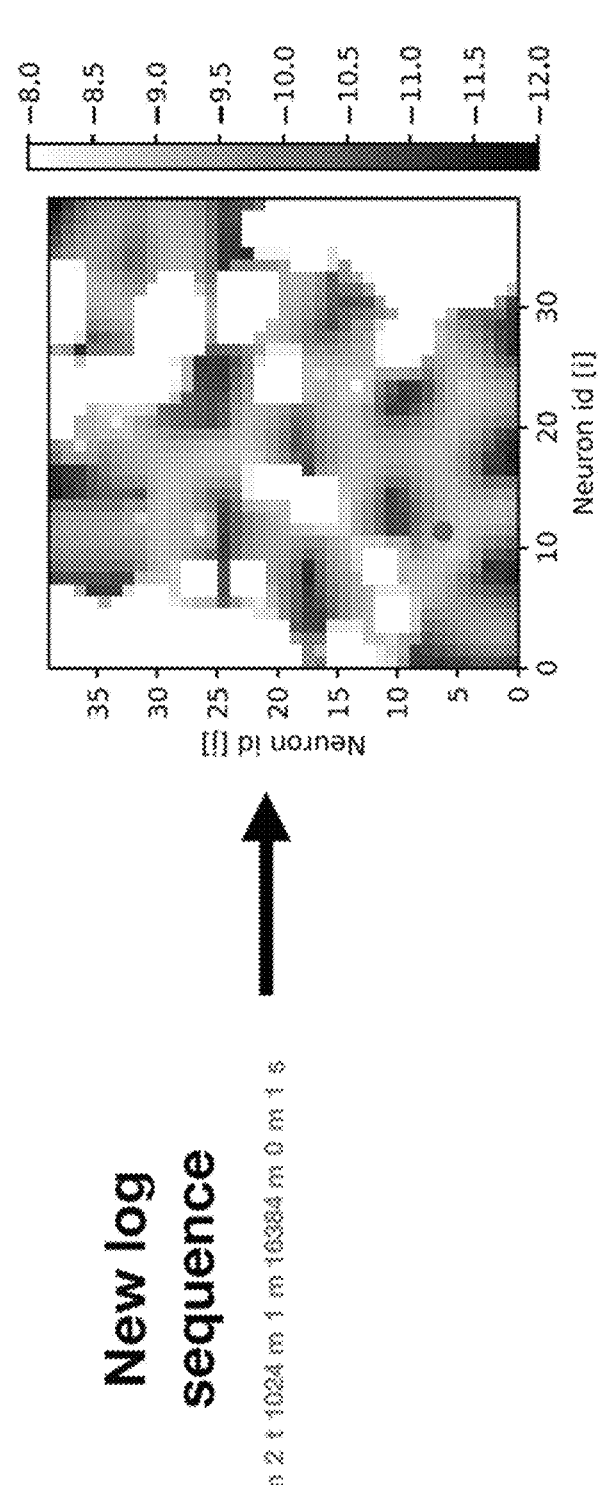
FIG. 17 illustrates mapping of new log sequences on the output of the unsupervised neural network.

FIG. 17 shows how new log sequences can be mapped on the trained map. For example, the controller 200 can identify which neuron in the trained map corresponds closest to the new sequence. Based on the identification, new sequences can be plotted on the trained map.

Figure 18:
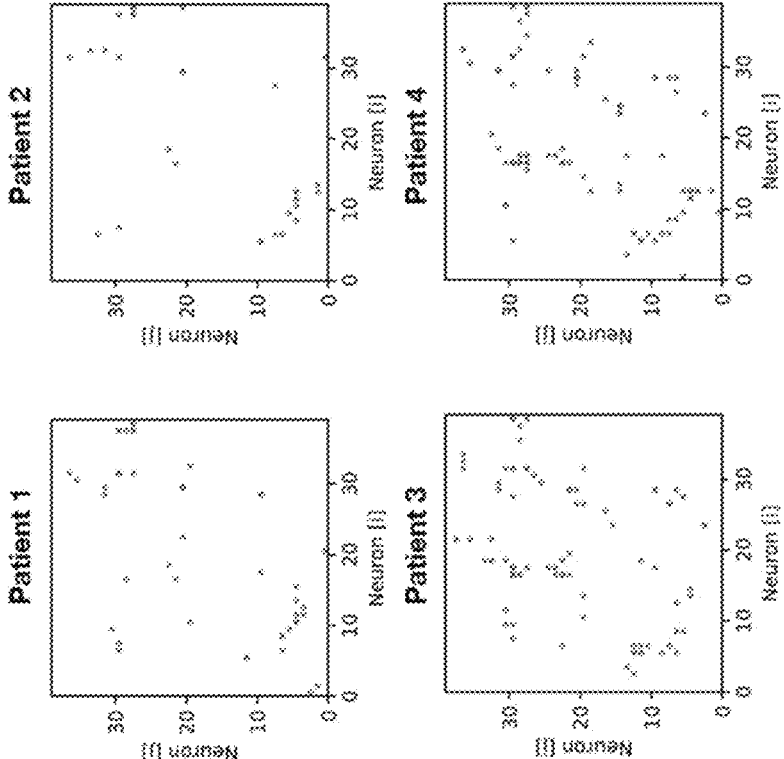
FIG. 18 illustrates example patient log sequences mapped on to the output of the unsupervised neural network.

FIG. 18 shows example patient sequences mapped on to the trained map. As illustrated, patient sequences may be grouped into clusters and these clusters can be used to identify patients with similar usage patterns.

Figure 19:
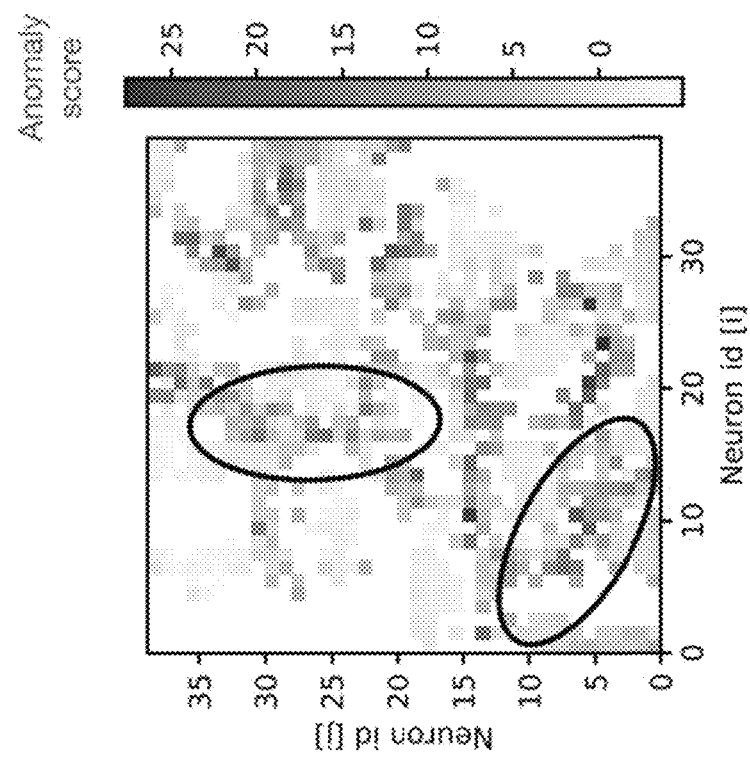
FIG. 19 illustrates selected clusters from FIG. 18 with corresponding anomaly scores.
Figure 19:
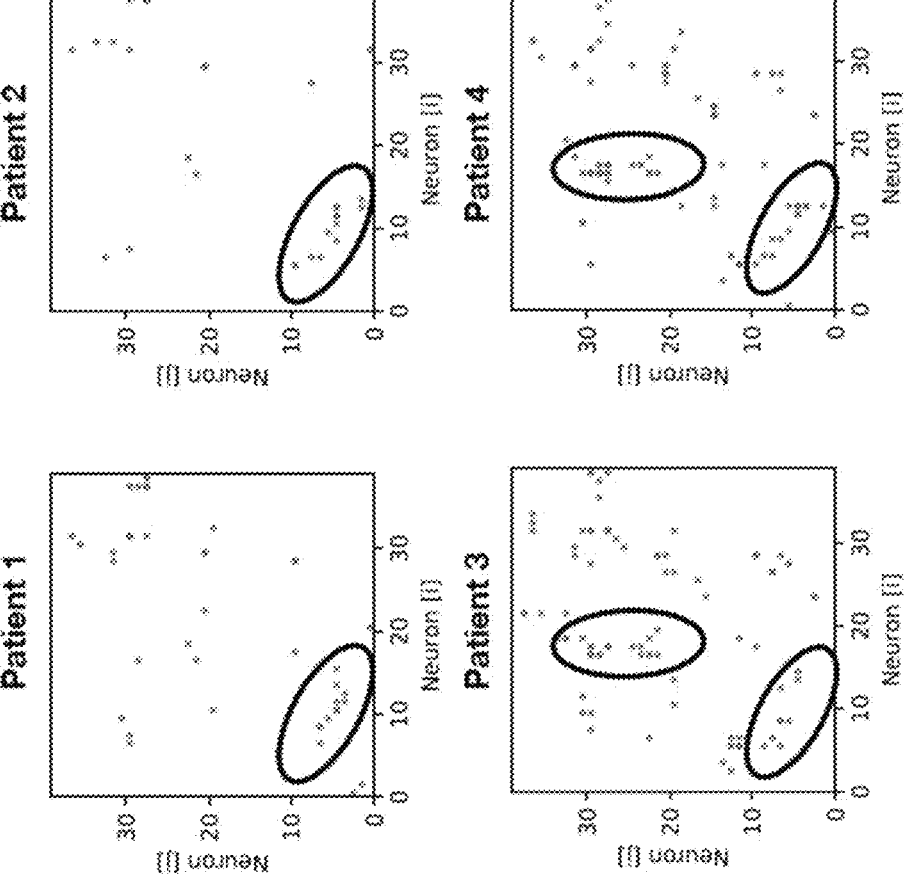

FIG. 19 shows selected clusters from FIG. 18 with corresponding anomaly scores of the neurons. The selected clusters correspond to high anomaly scores. Patient 1 and Patient 2 have similar usage patterns, while Patient 3 and Patient 4 have similar usage patterns.

Figure 20:
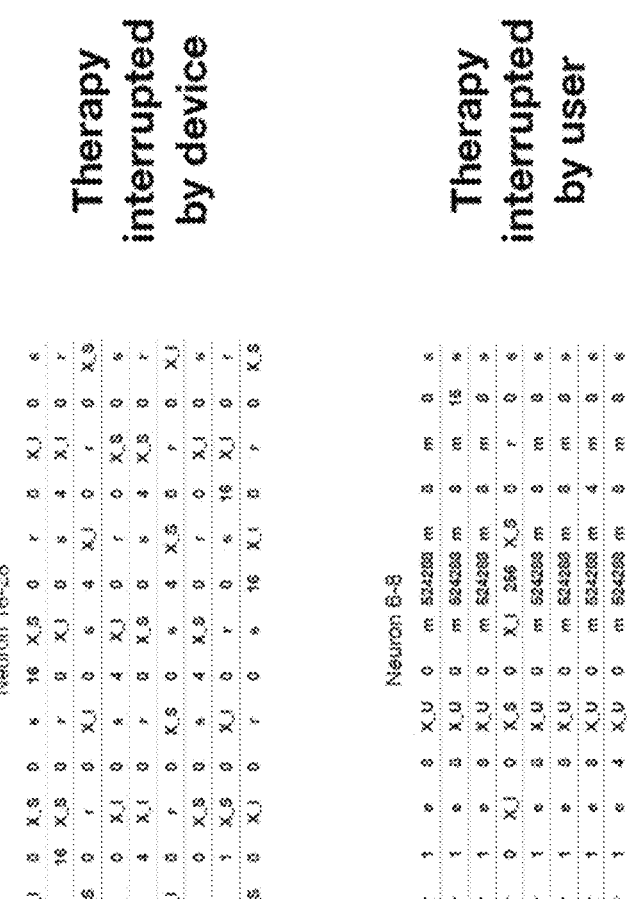
FIG. 20 illustrates a determination of specific anomalies for the selected clusters.
Figure 20:
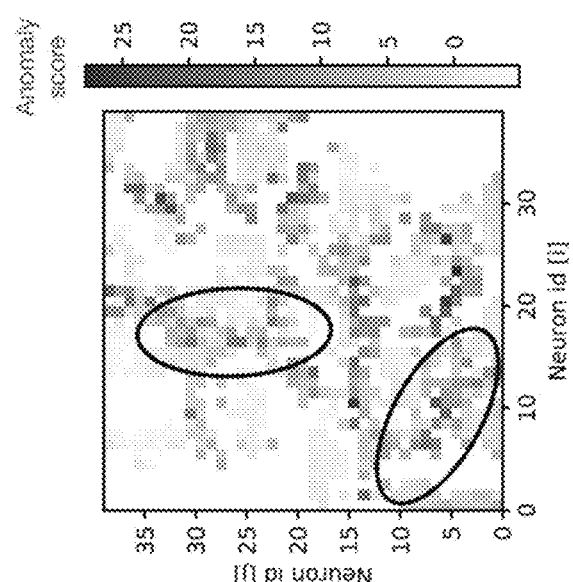

FIG. 20 shows determination of specific anomalies for the clusters. The logs can also store events like therapy interrupted by device or therapy interrupted by users and other therapy related events. Accordingly, once the grouping is done, the controller 200 can look back in the log and identify one or more characteristics from the log for that cluster. The controller 200 can then store the correlation between the distinct causes to these distinct patterns.

Figure 21:
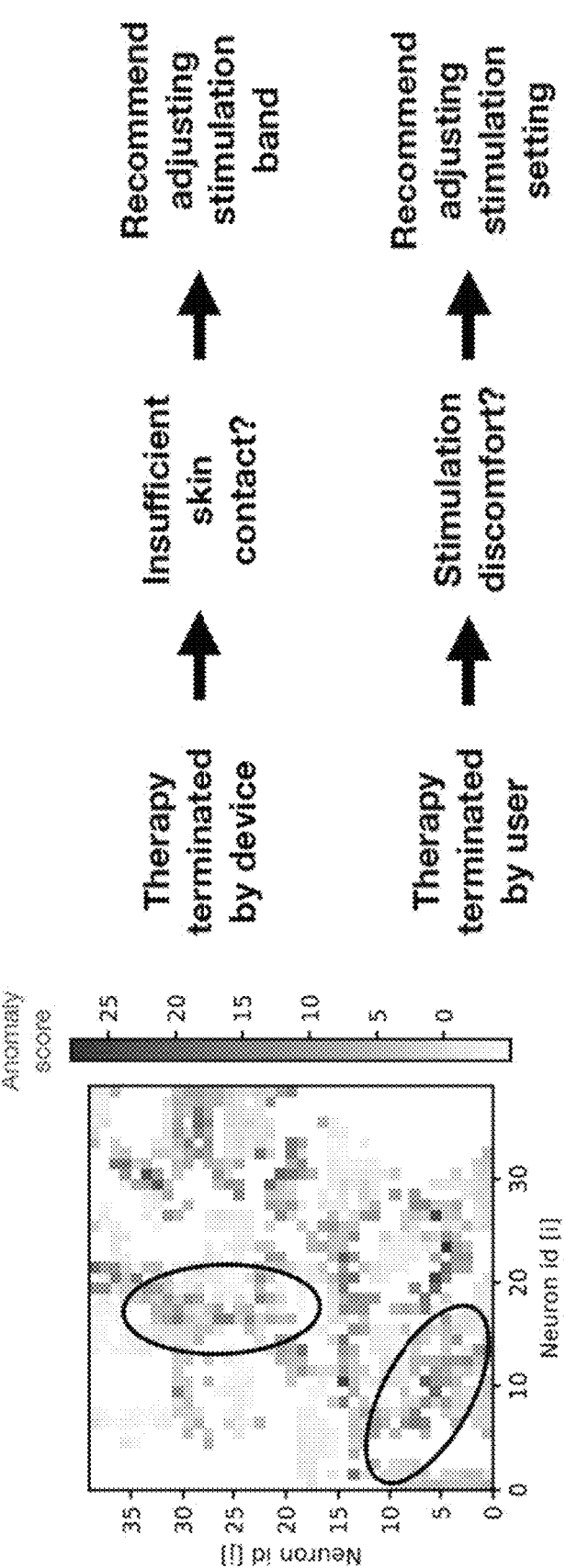
FIG. 21 illustrates example recommendations that can be sent to users.

Therefore, once the network is trained, a user's device usage log can be mapped on to the trained network to identify patterns that should be addressed. In some embodiments, a personalized tailored message can be automatically sent to the user based on identified patterns. FIG. 21 illustrates example of recommendations. In some instances, device parameters and/or treatment parameters can be changed in response to detecting patterns.

In some embodiments, systems and methods as disclosed herein can be used for personalized device usage assistance. A controller configured to perform, for example, ASDA and/or ESCA functionality can analyze device usage logs, and a user provided with corrective instructions for device usage if the user's device usage is determined to be anomalous.

In some embodiments, systems and methods as disclosed herein can be used for device error prediction. A controller configured to perform, for example, ASDA and/or ESCA functionality can analyze device function logs, and a user provided with a replacement device if the device is determined to be anomalous.

In some embodiments, the rule generation engine 206 relies on calibration instructions to determine rules between features and outcomes. The rule generation engine 206 can employ machine learning modeling along with signal processing techniques to determine rules, where machine learning modeling and signal processing techniques include but are not limited to: supervised and unsupervised algorithms for regression and classification. Specific classes of algorithms include, for example, Artificial Neural Networks (Perceptron, Back-Propagation, Convolutional Neural Networks, Recurrent Neural networks, Long Short-Term Memory Networks, Deep Belief Networks), Bayesian (Naive Bayes, Multinomial Bayes and Bayesian Networks), clustering (k-means, Expectation Maximization and Hierarchical Clustering), ensemble methods (Classification and Regression Tree variants and Boosting), instance-based (k-Nearest Neighbor, Self-Organizing Maps and Support Vector Machines), regularization (Elastic Net, Ridge Regression and Least Absolute Shrinkage Selection Operator), and dimensionality reduction (Principal Component Analysis variants, Multidimensional Scaling, Discriminant Analysis variants and Factor Analysis). In some embodiments, any number of the foregoing algorithms are not included. In some embodiments, the controller 200 can use the rules to automatically determine outcomes. The controller 200 can also use the rules to control or change settings of the neurostimulation device, including but not limited to stimulation parameters (e.g., stimulation amplitude, frequency, patterned (e.g., burst stimulation), intervals, time of day, individual session or cumulative on time, and the like).

Rules can be stored in several ways, including but not limited to any number of the following: (1) After training on a cohort of data, rules could be stored in the cloud. Data would be transmitted periodically, e.g., every night, and the rules applied once data is transmitted. Changes to stimulation or results could be send back to the device or patient monitor after execution on the cloud; (2) Rules could be stored on the device or patient monitor in memory and executed on the processor. Data collected could be processed and rules applied in real time, after a measurement, or after stimulation is applied; and/or (3) Rule generation (and modification) could happen after each therapy session based on an assessment of tremor improvement and relevant features measured before, during and after each stimulation session.

In some embodiments, systems and methods incorporate automated processing and detection of abnormal patterns but do not incorporate a predefined set of error parameters.

In some embodiments, systems and methods are configured to analyze data from event logs.

In some embodiments, systems and methods are not configured to utilize physiologic measurements in detection of abnormal patterns, such as any number of EKG data, EEG data, EMG data, and the like.

In some embodiments, systems and methods are not configured to detect abnormal events indicative of intrusions to a network or device. However, intrusions can be detected in other embodiments.

Terminology

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description. The methods disclosed herein include certain actions taken by a practitioner; however, they can also include any third-party instruction of those actions, either expressly or by implication. For example, actions such as "percutaneously stimulating an afferent peripheral nerve" includes "instructing the stimulation of an afferent peripheral nerve."

What is claimed is:

1. A method of providing an intervention with a transcutaneous neurostimulation device, the method comprising:
   collecting therapy event data from a transcutaneous neurostimulation device over time;
   splitting up the collected event data into a plurality of groups;
   transforming each of the collected event data from the plurality of groups into respective unique codes;
   training the respective unique codes using an unsupervised neural network;
   identifying an anomalous usage pattern based on the training; and
   generating an intervention to a user of the transcutaneous neurostimulation device based on the identified anomalous usage pattern.

2. The method of claim 1, wherein the collected event data comprise marker and time stamp.

3. The method of claim 1, further comprising correlating the trained neural network with one or more deviation scores.

4. The method of claim 3, wherein the anomalous usage pattern is identified based on the one or more deviation scores.

5. The method of claim 1, wherein the therapy event data comprises data recorded before a therapy event, during the therapy event, or after the therapy event.

6. The method of claim 1, wherein the therapy event data comprises patient-device interactions.

7. The method of claim 1, wherein the therapy event data comprises internal device function records.

8. The method of claim 1, wherein the intervention comprises communicating a status of one or more components of the transcutaneous neurostimulation device.

* * * * *